US012721515B2

(12) United States Patent
Eadie et al.

(10) Patent No.: US 12,721,515 B2
(45) Date of Patent: Sep. 1, 2026

(54) SYSTEM, METHOD, AND HEAD-MOUNTED DEVICE FOR VISUAL FIELD TESTING

(71) Applicant: Eadie Technologies Inc., Halifax (CA)

(72) Inventors: Brennan Eadie, Halifax (CA); Frank Eadie, Halifax (CA); Haskell Kent, Halifax (CA); Anthony Visconti, Halifax (CA)

(73) Assignee: Eadie Technologies Inc., Halifax (CA)

( * ) Notice: Subject to any disclaimer, the term of this patent is extended or adjusted under 35 U.S.C. 154(b) by 609 days.

(21) Appl. No.: 18/009,124

(22) PCT Filed: Jun. 11, 2021

(86) PCT No.: PCT/CA2021/050798
§ 371 (c)(1),
(2) Date: Dec. 8, 2022

(87) PCT Pub. No.: WO2021/248249
PCT Pub. Date: Dec. 16, 2021

(65) Prior Publication Data

US 2023/0218159 A1 Jul. 13, 2023

Related U.S. Application Data

(60) Provisional application No. 63/038,084, filed on Jun. 11, 2020.

(51) Int. Cl.

| | |
|---|---|
| ***A61B 3/024*** | (2006.01) |
| ***A61B 3/00*** | (2006.01) |
| ***G02B 27/00*** | (2006.01) |

(52) U.S. Cl.
CPC .............. *A61B 3/024* (2013.01); *A61B 3/005* (2013.01); *A61B 3/0091* (2013.01); *G02B 27/0093* (2013.01)

(58) Field of Classification Search
CPC ....... A61B 3/024; A61B 3/005; A61B 3/0091; A61B 5/1071; A61B 5/163; A61B 5/6803; A61B 3/113; A61B 3/14; G02B 27/0093

(Continued)

(56) References Cited

U.S. PATENT DOCUMENTS

| | | | | |
|---|---|---|---|---|
| 5,909,269 A * | 6/1999 | Isogai | .................... | A61B 3/152 351/208 |
| 2014/0268051 A1* | 9/2014 | Maor | .................... | A61B 3/113 351/246 |

(Continued)

FOREIGN PATENT DOCUMENTS

| | | | |
|---|---|---|---|
| CN | 1960670 A * | 5/2007 | ............. G02B 27/00 |
| CN | 203444715 U * | 2/2014 | |

(Continued)

OTHER PUBLICATIONS

Gross et al. "Handbook of Optical Systems Volume 3: Aberration Theory and Correction of Optical Systems" Weinheim Germany, WILEY-VCH Verlag GmbH & Co. KGaA, pp. 377-379 (Year: 2007).*

*Primary Examiner* — William R Alexander
*Assistant Examiner* — Alaina Marie Swanson
(74) *Attorney, Agent, or Firm* — Adrian D. Battison; Ryan W. Dupuis; Ade & Company Inc.

(57) ABSTRACT

An apparatus for vision testing comprises a visual test unit (VTU) configured to receive a patients face and perform the vision test on the patient. The VTU includes an internal display configured to generate a light stimulus and a gaze sensor configured to track the eye of the patient. In one aspect, a plurality of VTUs form a system controllable by a common technician to concurrently administer vision tests on different patients. In another aspect, the gaze sensor comprises a camera configured to capture a video of the (Continued)

patients eye displayed to the technician. In another aspect, the VTU is configured to pause testing upon detection of an adverse testing condition such as excessive head tilt or a closed eye. In another aspect, the test display comprises an array of LEDs and a perforated opaque screen to provide sufficient luminance. In another aspect, the VTU comprises a head mounted portion with a pair of focusing lenses and a mirror arranged to transmit light from the test display to the eyepiece and from the eyepiece to the gaze sensor. In another aspect, the VTU includes a patient input device configured to receive input from the patient to signal observance of a light stimulus in the visual field around a fixation point, and the VTU is configured to monitor the patients gaze and pause the test upon detecting that the patients gaze has moved from the fixation point.

28 Claims, 29 Drawing Sheets

(58) Field of Classification Search
USPC .......................................................... 351/209
See application file for complete search history.

(56) References Cited

U.S. PATENT DOCUMENTS

2016/0320625 A1* 11/2016 von und zu Liechtenstein ........... G02B 27/0179
2018/0271359 A1* 9/2018 Inoue .................. A61B 3/0091

FOREIGN PATENT DOCUMENTS

| | | | | | |
|---|---|---|---|---|---|
| CN | 107478412 | A | * | 12/2017 | ............. G06F 3/012 |
| CN | 207601420 | U | * | 7/2018 | |
| CN | 109700424 | A | * | 5/2019 | |
| DE | 112011101997 | T5 | * | 10/2013 | ............. C12N 13/00 |
| EP | 3210525 | | | 8/2017 | |
| JP | H11309114 | A | * | 11/1999 | |
| KR | 102053794 | B1 | * | 12/2019 | ............ B60W 40/02 |
| WO | WO 2016173652 | | | 11/2016 | |
| WO | WO-2016173652 | A1 | * | 11/2016 | ............. A61B 3/024 |
| WO | WO 2019019805 | | | 1/2019 | |
| WO | WO-2019019805 | A1 | * | 1/2019 | ............. A61B 3/113 |
| WO | WO-2019163911 | A1 | * | 8/2019 | ............... A61B 3/10 |

* cited by examiner 1500
1502
1522
1508
1516
1504
1514
1510
1506
1518
1512
1520

1302
1304
1314
1320
1312
1326
1308
1306
1322
1318
1300
1310
1319
1324
1316

1328
1330

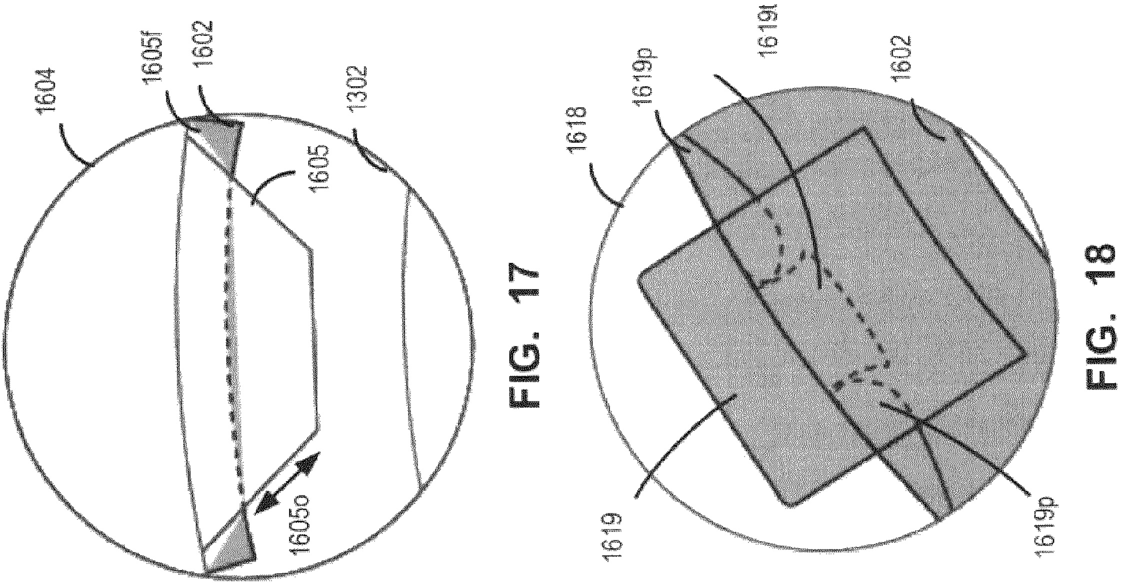
FIG. 17
FIG. 18
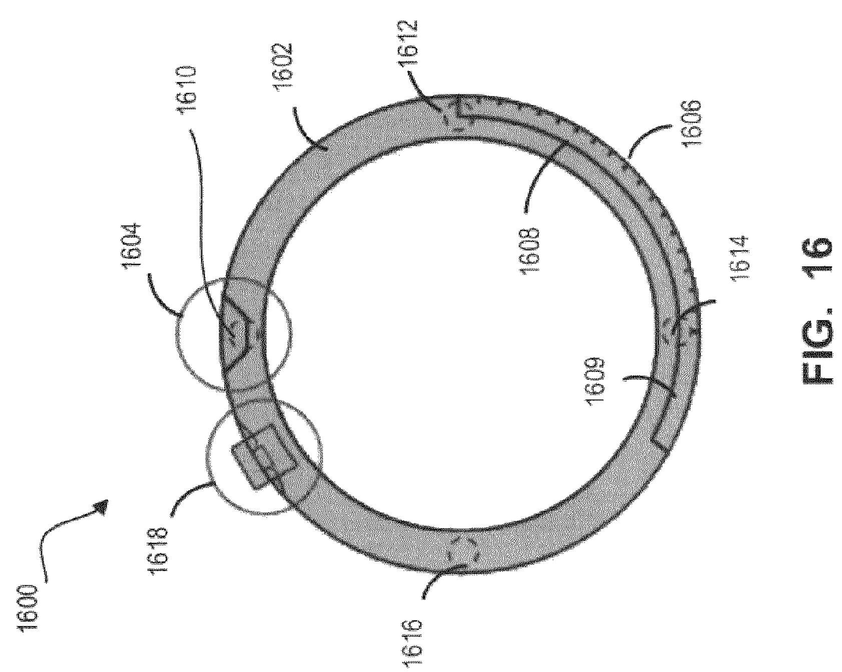
FIG. 16

3338
3304A
3304
3311
3307
3301
3315
3312
3307A
3338
3341
Image Processing Board
Display
3336
3340
DC Power

SYSTEM, METHOD, AND HEAD-MOUNTED DEVICE FOR VISUAL FIELD TESTING

This application is a national phase filing of PCT/CA2021/050798 and claims priority from U.S. Provisional Application Ser. No. 63/038,084 filed Jun. 11, 2020.

FIELD OF THE DISCLOSURE

The teachings herein generally relate to visual field testing and, more particularly, to various embodiments for a system, method and device comprising a set of head-mounted goggles linked to a control unit for visual field testing and other vision tests.

BACKGROUND AND DESCRIPTION OF USE AND DEFICIENCIES OF THE CURRENT GOLD STANDARD DEVICES

Glaucoma, the leading cause of irreversible blindness worldwide, is a group of eye diseases characterized by abnormalities of the optic disc and progressive damage to the optic nerve, which results in associated patterns of visual field loss. Early diagnosis, frequent monitoring of disease progression and treatment of glaucoma are critical to prevent further significant irreversible vision loss.

Visual field testing (also known as perimetry) is integral to the diagnosis and management of glaucoma. In a visual field test, the sensitivity of a patient's visual system is tested at various locations eccentric to a central fixation point. Normal physiology allows for the greatest sensitivity centrally with sensitivity gradually decreasing to the periphery. Accordingly, the visual field test is used to generate a map showing the sensitivity of the patient's vision at locations eccentric to fixation in the field of view. The generated visual field maps inform clinicians as to the nature and severity of visual field loss. Repeat testing is used to monitor for generalized and point-wise progression of visual field damage. Visual field patterns, severity, and progression influence clinical treatment decisions.

Common conventional visual analyzer devices include the Zeiss® Humphrey® Field Analyzer (HFA) and the Haag-Streit® Octopus® perimeter devices. Such devices are herein referred to as the "Conventional Gold Standard Devices". These devices typically comprise a desk-mounted apparatus with an attached "clicking" device that is held by the patient during the course of the perimeter test. In most cases, a chin rest (or head rest) is provided for resting the patient's chin and/or head. In performing the visual field test, the patient is asked to cover one eye (e.g., using an eye patch), while, with the uncovered eye, maintain central fixation on a central fixation point disposed on a distally positioned screen. As the patient focuses their gaze on the central target, the system generates a series of brief light stimuli, on the distal screen, to the uncovered eye. The light stimuli may be displayed at different positions eccentric to the central fixation target (i.e., in the patient's side or peripheral visual field), and at a gradation of intensities. The patient is then asked to depress (i.e., click) a depressible button, disposed on the clicker device, whenever a light stimulus is observed by the patient. This method of visual field testing is herein referred to as a "Standard Clicker Test".

In various cases, the position and pattern of the light stimuli vary depending on the visual field test program that is selected. For example, in a 30-1 or 30-2 visual field test, light stimuli are presented at points located within 30° from the central fixation point, and in all axial directions from the central point. In a 30-1 test, in particular, light stimuli are presented on intervals of 6° along the x- and y-axes on the distal display, while in a 30-2 test, light stimuli are presented 3° away from the x- and y-axes and then on intervals of 6° on the distal display. Other vision tests include, inter alia, 24-2, 24-1, 10-2 and 10-1 tests. The light stimuli may be presented in a range of sizes. The standard five sizes are referred to as the Goldmann Size I to Size V. These various standard visual field tests are referred to herein as "Standard Tests". In most cases, as the Standard Test is being performed, a technician may monitor the patient's head and eye position to ensure that the patient maintains fixation on the central fixation point. In cases where the patient's head or eye position become offset, the technician can re-adjust the chin or head rest to re-centre the patient's position. At the completion of the visual field test, the conventional device generates a statistical report of the collected data. For example, the report can include a visual grid which maps the lowest intensity level of light stimulus recognized by the patient at each co-ordinate point in the tested field of vision. The report can also include other statistical analysis results.

The subjective element of the test results in much of the conventional technology's unreliability. False negatives occur in the current standard perimetry test when the patient does not push the clicker button in response to a suprathreshold light stimulus in a location where the patient previously detected the light stimulus. False positives occur when the patient depresses the clicker button when no light stimulus is presented or a light stimulus has been presented that is not a suprathreshold light stimulus and the patient has depressed the clicker button. Moreover, fixation losses occur because the patient either does not understand the instruction to maintain fixation on the central fixation point or is unable to inhibit the natural tendency to move one's eyes to scan a scene or look towards stimuli. Fixation losses also lead to unreliable test results because subsequently presented stimuli are no longer actually being presented the actual distance from fixation that the system records as the distance from fixation. Also, if a patient is having difficulty with the test, the test takes a longer time to complete, which leads to greater unreliability. The conventional testing device also requires one eye to be tested at a time which can lead to greater unreliability in the second eye compared to the first eye tested.

Conventional gold standard visual field testing technology does not adequately correct for the above-noted sources of inaccuracy. In particular, while some Conventional Gold Standard Devices may report incidences of fixation loss, false positives, and false negatives, these devices are otherwise unable to prevent or eliminate these inaccuracies. This can lead to diagnostic and treatment errors, potentially resulting in negative consequences for patients.

In addition to the issue of inaccuracy and unreliability of test results as described above, there is a significant issue of patient stress and discomfort. When a Standard Clicker Test is being conducted using one of the Conventional Gold Standard Devices patient discomfort can arise from the following factors: (a) the requirement to signal recognition of light stimuli as they are presented rapidly in different locations, particularly when the stimulus is of a brightness near the threshold level of recognition; (b) the requirement to maintain continuous fixation on a central fixation point for an extended period of time while the test is being conducted; and (c) the requirement to keep their head still for an extended period of time while the test is being conducted.

The issues of test unreliability and patient discomfort are interrelated. For example, the requirement that the patient must keep his or her head still for a protracted period of time can lead to a loss of fixation.

Further, Conventional Gold Standard Devices require that the Standard Clicker Test be conducted in a dedicated darkened room by a trained technician. Only one test can be administered at a time on one patient. These factors result in significant overhead and salary costs for the clinician.

Given normal physiology, the gaze of patients' eyes will move during a visual field test randomly. Therefore, in order to conduct a visual field test using eye tracking technology it is necessary to determine if the eye movement detected was made in response to a presented stimulus.

SUMMARY OF THE DISCLOSURE AND VARIOUS EMBODIMENTS OF THE INVENTION

According to an aspect of the invention there is provided an apparatus for administering a vision test to a patient comprising:

- a visual test unit configured to receive a face of the patient and to perform the vision test on the patient, wherein the visual test unit includes:
  - an internal test display arranged in front of the patient's face and configured to generate a light stimulus to conduce movement of an eye of the patient; and
    - a gaze sensor configured to track the eye of the patient. An independent optional important feature is that there are provided a plurality of the visual test units forming a system for use by a technician to administer vision tests on a plurality of patients, where each of the visual test units is assigned to a different one of the patients.

An independent optional important feature is that each visual test unit is configured to receive, as input, parameters for configuring the visual test unit for the vision test to be performed thereon, where the parameters are associated with the different one of the patients to which the visual test unit is assigned.

Typically, the parameters include at least one of: (i) an eye to be tested, (ii) a grid testing area for defining locations where light stimuli are presented in a visual field of the patient; and (iii) corrective lens prescription;

Further to the foregoing list, the parameters may include at least one of: (iv) interpupillary distance; (v) stimulus size for defining a size of the light stimulus; and (vi) patient response type to identify a format of input received from the patient to signal observance of a light stimulus.

An important optional independent feature is that the system further includes a computing device operatively communicated with the visual test units and configured to receive, as input from the technician, the parameters for communication to the visual test units.

Such an embodiment of system of multiple visual test units is thus suited for enabling a single technician to carry out vision tests on different patients in parallel, or in other words concurrently.

An independent optional important feature is that the gaze sensor comprises a camera configured to capture a video of the eye of the patient.

An independent optional important feature is that the apparatus includes a technician display configured to display the video to the technician administering the vision test in order to monitor the patient.

An independent optional important feature is that the apparatus includes a technician device distinct from the visual test unit which is operatively communicated with the visual test unit and configured to control the visual test unit, and the technician device includes the technician display such that the video of the patient's eye is remotely observable.

An independent optional important feature is that the visual test unit comprises a head mounted unit configured for mounting to the head of the assigned patient.

An independent optional important feature is that the head mounted unit includes the camera.

An independent optional important feature is that the visual test unit includes the technician display which is external such that the video is observable by the technician for aligning the head mounted unit on the patient.

An independent optional important feature is that the technician display is distinct from the head mounted unit.

An independent optional important feature is that the visual test unit is configured to detect an adverse testing condition of the patient under which inaccurate results of the vision test are obtained, and that the visual test unit is configured to pause the vision test in response to detection of the adverse testing condition.

An independent optional important feature is that the visual test unit is configured to resume the paused vision test in response to determination that the adverse testing condition is removed.

When the visual test unit comprises a head mounted unit configured for mounting to the head of the patient, and when the head mounted unit includes the gaze sensor and the internal test display, an independent optional important feature is that the head mounted unit further includes a head tilt sensor configured to detect a tilt angle of a head of the patient relative to a vertical plane. and An independent optional important feature is that the visual test unit is configured to pause the vision test for the patient in response to a detected tilt angle exceeding a prescribed threshold angle.

Typically, the test is paused when the detected tilt angle exceeds the prescribed threshold angle for a threshold duration.

An independent optional important feature is that the head tilt sensor is also configured to detect a tilt angle of the head of the assigned patient relative to a reference tilt angle of the patient's head in a relaxed position.

An independent optional important feature is that the prescribed threshold angle is about 20 degrees.

An independent optional important feature is that the gaze sensor is configured to detect closure of the eye.

An independent optional important feature is that the adverse testing condition comprises a closed eye.

An independent optional important feature is that the visual test unit includes an eyepiece in front of the internal test display and configured to receive the patient's eye for viewing the light stimulus.

An independent optional important feature is that the internal test display comprises an array of light-emitting devices configured to emanate light towards the eyepiece and an opaque screen in front of the array of light-emitting devices and configured to block the light therefrom.

An independent optional important feature is that the screen locates a plurality of openings to permit passage of light to the eyepiece at select locations of the patient's visual field.

An independent optional important feature is that the openings comprise a central opening in a center of the screen for a central fixation point of the vision test and a plurality of peripheral openings at spaced locations on the screen.

When the visual test unit comprises a head mounted unit configured for mounting to the head of the patient, and the head mounted unit includes a housing configured to be supported on the head of the patient, and the housing carries the internal test display and the gaze sensor, and the gaze sensor is configured to track the eye of the patient by light rays reflected therefrom, and the head mounted unit includes an eyepiece supported on the housing and configured to receive the patient's eye for viewing the light stimulus, an independent optional important feature is that the head mounted unit further includes an optical assembly in the housing and configured for transmitting the light stimulus to the eyepiece and light, emanating from the eye of the patient, from the eyepiece to the gaze sensor.

An independent optional important feature is that one of the gaze sensor and the internal test display is located along a line of sight defined by the eyepiece but at a spaced distance therefrom, to define an in-line testing element.

An independent optional important feature is that the optical assembly comprises a plurality of lenses arranged to focus light emanating from the in-line testing element and onto the patient's eye received at the eyepiece, and a mirror arranged to reflect light, transmitted through the eyepiece and into the housing, to another one of the gaze sensor and the internal test display.

An independent optional important feature is that the plurality of lenses includes a first focusing lens disposed along the line of sight and adjacent and in front of the in-line testing element, so as to be intermediate the in-line testing element and the eyepiece, and configured to partially refract light rays emanating therefrom from the in-line testing element.

An independent optional important feature is that the plurality of lenses includes a second focusing lens disposed along the line of sight and adjacent and behind the eyepiece, and configured to refract the light rays transmitted through the first focusing lens.

An independent optional important feature is that the mirror is disposed along the line of sight between the first and second focusing lenses and is configured to transmit light from the in-line testing element but reflect light transmitted through the eyepiece.

An independent optional important feature is that the first and second focusing lenses are the only lenses of the optical assembly.

An independent optional important feature is that the first and second focusing lenses are non-Fresnel lenses.

An independent optional important feature is that the first focusing lens is biconcave.

An independent optional important feature is that a proximal side of the first focusing lens to the in-line testing element has a smaller arc than an arc of an opposite side of the first focusing lens proximal to the mirror.

An independent optional important feature is that the second focusing lens is biconvex.

An independent optional important feature is that a proximal side of the second focusing lens to the eyepiece has a larger arc than an arc of an opposite side of the second focusing lens proximal to the mirror.

An independent optional important feature is that the mirror is configured to transmit light rays, which emanate from the in-line testing element, having frequencies within a first frequency range and to reflect light rays, which emanate from the eyepiece, having frequencies in a second frequency range distinct from the first frequency range.

An independent optional important feature is that the first and second frequency ranges are a visible light range and an infrared range.

An independent optional important feature is that the first frequency range is lower than the second frequency range.

An independent optional important feature is that, in a different embodiment, the first frequency range is higher than the second frequency range.

An independent optional important feature is that the mirror of the optical assembly is oriented at an inclined angle and another one of the gaze sensor and the internal test display is arranged beyond the line of sight and in opposite relation to the mirror.

An independent optional important feature is that the another one of the gaze sensor and the internal test display has a line of sight which is transverse but not perpendicular to the line of sight of the eyepiece.

An independent optional important feature is that the line of sight of the another one of the gaze sensor and the internal test display is offset from a height center of the mirror between its upper and lower ends.

An independent optional important feature is that the visual test unit includes a patient input device configured to receive input from the patient to signal observance of a light stimulus in the visual field around a fixation point during the vision test.

An independent optional important feature is that the visual test unit is further configured to:

- monitor gaze of the patient at the fixation point during the vision test, and
- if the gaze of the patient is determined to have moved from the fixation point during the vision test, then pause the vision test, and resume the vision test when the gaze of the patient is determined to have returned to the fixation point.

According to another aspect of the invention, there is provided an apparatus for use by a technician to administer a vision test on a patient comprising:

- a visual test unit configured to receive a face of the patient and to perform the vision test on the patient, wherein the visual test unit includes:
  - an internal test display arranged in front of the patient's face and configured to generate a light stimulus to conduce movement of an eye of the patient; and
  - a camera configured to capture a video of the eye of the patient; and
- a technician display configured to display the video to the technician for monitoring the patient.

According to another aspect of the invention, there is provided an apparatus for administering a vision test on a patient comprising:

- a visual test unit configured to receive a face of the patient and to perform the vision test on the patient, wherein the visual test unit includes:
  - an internal test display arranged in front of the patient's face and configured to generate a light stimulus to conduce movement of an eye of the patient; and
  - a gaze sensor configured to track the eye of the patient;
- wherein the visual test unit is configured to detect an adverse testing condition of the patient under which inaccurate results of the vision test are obtained; and
- wherein the visual test unit is configured to pause the vision test in response to detection of the adverse testing condition.

According to another aspect of the invention, there is provided an apparatus for administering a vision test on a patient comprising:

a visual test unit configured to perform the vision test on the patient, wherein the visual test unit includes:

an internal test display arranged in front of the patient's face and configured to generate a light stimulus to conduce movement of an eye of the patient; and an eyepiece in front of the internal test display and configured to receive the patient's eye for viewing the light stimulus; and wherein the internal test display comprises an array of light-emitting devices configured to emanate light towards the eyepiece and an opaque screen in front of the array of light-emitting devices and configured to block the light therefrom;

wherein the screen locates a plurality of openings therein that are registered with select ones of the light-emitting devices of the array to permit passage of light to the eyepiece at select locations of the patient's visual field.

According to another aspect of the invention, there is provided an apparatus for administering a vision test on a patient comprising:

a visual test unit configured to receive a face of the patient and to perform the vision test on the patient, wherein the visual test unit includes a head mounted unit configured for mounting to the head of the patient, wherein the head mounted unit includes:

a housing configured to be supported on the head of the patient, an internal test display in the housing for generating a light stimulus to conduce movement of an eye of the patient, a gaze sensor in the housing and configured to track the eye of the patient by light rays reflected therefrom, an eyepiece supported on the housing and configured to receive the patient's eye for viewing the light stimulus, and an optical assembly in the housing and configured for transmitting the light stimulus to the eyepiece and light, emanating from the eye of the patient, from the eyepiece to the gaze sensor;

wherein one of the gaze sensor and the internal test display is located along a line of sight defined by the eyepiece but at a spaced distance therefrom, to define an in-line testing element;

wherein the optical assembly comprises a plurality of lenses arranged to focus light emanating from the in-line testing element and onto the patient's eye received at the eyepiece, and a mirror arranged to reflect light, transmitted through the eyepiece and into the housing, to another one of the gaze sensor and the internal test display;

wherein the plurality of lenses includes a first focusing lens disposed along the line of sight and adjacent and in front of the in-line testing element, so as to be intermediate the in-line testing element and the eyepiece, and configured to partially refract light rays emanating therefrom from the in-line testing element;

wherein the plurality of lenses includes a second focusing lens disposed along the line of sight and adjacent and behind the eyepiece, and configured to refract the light rays transmitted through the first focusing lens; and wherein the mirror is disposed along the line of sight between the first and second focusing lenses and is configured to transmit light from the in-line testing element but reflect light transmitted through the eyepiece.

According to another aspect of the invention, there is provided an apparatus for administering a vision test on a patient comprising:

a visual test unit configured to receive a face of the patient and to perform the vision test on the patient, wherein the visual test unit includes:

an internal test display arranged in front of the patient's face and configured to generate a light stimulus to conduce movement of an eye of the patient; and a gaze sensor configured to track the eye of the patient; and wherein the visual test unit includes a patient input device configured to receive input from the patient to signal observance of a light stimulus in the visual field around a fixation point during the vision test; and wherein the visual test unit is further configured to:

monitor gaze of the patient at the fixation point during the vision test, and if the gaze of the patient is determined to have moved from the fixation point during the vision test, then pause the vision test, and resume the vision test when the gaze of the patient is determined to have returned to the fixation point.

According to another aspect of the invention, there is provided a system for use by a technician to administer vision tests on a plurality of patients comprising:

a plurality of visual test units configured to receive faces of the patients and to perform the vision tests on the patients, wherein each of the visual test units is assigned to a different one of the patients;

wherein each visual test unit is configured to receive, as input, parameters for configuring the visual test unit for the vision test to be performed thereon, wherein the parameters are associated with said different one of the patients to which the visual test unit is assigned, wherein the parameters include at least one of: (i) an eye to be tested, (ii) a grid testing area for defining locations where light stimuli are presented in a visual field of the patient; and (iii) corrective lens prescription; and a computing device operatively communicated with the visual test units and configured to receive, as input from the technician, the parameters for communication to the visual test units.

System for Performing Multiple Tests

In one aspect, in accordance with the teachings herein, there is disclosed a system for performing multiple vision tests on a plurality of patients, wherein the system comprises: a plurality of Visual Test Units for performing one or more vision tests, wherein each Visual Test Unit is used with a corresponding patient; and a Technician Computer that is used by a single Technician, the Technician Computer having: a communication interface for communicating with the plurality of Visual Test Units over a communication network; a display screen for presenting a user interface to allow the Technician to interact with the plurality of Visual Test Units; and a processor that is operatively coupled to the communication interface and the display screen, the processor being configured to: display the user interface on the display screen of the Technician Computer; receive Technician commands from the Technician for selecting vision tests to be performed using each of the plurality of Visual Test Units; and transmit the Technician commands via the communication interface over the communication network to the plurality of Visual Test Units to configure the Visual Test Units for performing the selected vision tests.

In at least one embodiment, the plurality of Visual Test Units are configured to perform the selected vision tests in parallel or sequentially.

In at least one embodiment, each Visual Test Unit comprises eye tracking cameras for obtaining video images of the eyes of the corresponding patient during vision testing, each Visual Test Unit is configured to send the video images to the Technician Computer and the processor of the Technician Computer is configured to display the video images on the user interface.

In at least one embodiment, the user interface is configured to display each of the video images during vision testing to allow the Technician to monitor several vision tests being conducted at the same time.

In at least one embodiment, the user interface is configured to allow the Technician to enter a pause command to pause the vision testing for a particular patient when the video images of the eyes of the particular patient indicate that the particular patient is unable to correctly undergo the vision testing, the processor is configured to send the pause command to the Visual Test Unit for the particular patient and the Visual Test Unit is configured to pause the vision testing after receiving the pause command.

In at least one embodiment, each of the Visual Test Units comprises a Control Unit and a Head Mounted Unit that is physically separate from the Control Unit and communicatively coupled to the Control Unit, wherein the Head Mounted Unit is worn on a head of the corresponding patient and the Head Mounted Unit is configured to generate visual stimuli that are presented to the patient during vision testing under the control of the Control Unit.

In at least one embodiment, the Head Mounted Unit comprises a position sensor for obtaining head movement data for the patient during vision testing and the Control Unit is configured to pause vision testing when the head movement data indicates that a tilt in the position of the head of the patient head is greater than a pre-determined head tilt threshold with respect to a normal position or absolute vertical for longer than a predetermined head tilt deviation time.

In at Least One Embodiment, One of the Control Units is a Master Control Unit that Includes memory and the Master Control Unit is configured to store vision test data for the vision tests conducted by all of the Control Units on the memory.

Method for Providing Multiple Tests

In another aspect, in accordance with the teachings herein, there is provided a method for performing multiple vision tests on a plurality of patients, wherein the method comprises: assigning each Visual Test Unit from a plurality of Visual Test Units to a corresponding patient from the plurality of patients, where each Visual Test Unit is configured to perform vision testing; connecting a Technician Computer, that is used by a single Technician, to the plurality of Visual Test Units via a communication network; presenting a user interface on a display screen of the Technician Computer to allow the Technician to interact with the plurality of Visual Test Units; receiving Technician commands from the Technician for selecting vision tests to be performed using each of the plurality of Visual Test Units and transmitting the Technician commands over the communication network to the plurality of Visual Test Units to configure the Visual Test Units for performing the selected vision tests.

In at least one embodiment, the method comprises operating the Visual Test Units for performing the selected vision tests in parallel or sequentially.

In at least one embodiment, each Visual Test Unit comprises eye tracking cameras and the method further comprises: obtaining video images of the eyes of the corresponding patient during vision testing; sending the video images to the Technician Computer; and displaying the video images on the user interface for monitoring by the Technician.

In at least one embodiment, the method further comprises displaying each of the video images from different Visual Test Units on the display screen of the Technician Computer during vision testing to allow the Technician to monitor several vision tests being conducted at the same time.

In at least one embodiment, the method further comprises receiving a pause command from the Technician to pause the vision testing for a particular patient when the video images of the eyes of the particular patient indicate that the particular patient is unable to correctly undergo the vision testing and sending the pause command to the Visual Test Unit for the particular patient to control the Visual Test Unit to pause the vision testing.

In at least one embodiment, each of the Visual Test Units comprises a Control Unit and a Head Mounted Unit that is physically separate from the Control Unit and communicatively coupled to the Control Unit, wherein the Head Mounted Unit is worn on a head of the corresponding patient and the method further comprises using the Head Mounted Unit to generate visual stimuli that are presented to the patient during vision testing under the control of the Control Unit.

In at least one embodiment, the Head Mounted Unit comprises a position sensor for obtaining head movement data for the patient during vision testing and the method comprises pausing vision testing when the head movement data indicates that a tilt in the position of the head of the patient head is greater than a pre-determined head tilt threshold with respect to a normal position or absolute vertical for longer than a predetermined head tilt deviation time.

In at least one embodiment, one of the Control Units is a Master Control Unit and the method further comprises storing vision test data for the vision tests conducted by all of the Control Units on memory of the Master Control Unit.

Apparatus for a Visual Field Test

In another aspect, in accordance with the teachings herein, there is provided an apparatus for a Visual Test Unit for performing vision testing on a patient, wherein the Visual Test Unit comprises: a Head Mounted Unit having: a Shell for providing a housing for electrical and optical components of the Head Mounted Unit, the Shell being worn on the head of the patient; an optical system comprising two Test Displays for generating the visual stimuli and optical elements that are optically coupled to the two Test Displays for receiving the generated visual stimuli and presenting the visual stimuli to at least one of the eyes of the patient during vision testing; light sources that are positioned to illuminate the eyes of the patient during vision testing; eye tracking cameras that are positioned for obtaining video images of the eyes of the patient; memory for storing computer instructions for a firmware software system; and a processor that is operatively coupled to the memory for executing the firmware software system for driving the two Test Displays to generate the visual stimuli; and a Control Unit that is physically separate from and communicatively coupled to the Head Mounted Unit, the Control Unit having: a power supply unit that is configured to provide power to various components of the Control Unit and the Head Mounted Unit; video capture electronics for receiving the video images generated by the eye tracking cameras of the Head Mounted Unit; eye movement measurement circuitry for analyzing the video images and generating gaze data indicative pupil positions during the eye movement in the video images; main memory for storing computer instructions for a visual test software system; and a main processor that is operatively coupled to the main memory for executing the computer instructions of the visual test software system for generating control signals that are sent to the processor of the Head Mounted Unit for generating the visual stimuli during the vision testing and analyzing the video images to determine vision test results, wherein electrical components are distributed between the Head Mounted Unit and the Control Unit so that the Head Mounted Unit is light weight and easier for the patient to wear.

In at least one embodiment, the Head Mounted Unit further comprises an adjustable harness arrangement that is attached to the Shell and when a position of the Head Mounted Unit is adjusted on the patient, the eye tracking cameras are configured to generate video images of the eyes of the patient and the main processor is configured to display the video images on a display screen along with an overlaid eye box representation where the display screen is located adjacent or near to the patient and viewable by a Technician to adjust the position of the Head Mounted Unit so that the pupils of the eyes of the patient are located within the overlaid eye box representation which indicates that the pupils of the eyes of the patient are aligned with the Test Displays and the eye tracking cameras, thereby allowing for more accurate vision testing to be performed, where the display screen is located adjacent or near to the patient.

In at least one embodiment, the display screen is a Control Unit Display that is located on a housing of the Control Unit or the display screen is physically separate from the Control Unit.

In at least one embodiment, the Head Mounted Unit further comprises: first and second Lens Stacks that each contain one or more optical elements that are part of the optical system; and an InterPupillary Distance (IPD) adjustment mechanism that includes: an IPD adjustment screw that is movingly coupled to both Lens Stacks; an IPD adjustment knob that is coupled to the IPD adjustment screw and is adjustable for turning the IPD adjustment screw which linearly moves the Lens Stacks towards one another or further apart from one another; and IPD adjustment viewpoints located on the Shell adjacent the Lens Stacks for viewing an amount of IPD adjustment that is provided by turning the IPD adjustment knob, wherein the IPD adjustment mechanism is adjusted based on an IPD of the patient to aid in aligning the pupils of the eyes of the patient with the Test Displays and the eye tracking cameras.

In at least one embodiment, the Head Mounted Unit further comprises: a spherical lens focus adjustment ring that is used to adjust a distance between certain optical elements of the optical system to provide spherical correction according to a corrective prescription for the patient; a spherical lens focus scale that indicates the spherical correction provided by adjustment of the spherical lens focus adjustment ring; and a lens focus scale view point that allows the spherical lens focus scale to be viewed. Alternatively, in at least one embodiment, spherical correction is achieved by altering the Cylinder Correction Lens Mount so that it will accept both cylinder correction lenses and spherical correction lenses. A spherical correction lens is selected to correct for the spherical error of the patient.

In at least one embodiment, the Head Mounted Unit further comprises: a cylindrical correction lens mount that is part of the optical system; and a cylindrical correction lens that is removably inserted in the Cylindrical Correction Lens Mount, the cylindrical correction lens being selected to correct an amount of cylindrical refractive error for the patient.

In at least one embodiment, the Head Mounted Unit comprises a light sensor that is adjacent to a given Test Display for generating a light data signal for measuring light intensity generated by the given Test Display, wherein the processor is configured to turn off the given Test Display when the measured light intensity is greater than a predetermined light intensity threshold.

In at least one embodiment, the Head Mounted Unit comprises a temperature sensor that is adjacent to the given Test Display for generating a temperature data signal for measuring temperature indicative of heat generated by the given Test Display, wherein the processor is configured to turn off the given Test Display when the measured temperature is greater than a predetermined temperature threshold.

In at least one embodiment, the Head Mounted Unit further comprises a position sensor for obtaining head movement data for the patient during vision testing and the main processor is configured to pause vision testing when the head movement data indicates that a tilt in the position of the head of the patient head is greater than a predetermined head tilt threshold with respect to a normal position or absolute vertical for longer than a predetermined head tilt deviation time.

In at least one embodiment, the Shell is made of a lightweight and durable material.

In at least one embodiment, the Head Mounted Unit further comprises goggles that are attached to the Shell, the goggles housing the optical and electrical components of the Head Mounted Unit and including eye pieces that are adjacent to the eyes of the patient and used to view the visual stimuli when the Head Mounted Unit is worn by the patient.

Method for Mounting Head Mounted Unit

In another aspect, in accordance with the teachings herein, there is provided a method for mounting apparatus for a Head Mounted Unit for performing vision testing on a patient, wherein the method comprises: generating video images of eyes of the patient when a position of the Head Mounted Unit is adjusted on the patient, where the Head Mounted Unit includes: a Shell for providing a housing for electrical and optical components of the Head Mounted Unit, the Shell being worn on the head of the patient; an adjustable harness arrangement that is attached to the Shell; an optical system comprising two Test Displays for generating the visual stimuli and optical elements that are optically coupled to the two Test Displays for receiving the generated visual stimuli and presenting the visual stimuli to at least one of the eyes of the patient during vision testing; light sources that illuminate the eyes during vision testing; and eye tracking cameras that are located in the Head Mounted Unit for obtaining the video images of the eyes of the patient; and displaying the video images on a display screen along with an overlaid eye box representation where the display screen is located adjacent or near to the patient and is viewable by a Technician as they adjust the position of the Head Mounted Unit and secure the Head Mounted Unit in place by adjusting the adjustable harness arrangement so that the pupils of the eyes of the patient are located within the overlaid eye box representation which indicates that the pupils of the eyes of the patient are aligned with the Test Displays and the eye tracking cameras, thereby allowing for more accurate vision testing to be performed.

In at least one embodiment, the method comprises showing the video images on a Control Unit Display that is operably coupled to and physically separate from the Head Mounted Unit or showing the video images on another display screen where the display screen is accessible by the Technician for viewing as the Technician adjusts the position of the Head Mounted Unit on the head of the patient.

In at least one embodiment, the Head Mounted Unit further comprises first and second Lens Stacks that each contain several optical elements that are part of the optical system; and an InterPupillary Distance (IPD) adjustment mechanism that is physically coupled to the first and second Lens Stacks for moving the first and second Lens Stacks, and the method further comprises: moving the Lens Stacks closer to one another or further away from one another based on a physical adjustment of the IPD adjustment mechanism; and displaying an amount of IPD adjustment via IPD adjustment viewpoints located on the Shell to provide a Technician with visual feedback for aligning the pupils of the eyes of the patient with the Test Displays and the eye tracking cameras based on an IPD of the eyes of the patient.

In at least one embodiment, the method further comprises: adjusting a distance between certain optical elements of the optical system in response to movement of a spherical lens focus adjustment ring by the Technician to provide spherical correction according to a corrective prescription for the patient; indicating the spherical correction provided by adjustment of the spherical lens focus adjustment ring via a spherical lens focus scale; and displaying the spherical lens focus scale via a lens focus scale view point to the Technician. Alternatively, in at least one embodiment, spherical correction is achieved by altering the Cylinder Correction Lens Mount so that it will accept both cylinder correction lenses and spherical correction lenses. A spherical correction lens is selected to correct for the spherical error of the patient.

In at least one embodiment, the method further comprises: providing a cylindrical correction lens mount as part of the optical system; and receiving a cylindrical correction lens that is removably inserted in the cylindrical correction lens mount, where the cylindrical correction lens is selected to correct an amount of cylindrical refractive error for the patient.

Further Apparatus for Visual Field Test

In another aspect, in accordance with the teachings herein, there is provided an apparatus for performing visual field testing on a patient using an Eye movement Test, wherein the apparatus comprises: a Test Display for generating visual stimuli that are presented to an eye of the patient during the visual field testing; an eye tracking camera that is directed to the eye of the patient for obtaining video images of the eye of the patient during the visual field testing; video capture electronics for receiving the video images of the eye of the patient; eye movement measurement circuitry for generating gaze data from the video images, the gaze data being indicative of changes in pupil position over time during eye movements made during the visual field testing; main memory for storing computer instructions for a visual test software system; and a main processor that is operatively coupled to the main memory, where the main processor, when executing the computer instructions of the visual test software system, is configured to: generate a first stimulus command signal for driving the Test Display to generate a first visual stimulus having a first position, a first size and a first intensity in a visual field of the eye of the patient; execute an Eye Movement Algorithm for analyzing the gaze data obtained during presentation of the first visual stimulus to identify whether an eye movement during presentation of the first visual stimulus was a Responsive Eye Movement; where the eye movement was a Responsive Eye Movement indicating that the patient saw the first visual stimulus and where there was no Responsive Eye Movement indicating that the patient did not see the first visual stimulus; and generate a second command signal for driving the Test Display to generate a second visual stimulus having a second position, a second size and a second intensity where the second position is equal to the first position, the second size is equal to the first size, the second intensity is less than the first intensity when the Responsive Eye Movement indicates that the patient saw the first stimulus and the second intensity is greater than the first intensity when there was no Responsive Eye Movement. That process is repeated for each location that is being tested in accordance with one of the Standard Tests until such time as the lowest luminosity is determined at which the patient saw the stimulus.

In at least one embodiment, the main processor is configured to generate the second command signal for driving the Test Display to generate the second visual stimulus to be the same as the first visual stimulus when the eye movement data indicates that the patient blinked during presentation of the first visual stimulus.

In at least one embodiment, the main processor is configured to carry out Fixation Monitoring by pausing the visual field testing when the gaze data indicates that the patient has lost central fixation and to restart the visual field testing when the gaze data indicates that the patient has regained central fixation.

In at least one embodiment, the apparatus further comprises a position sensor for obtaining head movement data for the patient during the visual field testing and the main processor is configured to pause vision testing when the head movement data indicates that a tilt in the position of the head of the patient head is greater than a pre-determined head tilt threshold for longer than a predetermined head tilt deviation time.

In at least one embodiment, eye movement measurements are obtained from the gaze data the eye movement measurements including: (a) an amplitude measurement which is a distance traveled by the eye from a central fixation point towards a position of the visual stimulus,), (b) an acceleration measurement which is the degree to which the eye movement increased in speed over the distance traveled, and (c) an eye movement direction measurement.

In at least one embodiment, the main processor is configured to determine that the eye movement is a Responsive Eye Movement when the eye movement occurs within a predetermined time window after the presentation of a light stimulus and where the eye movement meets or exceeds the minimum threshold for the acceleration of the eye movement and the eye movement meets or exceeds the minimum threshold for the amplitude of the eye movement and where, the eye movement is in the direction of the light stimulus, plus or minus a specified margin of error.

In at least one embodiment, the main processor is configured to determine that the eye movement is a Passive False Positive Event when the eye movement occurs within the Time Window and the eye movement meets or exceeds the minimum threshold for the acceleration of the eye movement but does not meet or exceed the threshold for the amplitude of the eye movement and/or is not within the margin of error for the direction of the eye movement.

In at least one embodiment, the main processor is configured to determine that an eye movement is an Active False Positive Event when the eye movement does not occur within the Time Window and meets or exceeds an acceleration rate determined by the Eye Movement Algorithm.

In at least one embodiment, the main processor is configured to identify a False Negative Event.

In at least one embodiment, the predefined acceleration threshold and the predefined amplitude threshold differ depending on location of presentation of the visual stimulus within the visual field.

In at least one embodiment, the main processor is configured to randomly vary when stimulus command signals are generated for driving the Test Display to generate subsequent visual stimuli at different random time intervals.

Further Method for Visual Field Test

In another aspect, in accordance with the teachings herein, there is provided a method for performing visual field testing on a patient using an Eye movement Test, wherein the apparatus comprises: a Test Display for generating visual stimuli that are presented to an eye of the patient during the visual field testing; an eye tracking camera that is directed to the eye of the patient for obtaining video images of the eye of the patient during the visual field testing; video capture electronics for receiving the video images of the eye of the patient; eye movement measurement circuitry for generating gaze data from the video images, the gaze data being indicative of changes in pupil position over time during eye movements made during the visual field testing; main memory for storing computer instructions for a visual test software system; and a main processor that is operatively coupled to the main memory, where the main processor, when executing the computer instructions of the visual test software system, is configured to: generate a first stimulus command signal for driving the Test Display to generate a first visual stimulus having a first position, a first size and a first intensity in a visual field of the eye of the patient; execute an Eye Movement Algorithm for analyzing the gaze data obtained during presentation of the first visual stimulus to identify whether an eye movement during presentation of the first visual stimulus was a Responsive Eye Movement; where the eye movement was a Responsive Eye Movement indicating that the patient saw the first visual stimulus and where there was no Responsive Eye Movement indicating that the patient did not see the first visual stimulus; and generate a second command signal for driving the Test Display to generate a second visual stimulus having a second position, a second size and a second intensity where the second position is equal to the first position, the second size is equal to the first size, the second intensity is less than the first intensity when the Responsive Eye Movement indicates that the patient saw the first stimulus and the second intensity is greater than the first intensity when there was no Responsive Eye Movement. That method is repeated for each location that is being tested in accordance with one of the Standard Tests until such time as the lowest luminosity is determined at which the patient saw the stimulus.

In at least one embodiment, the method comprises generating the second command signal for driving the Test Display for generating the second visual stimulus to be the same as the first visual stimulus when the eye movement data indicates that the patient blinked during presentation of the first visual stimulus.

In at least one embodiment, the method further comprises performing Fixation Monitoring by pausing the visual field testing when the gaze data indicates that the patient has lost central fixation and restarting the visual field testing when the gaze data indicates that the patient has regained central fixation.

In at least one embodiment, the method further comprises using a position sensor for obtaining head movement data for the patient during the visual field testing and pausing the vision testing when the head movement data indicates that a tilt in the position of the head of the patient head is greater than a pre-determined head tilt threshold for longer a pre-determined head tilt deviation time.

Further Apparatus for Visual Field Test

In another aspect, in accordance with the teachings herein, there is provided an apparatus for performing vision testing on a patient suing a Clicker Test, wherein the apparatus comprises: a Test Display for generating visual stimuli that are presented to an eye of the patient during the visual field testing; an eye tracking camera that is directed to the eye of the patient for obtaining video images of the eye of the patient during the visual field testing to determine the reliability of the test; video capture electronics for receiving the video images of the eye of the patient; eye movement measurement circuitry for generating gaze data from the video images, the gaze data being indicative of changes in pupil position over time during eye movements made during the visual field testing; a clicker that generates a clicker event signal when the patient depresses the clicker; main memory for storing computer instructions for a visual test software system; and a main processor that is operatively coupled to the main memory, where the main processor, when executing the computer instructions of the visual test software system, is configured to: perform a Clicker Test comprising: generating a first stimulus command signal for driving the Test Display to generate a first visual stimulus having a first position, a first size and a first intensity in a visual field of the eye of the patient; and generating a second command signal for driving the Test Display to generate a second visual stimulus having a second position, a second size and a second intensity where the second position is equal to the first position, the second size is equal to the first size, the second intensity is less than the first intensity when the patient indicated recognition of the stimulus by depressing the Clicker button within a specified time window after presentation of the stimulus and the second intensity is greater than the first intensity when the patient did not depress the Clicker button within the specified time window after presentation of the stimulus.

In at least one embodiment, the main processor is configured to carry out Fixation Monitoring throughout the Clicker Test.

In at least one embodiment, a Clicker test may be performed or, alternatively, an Eye Movement Test.

Further Method for Visual Field Test

In another aspect, in accordance with the teachings herein, there is provided a method for performing vision testing on a patient suing a Clicker Test, wherein the apparatus comprises: a Test Display for generating visual stimuli that are presented to an eye of the patient during the visual field testing; an eye tracking camera that is directed to the eye of the patient for obtaining video images of the eye of the patient during the visual field testing to determine the reliability of the test; video capture electronics for receiving the video images of the eye of the patient; eye movement measurement circuitry for generating gaze data from the video images, the gaze data being indicative of changes in pupil position over time during eye movements made during the visual field testing; a clicker that generates a clicker event signal when the patient depresses the clicker; main memory for storing computer instructions for a visual test software system; and a main processor that is operatively coupled to the main memory, where the main processor, when executing the computer instructions of the visual test software system, is configured to: perform a Clicker Test comprising: generating a first stimulus command signal for driving the Test Display to generate a first visual stimulus having a first position, a first size and a first intensity in a visual field of the eye of the patient; and generating a second command signal for driving the Test Display to generate a second visual stimulus having a second position, a second size and a second intensity where the second position is equal to the first position, the second size is equal to the first size, the second intensity is less than the first intensity when the patient indicated recognition of the stimulus by depressing the Clicker button within a specified time window after presentation of the stimulus and the second intensity is greater than the first intensity when the patient did not depress the Clicker button within the specified time window after presentation of the stimulus.

In at least one embodiment, the main processor is configured to carry out Fixation Monitoring throughout the Clicker Test.

In at least one embodiment, a Clicker Test may be performed or, alternatively, an Eye Movement Test.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein. All of the illustrations are in accordance with the teachings herein.

FIGS. 13 through 18 illustrate various views of an example embodiment of Cylindrical Correction Lenses that are used with the HMU and how they may be attached to the back of the Lens Stack using the Cylindrical Correction Lens Mount.

Figure 1:
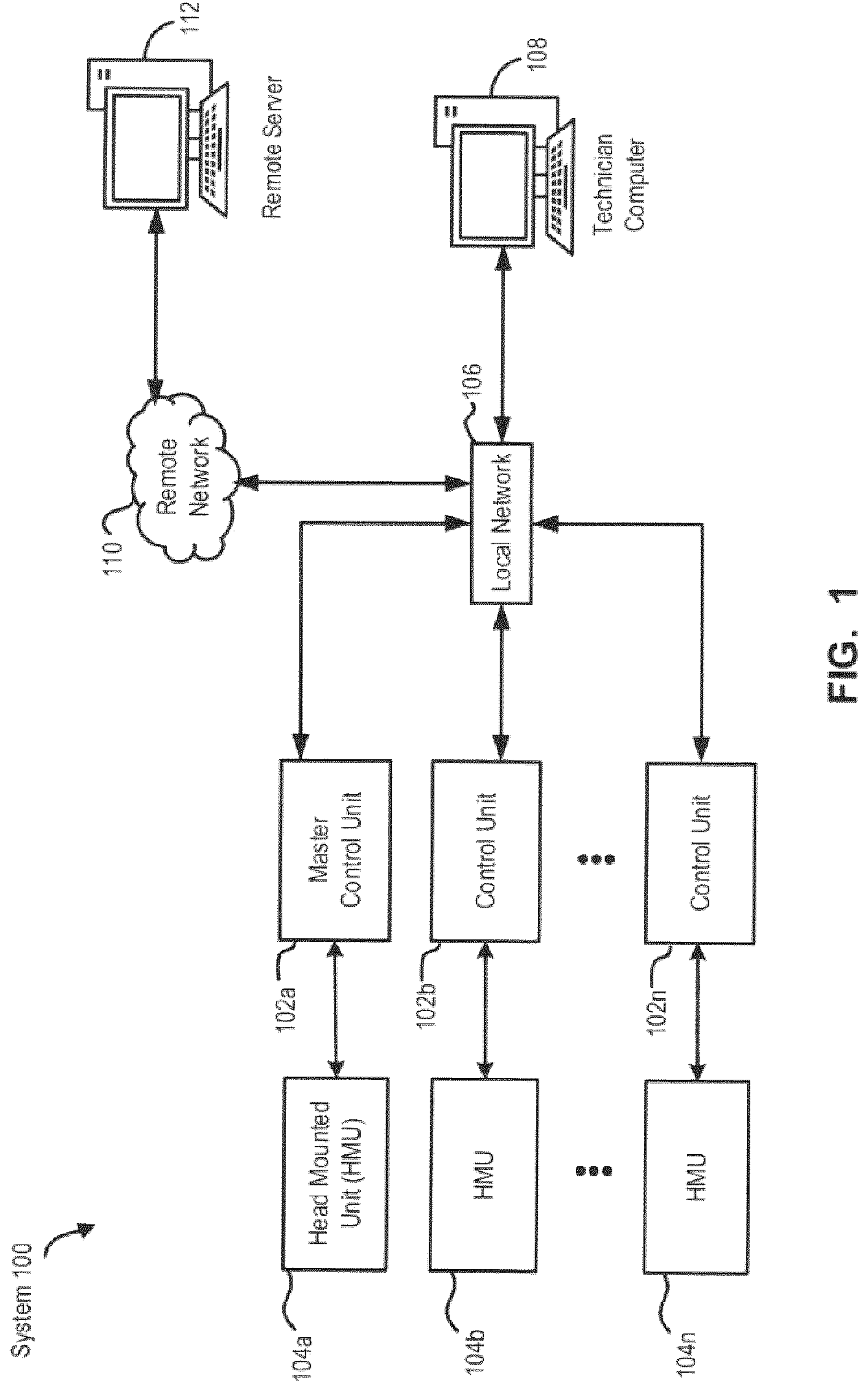
FIG. 1 illustrates an example embodiment showing the manner in which several Control Units (CUs) and Head Mounted Units (HMUs) are used to conduct vision tests simultaneously or separately, where the vision tests may be viewed using a Technician Computer and test data can be stored in a remote location over a network.

Further aspects and features of the example embodiments described herein will appear from the following description taken together with the accompanying drawings.

In the drawings, like characters of reference indicate corresponding parts in the different figures.

DRAFTING AND INTERPRETIVE PROVISIONS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the example embodiments described herein.

The terms "light stimulus" and "stimulus" are used interchangeably and mean the same thing.

It should also be noted that the terms "coupled" or "coupling" as used herein can have several different meanings depending on the context in which these terms are used. For example, the terms coupled or coupling can have a mechanical, optical or electrical connotation. For example, as used herein, the terms coupled or coupling can indicate that two elements or devices can be directly connected to one another or connected to one another through one or more intermediate elements or devices via an electrical or optical signal, an electrical connection, an electrical element, an optical element or a mechanical element depending on the particular context. Furthermore, coupled electrical elements may send and/or receive data.

Unless the context requires otherwise, throughout the specification and claims which follow, the word "comprise" and variations thereof, such as, "comprises" and "comprising" are to be construed in an open, inclusive sense, that is, as "including, but not limited to".

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable manner in one or more embodiments, unless otherwise specified to be not combinable or to be alternative options.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

The headings and Abstract of the Disclosure provided herein are for convenience only and do not interpret the scope or meaning of the embodiments.

Similarly, throughout this specification and the appended claims the term "communicative" as in "communicative pathway," "communicative coupling," and in variants such as "communicatively coupled," is generally used to refer to any engineered arrangement for transferring and/or exchanging information. Examples of communicative pathways include, but are not limited to, electrically conductive pathways (e.g., electrically conductive wires, electrically conductive traces), magnetic pathways (e.g., magnetic media), optical pathways (e.g., optical fiber), electromagnetically radiative pathways (e.g., radio waves), or any combination thereof. Examples of communicative couplings include, but are not limited to, electrical couplings, magnetic couplings, optical couplings, radio couplings, or any combination thereof.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

At least a portion of the example embodiments of the apparatuses or methods described in accordance with the teachings herein may be implemented as a combination of hardware or software. For example, a portion of the embodiments described herein may be implemented, at least in part, by using one or more computer programs, executing on one or more programmable devices comprising at least one processing element, and at least one data storage element (including volatile and non-volatile memory). In some cases, these devices may also have at least one input device (e.g., a touchscreen, buttons, dials, sliders and the like) and at least one output device (e.g., a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in JAVA, C, C++ or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media (e.g., a computer readable medium such as, but not limited to, ROM, flash memory, magnetic disk, optical disc) or a device that is readable by a programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, DVD's, tapes, chips, and magnetic, optical and electronic storage. In at least one alternative embodiment, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

Defined Terms

Throughout this disclosure various words and phrases are defined. The following terms shall bear the following meanings as used in the Detailed Description section:

The term "Head Mounted Unit" or "HMU" means an apparatus with associated software for a head-mounted unit as described herein.

Figure 3A:
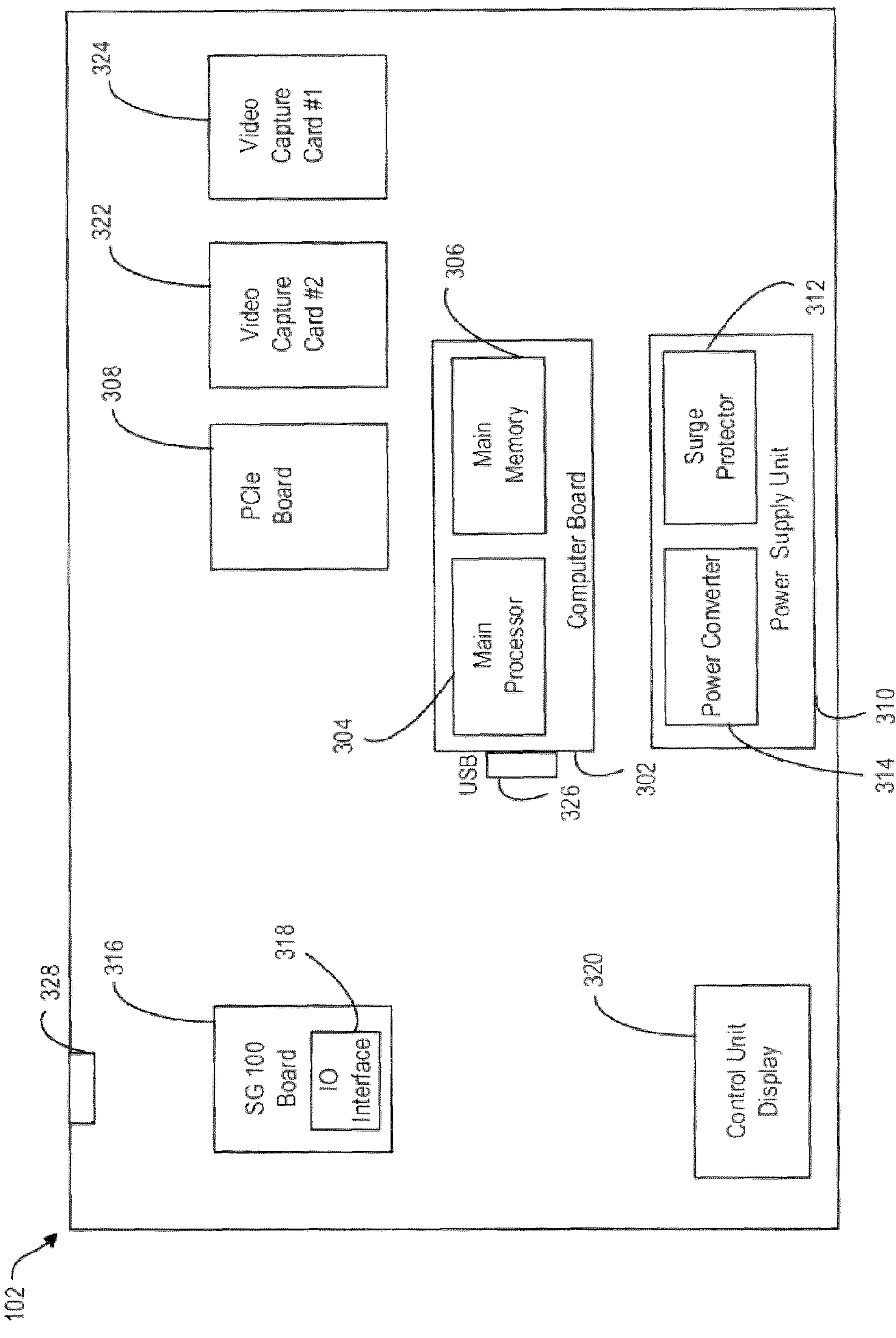
FIG. 3A illustrates an example embodiment of the electrical components of a CU.
Figure 3B:
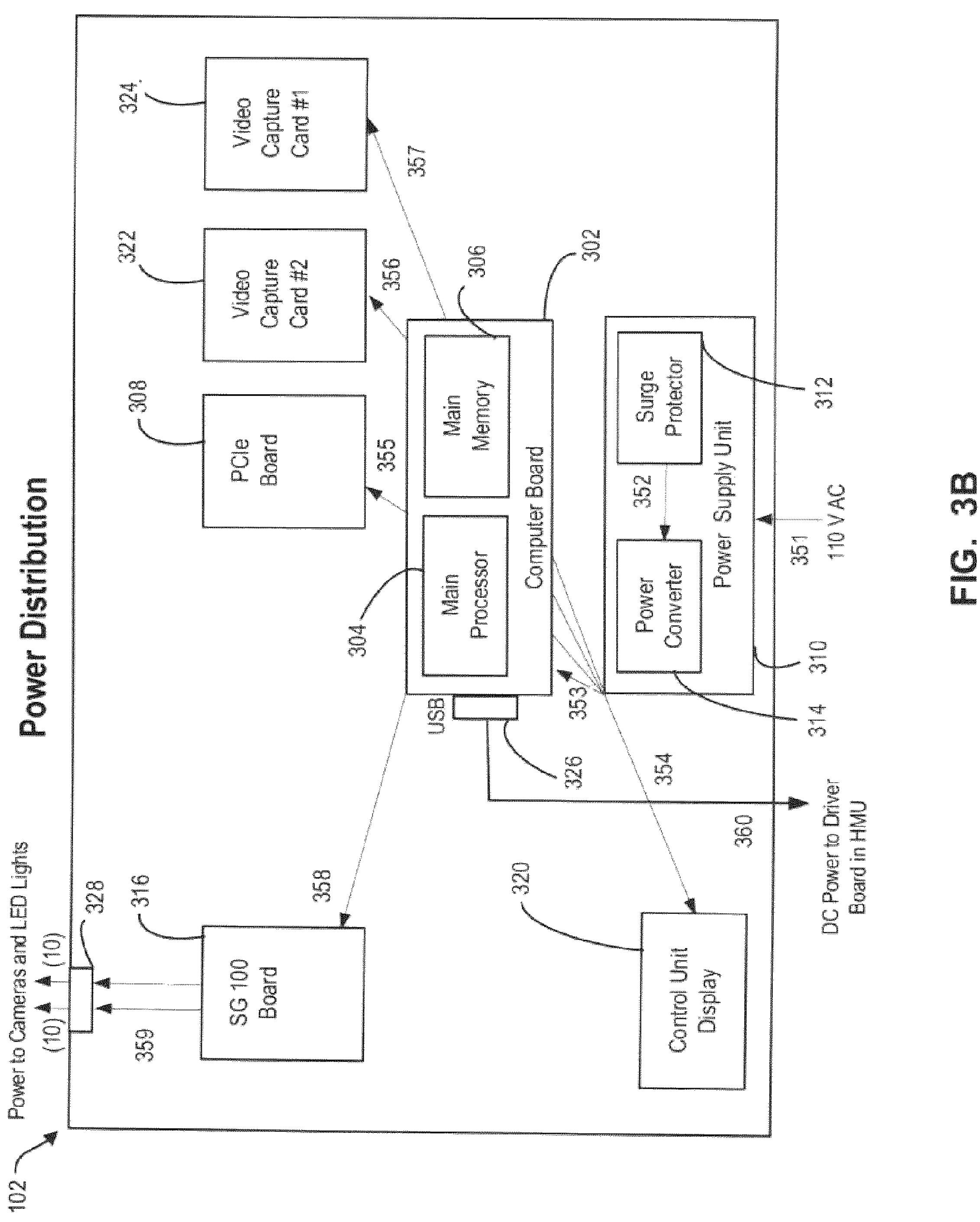
FIG. 3B illustrates power flow through the electrical components of the CU of FIG. 3A.
Figure 3C:
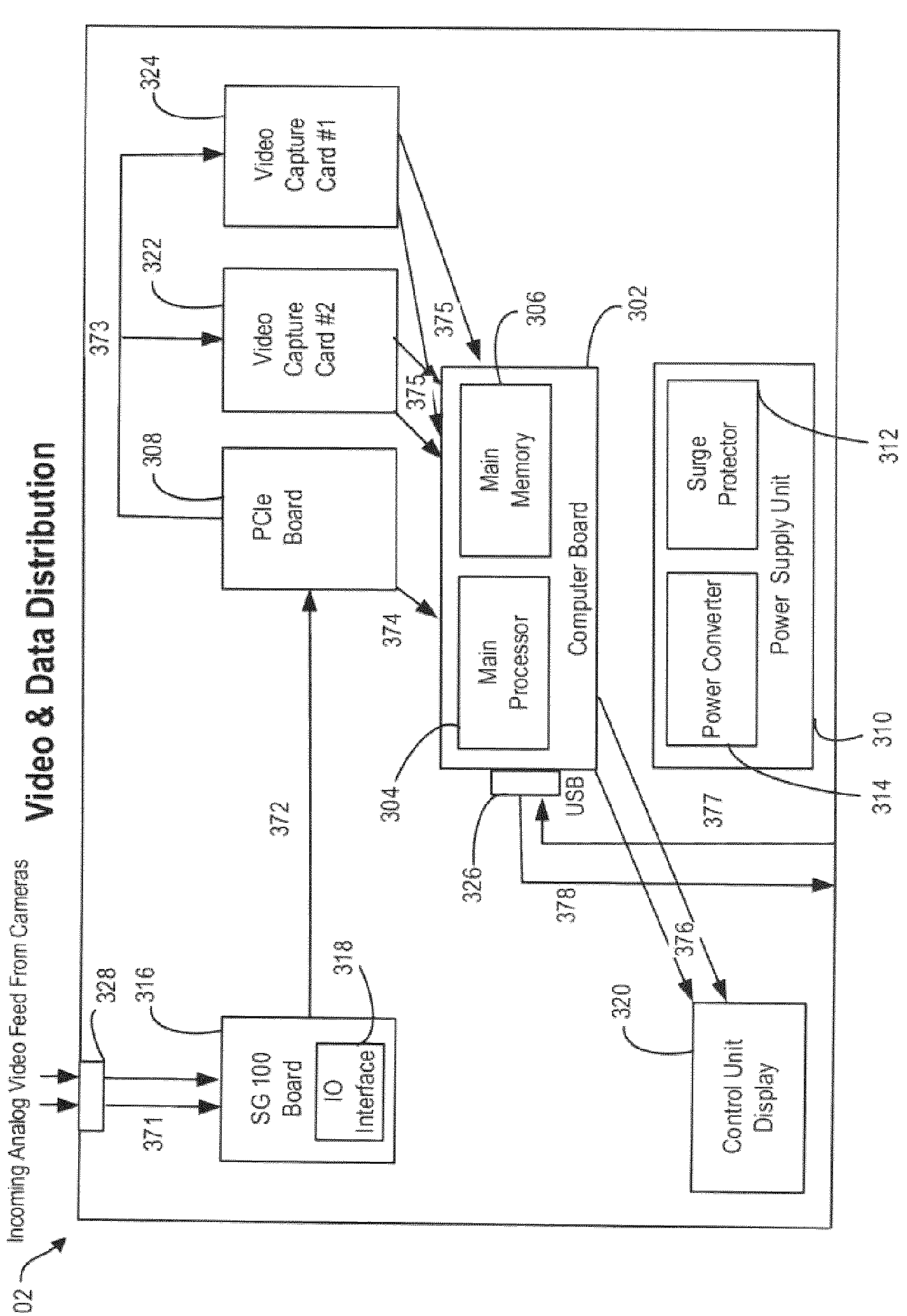
FIG. 3C illustrates data flow through the electrical components of the CU of FIG. 3A.
Figure 4:
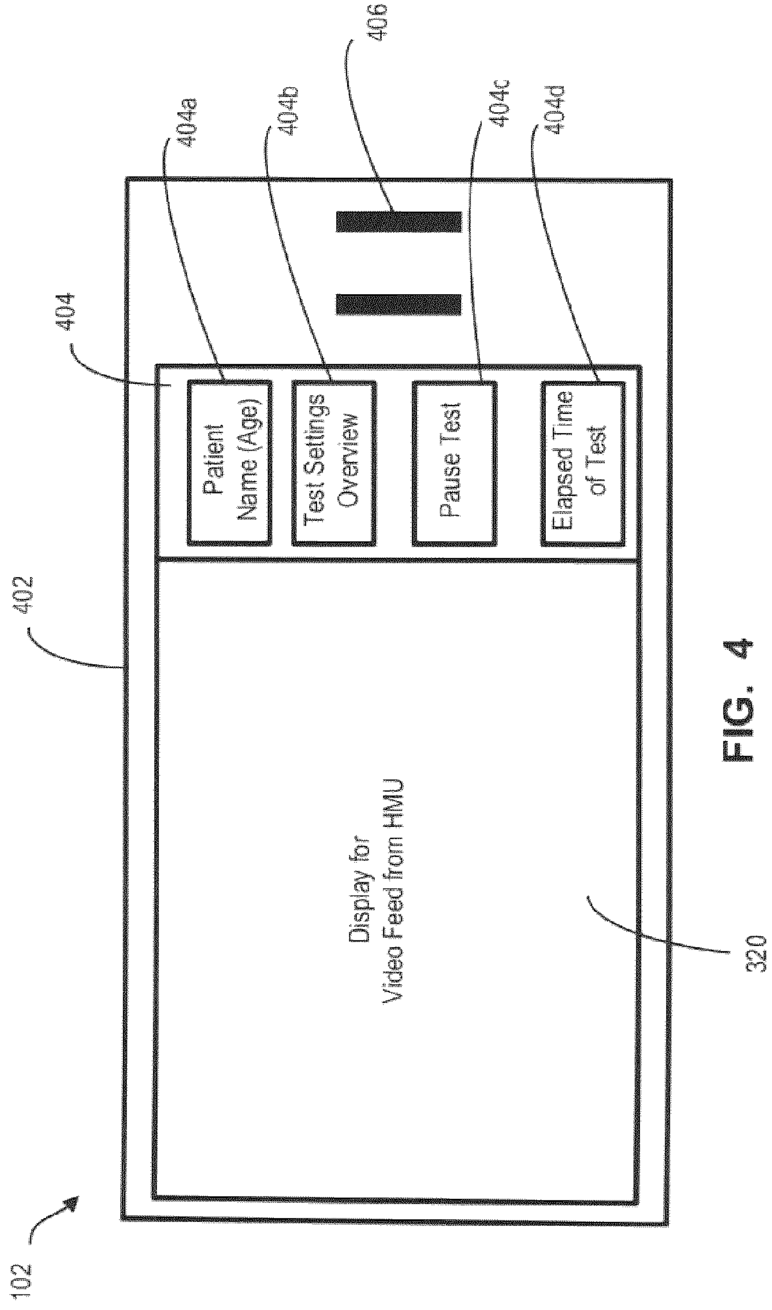
FIG. 4 illustrates an example embodiment of the exterior of a CU showing the CU Display and controls.

The term "Control Unit" or "CU" means an apparatus in the form of a box or a container containing various electrical components as illustrated in FIGS. 3A-3C with a display mounted on the front of the Control Unit as illustrated in FIG. 4 or alternatively, without a display, which operate with software to control the HMU.

The term "Visual Test Unit" means apparatus comprising an HMU and a CU tethered or linked together comprising hardware and software for performing certain functions described herein.

The term "Control Unit Display" or "CU Display" means a display on the front of the CU as illustrated in FIG. 4 or alternatively, mounted independently of the CU.

The term "CU Interface" means a user interface that is on the front of the CU Display and might be provided as a Graphical User Interface that can accept commands from a Technician through touch on the CU Display when the CU Display is touch sensitive screen or can include at least one physical button beside the CU display. The CU Interface allows a Technician to perform certain actions.

The term "Fixation Monitoring" means that apparatus, process and method executed by the Eye Tracking Algorithm whereby the gaze of the patient is monitored and a stimulus is not presented unless the patient is fixated on the central fixation point.

The term "Clicker Test" means a visual field test conducted using a Visual Test Unit wherein the patient is presented with a central fixation point indicated by way of a cross or other icon in the middle of the visual field presented. The patient is instructed to remain fixated on such central fixation point throughout the test. Light stimuli are then presented of various intensities at each coordinate of the visual field eccentric to the central fixation point that is to be tested. When the patient sees a light stimulus, he or she depresses the button or clicker to indicate that the stimulus has been seen. Light stimuli are then presented at higher or lower levels of luminosity until the threshold level is determined.

The term "Eye Movement Test" means a visual field test conducted using a Visual Test Unit wherein the patient is presented with a central fixation point indicated by way of a cross or other icon in the middle of the visual field presented. The patient is instructed to start by fixating on the central fixation point but, when a light stimulus is presented at a different location, to direct their gaze towards the light stimulus. The patient is further instructed to then return their fixation to the central fixation point. Recognition of light stimuli is determined by Eye Tracking Cameras that records the patient's eye movements and an Eye Movement Algorithm that determines which of the patient's eye movements represent Responsive Eye Movements and which of the patient's eye movements or lack of eye movements represent Non-Responsive Events. If the patient is not properly fixated prior to the presentation of a light stimulus, the light stimulus will not be presented until the patient has gained or re-gained fixation on the central fixation point. When a stimulus is presented the Eye Tracking Algorithm will determine whether or not there has been a Responsive Eye Movement. When there has been a Responsive Eye Movement, indicating that the patient saw the stimulus, then subsequent light stimulus at that location will be presented at a lower luminosity until such time as the patient is unable to see the stimulus. Conversely, when the patient did not respond to a light stimulus with a Responsive Eye Movement indicating that the patient did not see the light stimulus then subsequent light stimulus at that location will be presented at higher luminosity until such time as the patient is able to see the light stimulus. In this manner the threshold level of recognition is determined for each location tested.

The term "Time Window" means a predetermined period of time after the presentation of a stimulus.

The term "Responsive Eye Movement" means an eye movement that occurs during an Eye movement Test that occurs within the Time Window, meets or exceeds the minimum threshold for acceleration of the eye movement, that meets or exceeds the minimum threshold for the amplitude of the eye movement and is within the margin of error for the direction of the eye movement in the direction of the stimulus and is thus determined to be an eye movement that indicates that the patient saw the stimulus.

The term "Passive False Positive Event" means an eye movement that occurs during an Eye Movement Test, that occurs within the Time Window and meets or exceeds the threshold for the acceleration of the eye movement but does not meet or exceed the threshold for the amplitude of the eye movement and/or is not within the margin of error for the direction of the eye movement towards the stimulus.

The term "Active False Positive Event" means an eye movement that occurs during an Eye Movement Test that does not occur within the Time Window and meets or exceeds an acceleration rate determined by the Eye Movement Algorithm.

The term "False Negative Event" means that situation occurring during an Eye Movement Test where a stimulus is presented to which the patient does not respond with a Responsive Eye Movement even though when a stimulus of the same size and at the same location and of lower intensity had been presented previously in the test, the patient had responded to with a Responsive Eye Movement.

The term "Non-Responsive Event" means a Passive False Positive Event, an Active False Positive Event or a False Negative Event.

The term "Eye Movement Algorithm" means a software algorithm forming part of the Visual Test software system described herein that performs various functions including the following. It determines if the patient is fixated on the central fixation point and does not send a signal to prompt the presentation of a stimulus until such time as the patient has gained or re-gained fixation on the central fixation point. If an Eye Movement Test is being conducted, it identifies and tracks Responsive Eye Movements and Non-Responsive Events.

The term "False Positive Error" means a situation where a patient, undertaking a Clicker Test, depresses the clicker button when a stimulus has not been presented or a stimulus has been presented that is not a supra-threshold stimulus and the patient has depressed the clicker button.

The term "False Negative Error" means a situation where a patient, undertaking a Clicker Test, fails to depress the clicker button when the patient is presented with a stimulus of greater intensity but of the same size and at the same location as a stimulus presented earlier in the test to which the patient responded by depressing the clicker button.

Figure 2:
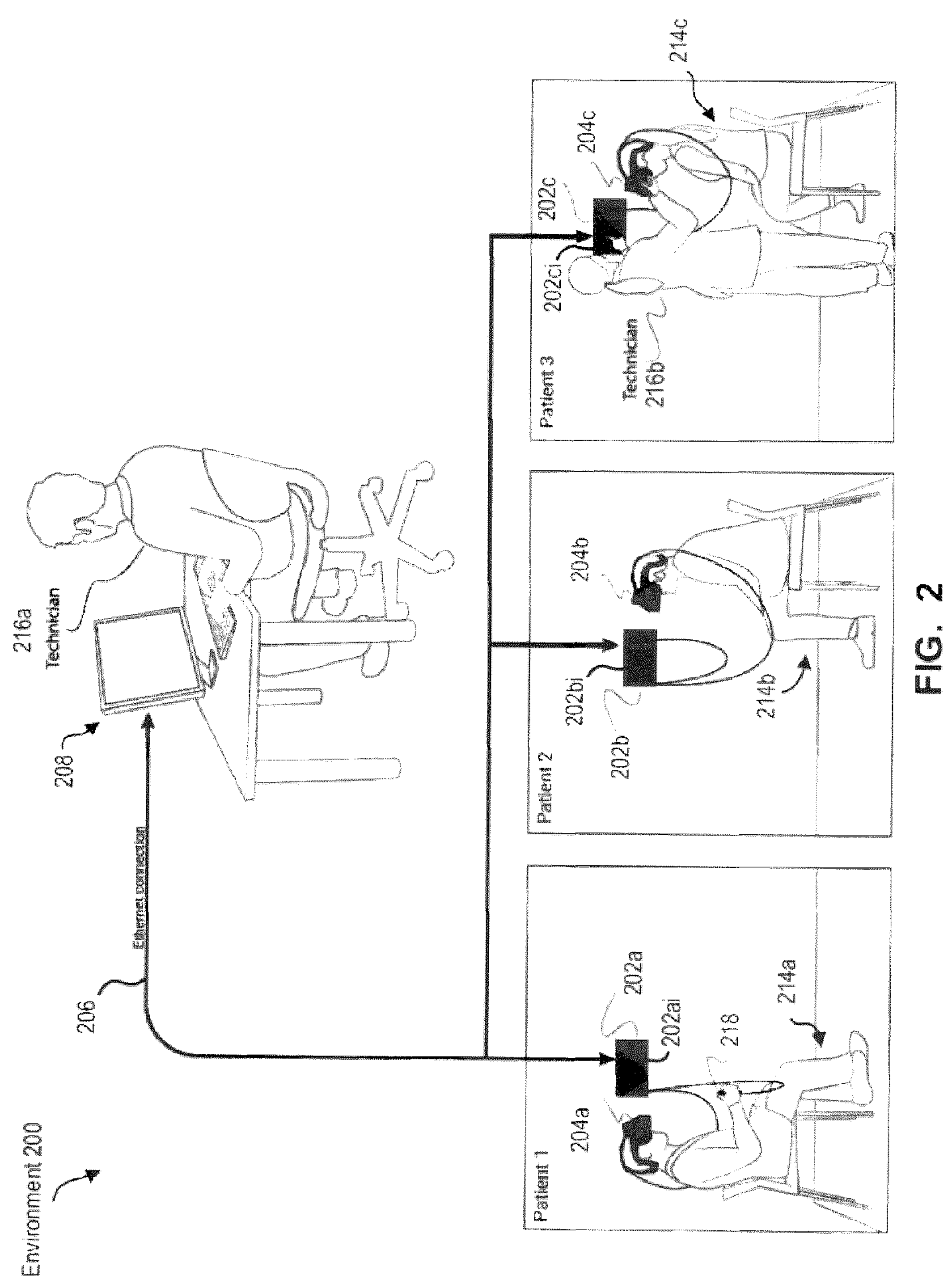
FIG. 2 illustrates, in graphic form, an example of the manner in which several CUs and HMUs can be used to conduct vision tests simultaneously or separately and may be viewed from a Technician Computer.

The term "Technician Computer" means a computer, tablet or similar device that is used by a Technician who is administering the vision test as illustrated in FIG. 2.

The term "Technician" means a trained person administering the vision test as shown in FIG. 2.

Figures 8, 9, 10:
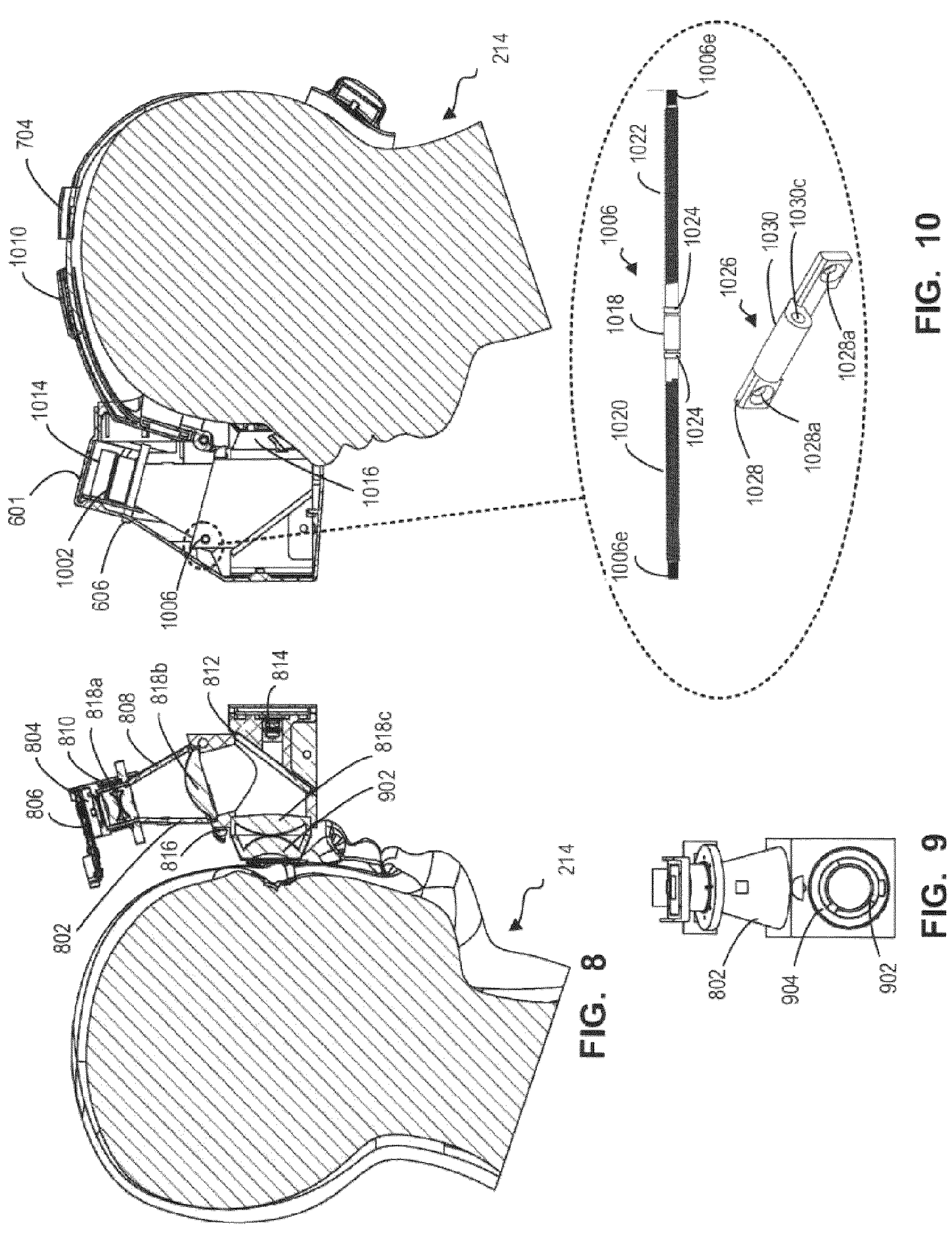
FIG. 8 illustrates a cross sectional view of the HMU of FIGS. 6 and 7 taken along sectional line 8-8 shown in FIG. 6.
FIG. 9 illustrates a rear elevation view of an example embodiment of the exterior of a Lens Stack of the HMU showing a Cylindrical Correction Lens Mount on the front of the Lens Stack.
FIG. 10 illustrates a cross-sectional view of the HMU of FIGS. 6 and 7 taken along sectional line 10-10 shown in FIG. 6.
Figure 12:
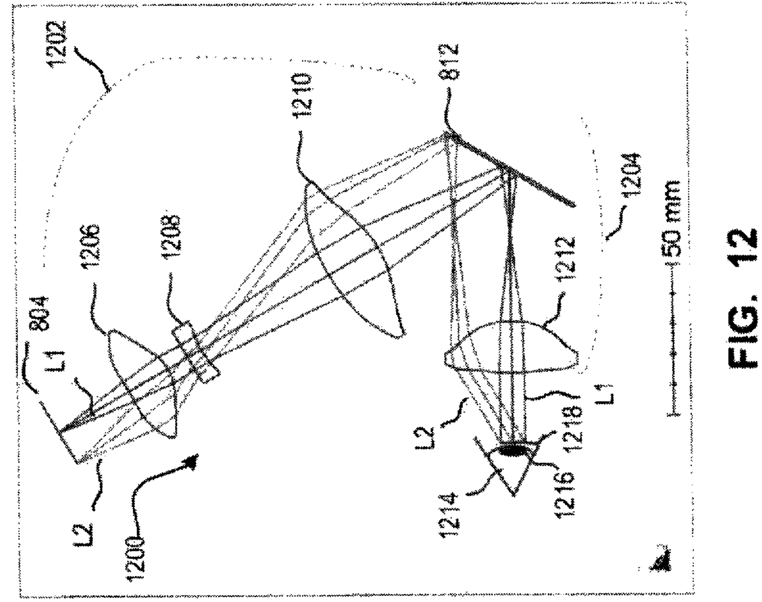
FIG. 12 illustrates an example embodiment of a schematic of a Lens Stack showing the effect on the disbursement of light along different regions of the light spectrum through the lenses of the Lens Stack in order to provide an image that is spatially located in an Eye Box of a particular diameter at the patient's eyes.

The term "Lens Stack" means several lenses arranged and other optical components that are housed in a Lens Stack Housing as illustrated in FIGS. 9-10 and 12.

Figures 6, 7:
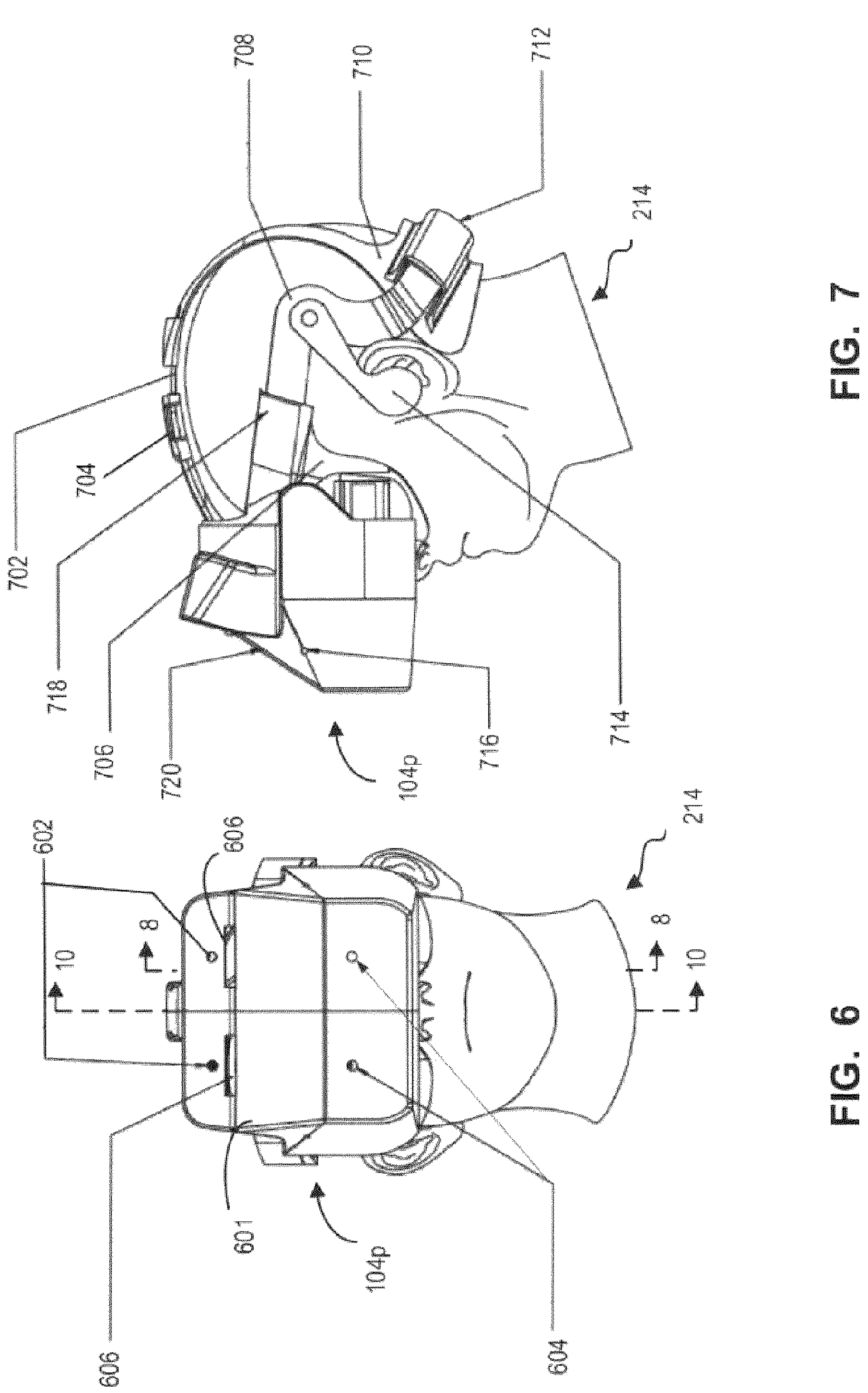
FIGS. 6 and 7 illustrate front and side elevation views of an example embodiment of the exterior of an HMU.
Figure 11:
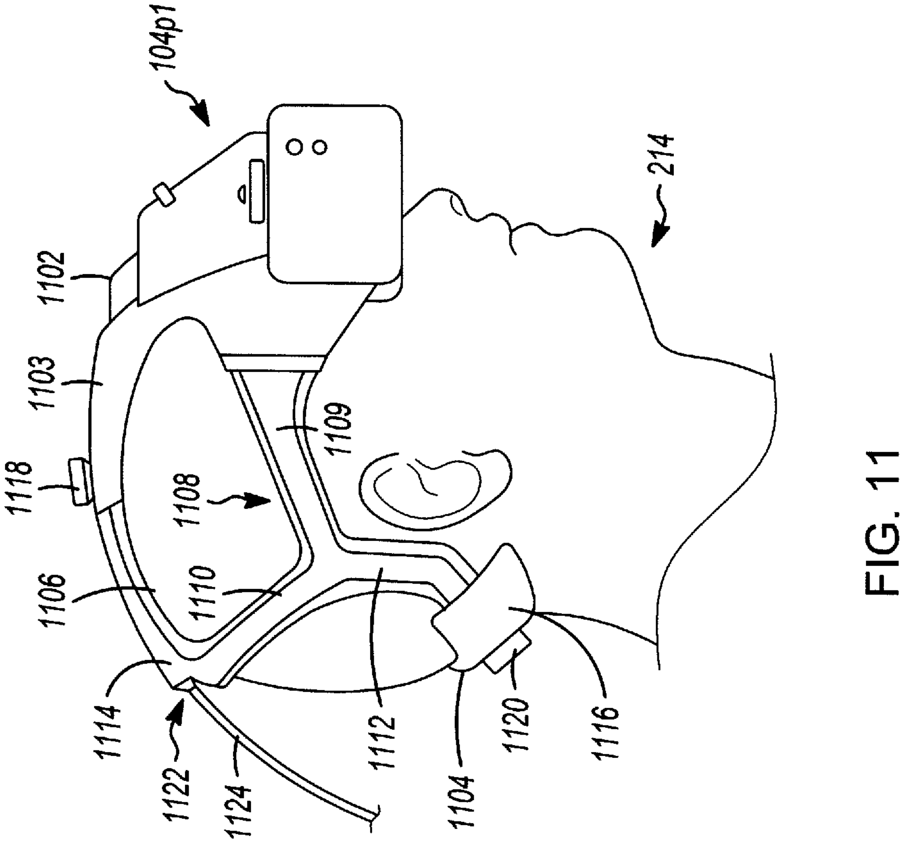
FIG. 11 illustrates a side view of another example embodiment of the exterior Shell of an HMU.

The term "Shell" means the plastic or similar material that encloses and provides a protective housing for the Lens Stack Housing and other parts of the HMU as illustrated in FIGS. 7, 8 and 11, for example.

The term "Eye Box" as used herein means a physical area that light from a light stimulus strikes a patient's eye such that when the pupil of the patient's eye is within the Eye Box, the optical system will reliably produce the expected stimulus properties including light stimulus size, shape and luminance.

The term "Cylindrical Correction Lens Mount" means a mechanism, an example of which is illustrated in FIGS. 13-18, that is used to attach and hold different corrective lenses in the HMU, an example of which is illustrated in FIG. 8.

The term "Test Display" means a micro-display or array that presents stimuli to the patient by illuminating pixels and where the light produced is projected through the optical system to the patient's eyes. In at least one embodiment, the Test Display may be back lit to increase its luminosity. In another embodiment the Test Display will consist of an LED board with screen in front with holes in it corresponding to the location of the stimuli to be presented in accordance with the Standard Tests plus four holes corresponding to the location of stimuli used for calibration purposes and one hole for the central fixation point. The LED board and screen may be configured to present stimuli of one or more of the Goldman sizes.

The term "Eye Tracking Camera" means infrared cameras that are mounted in the HMU.

The term "Master Control Unit" means a particular CU that is designated to store test data for all Control Units that are linked as illustrated in FIG. 1.

The term "Standard Test" means a standard vision test that may be performed such as, but not limited to, a visual field test including a 10-1, 10-2, 24-1, 224-2, 30-1 or 30-2 visual field tests.

DETAILED DESCRIPTION OF VARIOUS EMBODIMENTS

The various example embodiments that are herein described address at least one of the issues with the Conventional Gold Standard Devices discussed previously. For example, these embodiments address at least one of the issues of inaccuracy and unreliability, patient discomfort and the inefficient manner in which visual field tests are conventionally administered.

For example, in one aspect, in at least one embodiment described in accordance with the teachings herein, the issue of inaccuracy and unreliability of conventional visual eye test results are addressed by providing a method for conducting the visual field test by way of an Eye Movement Test which incorporates an Eye Movement Algorithm which performs a number of functions including: (a) determines whether or not the patient is fixated on the central fixation point before sending a signal to present a stimulus; (b) determines whether or not a Responsive Eye Movement has occurred in response to the presentation of a stimulus; (c) determines whether or not a Passive False Positive Event has occurred; (d) determines whether or not an Active False Positive Event has occurred; and (e) determines whether or not a False Negative Event has occurred.

In another aspect, in at least one embodiment described in accordance with the teachings herein, the issue of patient discomfort is addressed by conducting the visual field test by way of an Eye Movement Test using an HMU that: (a) does not require the patient to depress a button or clicker to signal recognition of light stimuli; (b) does not require the patient to continuously maintain fixation on a central fixation point throughout the visual field test; and (c) does not require the patient to keep their head still throughout the test.

In another aspect, in at least one embodiment described in accordance with the teachings herein, the issue of the inefficiency of administering conventional visual field tests, which leads to relatively higher costs, is addressed by providing a method as described herein whereby the tests do not have to be conducted in a room where the ambient light must be controlled as the visual light stimuli are provided using an HMU and furthermore multiple tests can be conducted on multiple patients simultaneously by using multiple Visual Test Units that may be monitored from a central location by a single Technician.

In another aspect, in at least one embodiment described in accordance with the teachings herein, a clinical report of the test results may be produced in a similar manner as test results produced by Conventional Gold Standard Devices. For example, the test results may include measurements of the sensitivity of the patient's vision at specified locations eccentric to a central fixation point in accordance with the standardized tests referred to above by determining the lowest brightness at which the patient is able to see a visual stimulus at each specified location or coordinate in the visual field. In this respect, reports for the Clicker Test and the Eye Movement Test provide the same data. Advantageously, reports for Eye Movement Tests conducted by at least one embodiment described herein are similar in format to conventional test reports so that clinicians can compare test reports of Eye Movement Tests with earlier test reports conducted on the Conventional Gold Standard Devices in order to make meaningful comparisons between these two test reports and determine the progression of a visual disease, such as glaucoma.

In order to address the above-noted issues, one or more of the following features may be used separately or in combination with one another in at least one embodiments of the present teachings where the features are as set out hereafter.

(a) In one aspect, a system comprising hardware and software is provided to determine if the patient is fixated on the central fixation point before presenting a stimulus. Without such a mechanism or process it will not be possible to prevent fixation errors.

(b) In one aspect, a system comprising hardware and software is provided to determine whether or not there was a Responsive Eye Movement in response to a light stimulus. Without a mechanism or process for properly making that determination it will not be possible to use an Eye Movement Test to provide visual field test results to a standard that has increased reliability and accuracy compared to Conventional Gold Standard Devices and is otherwise acceptable in a clinical setting.

(c) In one aspect, a system comprising software and hardware is provided to identify and track Passive False Positive Events, Active False Positive Events and False Negative Events. Without such a mechanism and process it will not be possible to assess the reliability of the test conducted.

(d) In another aspect, an optical system is provided for generating light stimuli on Test Displays where the light stimuli are seen by the patient via a Lens Stack without excessive aberration such that the light stimuli are presented in an Eye Box which may be between about 8 mm and about 12 mm and have a minimum brightness at the patient's eyes of not less than about 3,200 Nts. Light stimuli will appear distended in shape and appear larger if they are presented outside of the Eye Box particularly towards the perimeter of the patient's visual field. It is important that such distortions are kept generally within acceptable limits in order to avoid inaccurate test results. The diameter of patients' pupils in their normal state, i.e. not dilated or contracted, will vary on average between 3 and 4 mm. If the patient's pupils are dilated, as is often the case in a clinical setting, the pupils may have a diameter of as much as about 10 mm. It is therefore important that the light stimuli be presented in an Eye Box that is generated by the optical system to be not less than 8 mm. In order to generate the same dynamic range of light stimuli as the Conventional Gold Standard Devices the brightness of the light stimuli at the patient's eyes must be not less than about 3,200 Nts. Depending on the implementation, the Test Displays may have a brightness significantly greater than about 3,200 Nts as the brightness will be reduced as the light passes through each optical element or lens in the optical system.

(e) In another aspect, one or more software systems are provided that collectively: (i) permit light stimuli to be presented; (ii) receive signals from the Eye Tracking Cameras in order to record the patient's eye movements during vision testing; (iii) determines whether or not the patient is fixated on the central fixation point before presenting a stimulus; (iv) tracks and determines whether or not Non-Responsive Events have occurred; (v) determines whether or not the patient has seen a light stimulus by determining whether or not there was a Responsive Eye Movement in response to a stimulus; (vi) determines the sequence of presentation of further visual stimuli of different intensities at predetermined locations; (vii) stores numerical test values representing the minimum light intensities for different light stimuli seen by the patient and then sends test values to a software system that will adjust the test values based on an aged based algorithm to generate test report data; and (viii) provides a user interface to allow a Technician to conduct a vision test, produce a test report for the clinician based on the test report data, and stores the test report and the test report data.

(f) In another aspect, a hardware design for separating hardware components between the HMU and the CU is provided in order to reduce the weight of the HMU. This is advantageous since keeping the weight of the HMU within acceptable levels is important in terms of patient comfort. This is achieved by placing most of the electrical components in the CU, placing electronic drivers, optical components and sensors in the HMU and using lightweight materials in the construction of the HMU.

(g) In another aspect, due to the relative diameters of patients' pupils and the size of the Eye Box and the test methodology including delivering the stimuli within the Eye Box, a method and associated hardware are provided that may be used to secure the HMU on the patient's head such that the patient's pupils accurately and precisely align with the Test Displays, Lens Stack and Eye Box so that the stimuli can be delivered within the Eye Box and such that the patient's pupils are in the field of view of the Eye Tracking Cameras so that the patient's eye movements can be properly recorded. This may be achieved by: (i) incorporating an adjustable head strap system with the HMU to hold the HMU securely in place during testing; (ii) incorporating infrared lights into the HMU to illuminate the area in front of the patient's eyes once the HMU is placed on the patient's head; (iii) using the Eye Tracking Cameras to deliver a video feed to on the CU Display to show the position of the patient's eyes relative to a representation of the Eye Box which indicates an alignment of the patient's eyes/pupils with the Test Displays and the Eye Tracking Cameras and; (iv) using an InterPupillary Distance (IPD) adjustment mechanism and the head strap adjustment mechanism as described below to properly secure the HMU to the patient's head to align the patient's eyes relative to the Test Displays and Eye Tracking Cameras.

(h) In another aspect, the HMU may include optical elements to correct for any spherical or cylindrical refractive errors of the patient.

(i) In another aspect, a method and associated hardware is provided to ensure that the patient keeps his or her head upright within 20 degrees of the vertical during vision testing. This may be achieved by incorporating a position sensor, such as a gyroscope or an accelerometer or similar sensor, in the HMU along with a method for pausing the vision test if the patient's head tilt exceeds 20 degrees. This is advantageous for increasing the accuracy of the test results.

(j) In another aspect, a method and system is provided to conduct multiple tests on multiple patients simultaneously. This is achieved by providing several Visual Test Units that each test a separate patient simultaneously. Each CU of the Visual Test Units includes a main processor and memory for storing the software systems and firmware used for communicating with and controlling operation of a corresponding HMU for performing a vision test. A Technician's Computer that is able to access each main processor in each Control Unit to monitor testing. In at least one embodiment, all CUs are linked to each other and the Technician's Computer.

Various embodiments will now be described which will include an overall embodiment, and alternatives thereof, of the mechanical components, electrical components, optical components and software components that, when used together in the manner described herein, can perform either a Clicker Test or an Eye Movement Test. In addition, it should be understood that some of the embodiments described herein correspond to sub-components of the overall system and method, which can be used individually or in combination with one another, in various other vision testing applications.

Overall System Hardware, Optical and Software Components

Referring now to FIG. 1, shown therein is a system 100 for performing vision testing. System 100 generally includes one or more Visual Test Units that each comprise a CU and an HMU. In this example, there are n Visual Testing Units each having one of CUs 102*a*-102*n* that is communicatively coupled with one of HMUs 104*a*-104*n*, where n is a positive integer greater than or equal to 1. The Visual Test Units can be used to conduct vision tests simultaneously or separately in time on up to n patients. The vision tests that can be conducted are described in further detail below.

The CUs 102*a*-102*n* are communicatively coupled to a local area network 106 so that they may each communicate with a Technician Computer 108 where a Technician (e.g., a medical practitioner) may initiate and monitor vision testing in real-time. The vision test data and associated vision test report data for a vision test may be stored on one of the CUs 102*a*-102*n* that was used to perform the vision test. The raw vision test data and the vision test report data may be viewable on the Technician Computer 108 by using the local network 106 to access the CU that was used to perform the vision test. The local network 106 may be implemented using an IEEE 802.3 (Ethernet), a wireless personal area network such as a Bluetooth™ network, a wireless local area network such as the IEEE 802.11 family of networks or other suitable communication technology.

The Technician Computer 108 can be any general purpose computer, such as a desktop computer, a laptop computer, a tablet computer or a smartphone capable of data communication. The Technician can use the Technician Computer 108 to access one of the CUs 102*a*-102*n* for setting up and performing a vision test as described in further detail below and receiving vision test data in real-time from the CUs 102*a*-102*n* that are being used to perform vision tests. For example, the Technician can access each of the CUs 102*a*-102*n* in use in order to monitor the tests being conducted (where the testing may overlap in time).

The Technician Computer 108 and the CUs 102*a*-102*n* may also communicate with a remote network 110 for storing vision test reports and vision test report data remotely, such as in the Cloud. For example, the remote network 110 may be coupled to a remote server 112, over the Cloud, that is used to maintain and update the software programs that are employed by the CUs 102*a*-102*n*, the HMUs 104*a*-104*n* and the Technician Computer 108. For example, in some embodiments, the test data can be uploaded to the Cloud and be used to create a new testing algorithm and the new testing algorithm can then be downloaded. The remote network 110 may be implemented in various ways such as, but not limited to, using the Internet, a cellular data network (e.g., 3G, LTE, 5G, etc.), or other suitable communication technology.

Referring now to FIG. 2, there is shown an illustrative example, in graphic form, of an example embodiment of an environment 200 for operating the system 100 of FIG. 1 in which corresponding elements of system 100 are shown with reference numerals increased by 100. In FIG. 2, multiple patients 214*a*-214*c* are concurrently administered visual field tests. While only three patients 214*a*-214*c* are shown, it should be understood that more Visual Test Units can be used to test more than three patients simultaneously. In particular, as shown, each patient 214*a*-124*c* is equipped with an HMU 204*a*-204*c*, respectively, mounted over the respective patient's head. The HMUs 204*a*-204*c* are configured to be mounted on each patient 214*a*-214*c* so that several electrical and optical components of the HMUs 204*a*-204*c* are aligned with the patients' eyes as is described in further detail below. Each HMU 204*a*-204*c* is tethered to a respective CU 202*a*-202*c*.

As illustrated, the CUs 202*a*-202*c* include a CU Interface 202*ai*-202*ci* (e.g. a graphical user interface) that is shown on the associated CU Displays, for use by a Technician 216*b*. The CU displays may be implemented using displays that provide a touch screen interface in which case the CU Interface 202*ai*-202*ci* may be GUI-based and receive commands from the Technician 216*b* receiving touches on the CU display. Alternatively, in other embodiments, the CU displays are not touch sensitive and the CU Interface 202*ai*-202*ci* includes at least one physical button that the Technician 216*b* can touch to input a command. For instance, in the case of 'patient 3' 214*c*, the Technician 216*b* is able to use the CU Interface 202*ci* to achieve a proper alignment of the patient's eye pupils, with certain electrical and optical components inside the HMU 204*c*, based on a video feed of the patient's eyes generated by the Eye Tracking Cameras installed inside the HMU 204*c*. In this manner, the Technician 216*b* is able to correctly adjust the mounting of the HMU 204*c* on the head of patient 214*c* such that during testing the visual stimuli are provided to the eyes of the patient 214*c* so that their eyes are correctly aligned with the Test Displays and the Eye Tracking cameras of the HMU

204*c*. In the illustrated embodiment, patient 1 (patient 214*a*) is being administered a Clicker Test (e.g., using clicker 218), while patients 2 and 3 (patients 214*b* and 214*c*) are being administered Eye Movement Tests.

As shown, the CUs 202*a*-202*c* can communicate (e.g., via an Ethernet connection 206) with a Technician Computer 208. In at least some embodiments, this can allow a Technician 216*a* to remotely interact with the CUs 202*a*-202*c* from the Technician Computer 208. Accordingly, the Technician can use the Technician Computer 208 to administer multiple visual field tests to patients 214*a*-214*c* simultaneously. It will be appreciated that, testing patients simultaneously can increase the operating efficiency of Technician 216*a* by avoiding the need to individually test patients 214*a*-214*c* on a one-by-one basis sequentially. The Technician 216*a* can also use the Technician Computer 208 to interact with the CUs 202*a*-202*c* to set and adjust test parameters, to view the raw vision test data as it is being obtained in real-time, and to view statistical analysis reports that are generated at the CU 202 based on the vision test results data for each patient.

For example, the Technician Computer 108 generally includes a communication interface for communicating with the plurality of Visual Test Units over the communication network 206; a display screen for presenting a user interface to allow the Technician 216*a* to interact with the plurality of Visual Test Units; and a processor that is operatively coupled to the communication interface and the display screen. The processor of the Technician Computer 208 may be generally configured to: display the user interface on the display screen; receive Technician commands from the Technician 216*a* for selecting vision tests to be performed using each of the plurality of Visual Test Units; and transmit the Technician commands via the communication interface over the communication network 206 to the plurality of Visual Test Units to configure the Visual Test Units for performing the selected vision tests.

As shown in FIG. 2, at least one of the CUs 202*a*-202*c* can be mounted to a support structure, such as a mechanical arm, bracket or post, which is attached to the wall or the ceiling such that the CUs 202*a*-202*c* are at eye level for easy access by the Technician 216*b*. Alternatively, at least one of the CUs 202*a*-202*c* may be located on a table.

CU Components

Referring now to FIG. 3A, shown therein is an example embodiment of the electrical components of a CU 102 which can be used for any of CU's 102*a*-102*n* or 202*a*-202*c*. FIG. 3B shows power flow through the electrical components of the CU 102. FIG. 3C data flow through the electrical components of the CU 102. Except for the Driver Board, which is housed in the HMU, the primary electrical components are housed in the Control Unit 102 as illustrated in FIGS. 3A, 3B and 3C. The CU 102 comprises a computer board 302 having a main processor 304 and main memory 306, a PCIe board 308, a power supply unit 310 having a power converter 312 and a surge protector 314, an SG100 Board 316 having an I/O interface 318, two Video Capture Cards 322 and 324, a CU Display 320, a USB connection 326 for the computer board 302 and a power connection 328. In at least one embodiment, the SG 100 Board may be incorporated with the PCIe Board. Example implementations will be described for each of these components. However, it should be understood by those skilled in the art that there can be equivalent alternative implementations of these components.

The computer board 302 may be implemented using commercially available computer boards that provide the main processor 304 and the main memory 306 with sufficient processing power and storage capacity. The main processor 304 is communicatively coupled to the various electronic components of the CU 102 and controls the operation of the CU 102. The main processor 304 may be any suitable processor, controller or digital signal processor that provides sufficient processing power for the CU 102. In some alternative embodiments, the main processor 304 may be replaced with two or more processors with each processor being configured to perform different dedicated tasks. Alternatively, the main processor 304 may be implemented using application specific integrated circuit(s) including a combination of digital and analog circuits and other electrical components.

The main memory 306 can include RAM, ROM, and one or more hard drives and/or flash drives or some other suitable data storage elements. The main memory 306 includes software instructions which, when executed, configure the main processor 304 for performing specific functions in accordance with the teachings herein. For example, the main memory 306 includes software instructions for performing the various methods described herein. The main memory 306 may also be used to store raw vision test data, various statistic and vision test report data for various patients. Accordingly, the memory 306 may include a file storage system.

The software program instructions for implementing several of the software systems described herein are stored in the main memory 306. In particular, the main memory 306 stores the program code for implementing a User Interface (UI) software system, a Visual Test software system, an Eye Tracking software system and a Statistical Analysis software.

The main processor 304 can execute program instructions from the main memory 306 when implementing functions of the UI software system which configures the main processor 304 to communicate with the Technician Computer 108. For instance, the main processor 304 can be configured to transmit raw or processed vision test data to the Technician Computer 108, 208 for viewing by the Technician 216*a*. As another example, the main processor 304 can execute program instructions from the UI software system to allow the main processor 304 to communicate with other devices such as the remote server 112.

Alternatively, the main processor 304 can execute program instructions from the main memory 306 when implementing functions of the Visual Test software system when receiving data that was obtained with various sensors and/or electronics in the HMU 104 to obtain sensor data, a clicker signal and/or video image data when implementing different aspects of the Eye Movement Test or the Clicker Test or during the mounting of the HMU 104 for proper alignment of certain optical elements of the HMU with the patient's eyes.

As shown in FIGS. 3A, 3B and 3C, the power supply unit 310 of the CU 102 may be coupled to a standard 110 Volt alternating current wall plug or some other suitable energy source through the surge protector 314. The surge protector 314 is used to prevent damage to the circuit boards and circuit components of the CU 102 in the event of a power surge. The alternating current from the surge protector is then converted to low voltage direct current by the power converter 314, which is part of the power supply unit 310. As shown in the power flow diagram of FIG. 3B, at step 351, the 110 Volt AC current is provided to the power supply unit 310 which converts this to low voltage Direct Current (DC) power at step 352. The DC power is then provided by the Power Supply Unit 310 to different hardware components of the CU 102, including: the Computer Board 302, the Control Unit Display 320, the PCIe Board 308, the first Video Capture Card 324 and the second Video Capture Card 326 at steps 353, 354, 355, 356 and 357, respectively. Alternatively, in at least one embodiment, the Direct Current (DC) power would be provided by the Computer Board 302 to the PCIe Board 308 and that Board would then provide the power to the Video Capture Cards 322 and 324. The Computer Board 302 in turn sends the low voltage DC power to the SG100 Board 316 at step 358. Alternatively, in at least one embodiment, If the SG 100 Board is integrated with the PCIe Board, in which case the power would be provided to the PCIe Board 355 and not to the SG 100 Board 358. The SG100 Board 316 then sends the low voltage DC power to the Eye Tracking Cameras at the HMU via two cables and also sends the low voltage DC power to infrared LED lights 816 in the HMU at step 359. Alternatively, in at least one embodiment, if the SG 100 Board is integrated with the PCIe Board, the two cables would be connected directly to the PCIe Board. The Computer Board 302 also sends low voltage DC power to the Driver Board 806 in the HMU via the USB cable 326 at step 360. The Driver Board 806 situated in the HMU 102 distributes power to the speakers 532 and 534, the display sensors (light and heat) 540 and Test Displays 514 and 518 in the HMU 102. The power supply unit may be a commercially available unit that provides sufficient power capabilities to power and provide electrical protection for the CU 102 and HMU 104.

Referring now to FIG. 3C, shown therein is data flow among various components of the CU 102. An analog video feed of a series of images is received by the SG100 Board 316 via two cables from the Eye Tracking Cameras 528 and 530 of the HMU 104 at step 371. The SG100 Board 316 then sends that analog video feed to the PCIe Board 308 at step 372. Alternatively, in at least one embodiment, if the SG 100 Board is integrated with the PCIe Board, the analog video feed would be provided directly to the PCIe Board. The PCIe Board 308 then sends the analog video feed to the two Video Capture Cards 322 and 324 at step 373. The two Video Capture Cards 322 and 324 (one for each Eye Tracking Camera 528 and 530) convert the analog video feed into a digital video feed and then sends the digital video feed to both the Computer Board 302 and the Control Unit Display 320 at steps 375 and 376, respectively.

Simultaneously, the PCIe Board 308 includes electrical measurement circuitry for converting the analog video feed that it has received from the SG100 Board 316 or alternatively, directly from the Eye Tracking Cameras, into numeric binary data that comprises eye movement measurements obtained from the video image data which are then sent to the Computer Board 302. For example, the electrical circuitry of the PCIe Board 308 can be referred to as eye movement measurement circuitry that analyzes the video images and generates gaze data indicative of pupil positions during the eye movement in the video images. For example, the circuitry of the PCIe Board 308 may locate landmarks from the video images (i.e. pupil and corneal reflection locations) and sends the coordinates, timestamps etc. (i.e. numeric data) as a binary stream, referred to as gaze data, to the main memory 306 where it can be analyzed by the main processor when executing certain software instructions of the Visual Test software system. In particular, the PCIe Board 308 has circuitry for tracking the pupils in both eyes using a certain frequency, e.g. 240 Hz, and communicates via a PCIe bus (not shown) with a driver program to output binocular pupil position and pupil size data. In addition, the driver program may overlay pupil position symbology on to the video images of the eyes and converts the 240 Hz frame rate video images to 60 Hz video images for viewing on a standard video monitor. The main processor 304 can then access the gaze data from the main memory 306 for analysis for certain purposes.

In addition, in at least one embodiment, the analog video data is sent to the CU Display 320 for presentation to the Technician 216*b*. For example, the analog video data may be presented on the CU Display 320 to show a live video feed of the current vision testing that is being performed on a patient. The live video feed may also be used by the Technician 216*b* while they are mounting the HMU to the patient 214 such that there is proper alignment between the patient's pupils, the Eye Tracking Cameras 528 and 530 and the Test Displays 514 and 518 (this is explained in further detail with respect to FIGS. 21 and 28-31).

The live digital video feed is also received by the main processor 304 and may be accessed by the Technician 216*a* via the Technician Computer 208 when the Technician Computer 208 accesses the main processor of a particular Visual Testing Unit in order to see and monitor the eyes of the patient during vision testing and/or when mounting an HMU to the patient 214.

The Control Unit Display 320 is located at the front of the CU 102 (an example of this is shown in FIG. 4). In at least one embodiment, the CU Display 320 may provide a GUI as the CU Interface which the Technician 216*b* can interact with to perform certain tasks such as starting, pausing and restarting a vision test. Accordingly, the CU Display 320 may be implemented using a touch sensitive screen. The CU Display 320 can also be used to display a video feed of the patient's eyes during a vision test or during the mounting of the HMU and alignment of certain optical components of the HMU with the patient's pupils. In some cases, the CU Display 320 may be implemented using a 23.8" LCD Display, having a 1920×1080 resolution with a P-Cap Touch Screen. In alternative embodiments, the CU Display 320 may be implemented using a commercially available non-touch sensitive display in which case the CU interface includes at least one physical button that the Technician 216*b* can interact with to provide commands to the CU 102 or view certain data on the CU Display 320.

In an alternative embodiment, the CU 102 and the CU Display 320 may be physically independent from one another. For example, the CU Display 320 may be provided by an external device such as a tablet, smartphone or other computing device, and the CU 102 may communicate and send video and other data to the external device and receive user inputs from the external device where the user inputs are related to vision testing.

All of the CUs 102*a*-102*n* have the same components and can generally be used in the same manner. However, in at least one embodiment, if two or more CUs 102*a*-102*n* are being used together as illustrated in FIGS. 1 and 2, one of the CUs may be designated as a "Master Control Unit". The Master Control Unit may be programmed and configured to save the vision test data for the vision tests conducted by all of the CUs 102*a*-102*n* during a given period of time.

As can be seen in FIG. 2, the clicker 218 has a cable that is attached to the CU 202*a*. It should be understood that a wire in the cable of the clicker 218 is coupled with a USB cable via a jack (not shown) at the CU 102*a*. Therefore, a clicker signal that indicates when the patient 214*a* presses the clicker 218 is sent to a Driver Board of the HMU 204*a* where the clicker signal is processed according to functionality encoded in the Firmware as is described in further detail herein (e.g., see FIG. 24).

Referring now to FIG. 4, shown therein is an example embodiment of the exterior of a CU 102 showing a housing 402, the CU Display 320, user interface elements 404 and a holder 406. Some of the user interface elements 404 are informational components that are used to show data such as, but not limited to, text box 404*a* that shows the patient name and possibly age for the current patient being tested and text box 404*d* that shows the elapsed time of the current vision test. Some of the user interface elements 404 are input controls such as input button 404*c* that allows the Technician 216*b* to pause a vision test that is currently being conducted. Some of the user interface elements 404 are navigational components such as navigation button 404*b* which allows the Technician 216*b* to navigate to a different GUI that is shown on the display 320 for listing the test settings for the vision test that is to be performed. It should be understood that in other embodiments, there may be other user interface elements 404. Alternatively, as described previously, the CU Display 320 may be a non-touch sensitive screen in which case the user interface elements 404 are provided using physical buttons. The holder 406 can be hooks, pegs or posts that are used to hold a clicker such as clicker 218 in FIG. 2.

HMU Components

The mechanical, electrical, optical and other components of the HMU 104 are illustrated in FIGS. 5-18 and such parts are generally described herein.

Figure 5:
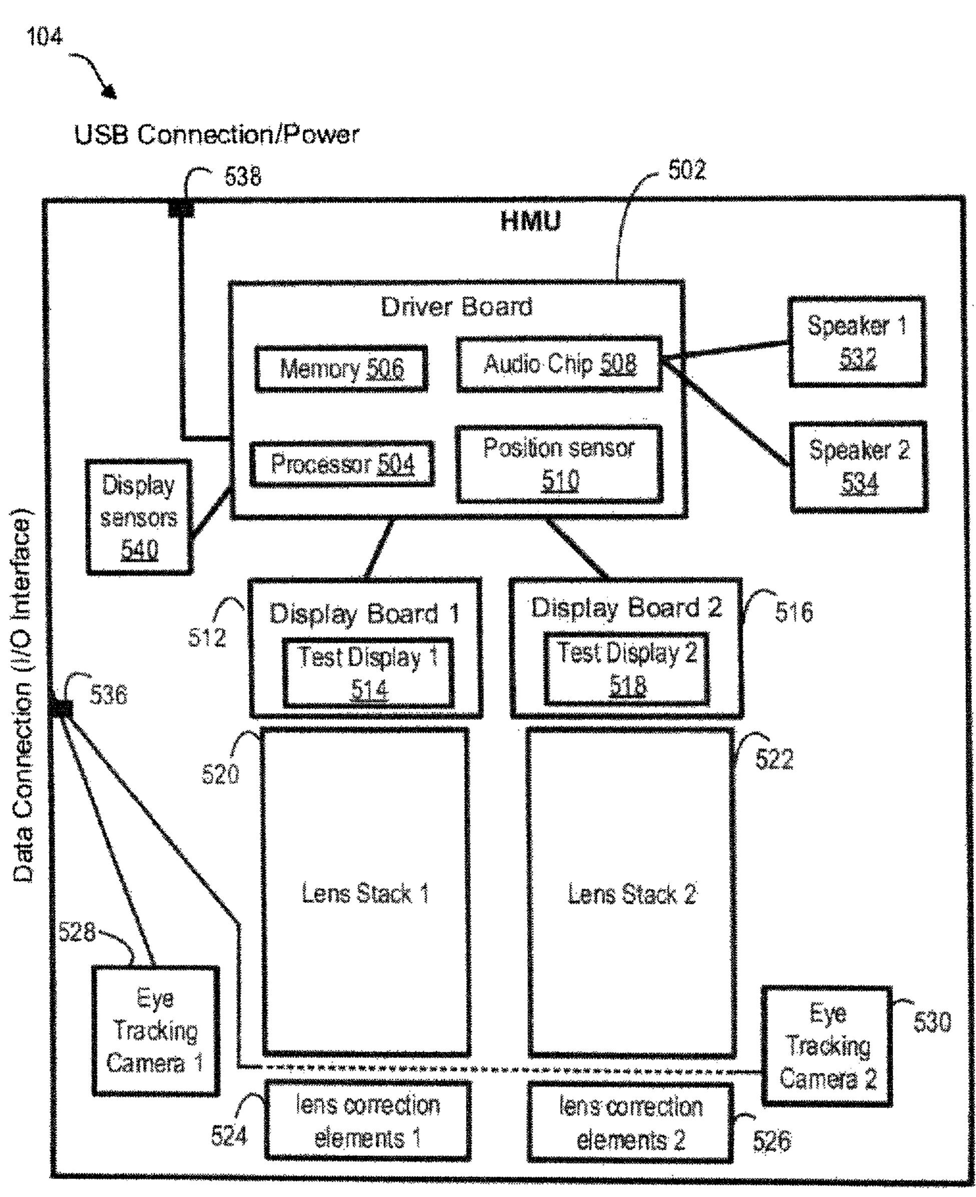
FIG. 5 illustrates an example embodiment of the components of an HMU.

Referring now to FIG. 5, shown therein is an example embodiment of the various components of an HMU 104 which can be used for any of HMUs 104*a*-104*n* or 204*a*-204*c*. The HMU 104 comprises a Driver Board 502 having a processor 504, memory 506, an audio chip 508, a position sensor 510, first and second display boards 512 and 516 having Test Displays 514 and 518, respectively, first and second Lens Stacks 520 and 522, first and second lens correction elements 524 and 526, first and second Eye Tracking Cameras 528 and 530, first and second speakers 532 and 534, an I/O interface 536, a USB/power connection 538 and display sensors 540. In at least one embodiment, the Video Capture Cards could be placed adjacent to each Eye Tracking Camera and connected thereto instead of being placed in the CU. Example implementations will be described for each of these components. However, it should be understood by those skilled in the art that there can be equivalent alternative implementations of these components.

The Driver Board 502 receives power from the CU 102 via the USB connection 538 and provides this power to various components of the HMU 104 including the processor 504, the memory 560, the audio chip 508, the first and second Test Displays 514 and 518, as well as the first and second speakers 532 and 534. The Eye Tracking Cameras 528 and 530 receive power from the SG100 Board 316 located in the CU 102 via two cables or, alternatively, directly from the PCIe Board.

The processor 504 controls the operation of the HMU 104 in response to signals provided by the CU 102, such as signals that are used to control driver circuits (not shown), which send driver signals to activate certain elements of the Test Displays 514 and 518, respectively, for generating visual stimuli having certain intensity levels and positions for presentation to the eyes of the patient 214. In at least one embodiment, the Test Displays 514 and 518 are not opaque so that a light source can be placed behind each of the Test Displays 514 and 518 for increasing the light output of the Test Displays 514 and 518. These functions are performed using a Firmware system that is stored in the memory 506 which has program instructions that, when executed by the processor 504, cause the processor 504 to control various components of the HMU 104 for performing various functions. The processor 504 and the memory 506 may be implemented similarly to the main processor 304 and the main memory 306 although the memory 506 may not have as much capacity as the main memory 306.

The audio chip 508 and the speakers 532 and 534 operate to allow the Technician 216*a* to communicate to a patient 214, who may be any of patients 214*a*-214*c*, from the Technician Computer 208 by providing audible verbal instructions or audio alerts to the patient 214 during the vision testing. The audio chip 508 and the speakers 532 and 534 can be implemented using available electronics as is known by those skilled in the art. The speakers 532 and 534 are preferably lightweight speakers.

The position sensor 510 can be an accelerometer and/or a gyroscope. The position sensor 510 is used to obtain head movement data for the patient 214 during testing as the position of their head (e.g. head tilt) may affect the vision test results. If the position sensor 510 is an accelerometer then acceleration data will be obtained for the X, Y and Z directions for movements made by the head of the patient 214. If the position sensor 510 is a gyroscope, then the position sensor 510 will provide orientation data indicative of the rotation around the X, Y and Z directions for movements made by the head of the patient 214. Accordingly, depending on the particular embodiment, the head movement data may comprise acceleration data and/or orientation data. The head movement data can be sent to the CU 102 where the data can be analyzed by the main processor 304 when executing certain software instructions of the Visual Test software system. The position sensor 510 can be implemented using available electronics as is known by those skilled in the art.

The display boards 512 and 516 can be implemented using printed circuit boards and provide power to the Test Displays 514 and 518, respectively. The Test Displays 514 and 518 generally have an array of active elements that are at locations which can be called pixels and these active elements generate light. The Firmware system that is executed by the processor 504 causes the processor 504 to send command signals to the Test Displays 514 and 518 for generating light at certain locations with a certain intensity and for a certain duration in order that a light stimulus is presented at the correct location and of the correct size, intensity and duration to the one of the patient's eyes in accordance with the vision test that is being performed. Depending on the implementation, the Test Displays 514 and 518 are implemented to have a brightness that is greater than 3,200 Nts as the brightness of the visual stimuli at the eyes of the patient is preferably at least 3,200 Nts and the light generated by the Test Displays 514 and 518 will decrease as the light rays for the visual stimuli pass through each successive optical element in the optical system. The brightness and location of specific pixels may also have to be adjusted to compensate for distortion of light through the optical system depending on the specific optical system implemented.

The Lens Stacks 520 and 522 generally include an identical arrangement of optical elements for receiving the light rays of the visual stimuli generated by the Test Displays 514 and 518, respectively, and project the light rays of the visual stimuli so that they are located within the Eye Box at the pupils of the patient 214. For example, the optical elements may include one or lens, and one or more mirrors that have a certain location and orientation (i.e. angle) relative to one another to project the light rays of the visual stimuli as described with a minimal amount of distortion or aberration. An example embodiment of an arrangement of optical elements that can be used for the Lens Stacks 520 and 522 is shown in FIG. 12.

The lens correction elements 524 and 526 are optical elements that are removably inserted into the HMU 104 for correcting for any eye sight issues that the patient 214 may have. For example, the lens correction elements 524 and 526 may be used to adjust for cylindrical error for the eyes of the patient 214, which may be due to astigmatism. An example embodiment that can be used for the lens correction elements is shown in FIGS. 13-18.

The Eye Tracking Cameras 528 and 530 along with infrared light sources (not shown in FIG. 5) are disposed and arranged to obtain images of the pupils of the patient 214 during the mounting of the HMU to the patient 214 as well as during vision testing of the patient 214. For example, a pair of light sources, such as LED infrared lights 816 (see FIG. 8), are disposed at the front of a horizontal portion of the Lens Stacks 502 and 522 in order to illuminate each eye of the patient during image capture by the Eye Tracking Cameras 528 and 530. Alternatively, in at least one embodiment, the light sources may be provided in the housing of the Eye Tracker Cameras. The Eye Tracking Cameras 528 and 530 are implemented to detect infrared rays that are reflected from the pupil as well as the cornea of the eyes of the patient 214 when the LED infrared lights 816 are shining infrared light on the eyes of the patient 214. Infrared light is used as it allows for clearer demarcation of the pupils of the patient 214 which allows for increased accuracy in gaze direction measurement. Accordingly, such illumination by the infrared light sources enables the Eye Tracking Cameras 528 and 530 to obtain video data showing the location and movement of each pupil. This video data can be provided to the SG100 Board 316 via the data connection 536 so that the video data can be shown on the CU Display 320 and/or on the Technician Computer 208 as a live stream of images.

The Eye Tracking Cameras 528 and 530 are implemented to acquire images at a certain frame rate, such as at least 240 Hz, or in some cases 500 Hz or 1000 Hz, for example, to provide video data, which may be analyzed using certain methods such as the Eye Movement Algorithm. This is advantageous since cameras that operate at a lower speed will not provide sufficient data points to accurately determine when Responsive Eye Movements and Non-Response Events have occurred during vision testing.

The display sensors 540 generally includes a pair of light sensors and a pair of temperature sensors and each of these sensors are located in or near one of the Lens Stacks 520 and 522. For example, FIG. 8 shows a Light Sensor 808 and a temperature sensor 810. Each light sensor is mounted in close proximity to one of the Test Displays 514 and 518 for sensing the amount of light that emanates from the Test Display 514 and 518 at the top of the Lens Stacks 520 and 522, respectively, and generating light data indicative of the amount generated light. The Temperature Sensors may also be mounted adjacent to the respective Test Displays 514 and 518 for generating temperature data indicative of the amount of heat that is generated by the Test Displays 514 and 518. These sensors are used: (1) to ensure that the HMU 104 operates in a safe manner during vision testing and (2) to perform calibration.

For example, if either of the Test Displays 514 and 518 malfunction such that they produce too much light then this will be captured in the light data which is analyzed by the processor 504 when executing certain software instructions from the Firmware system. When the processor 504 determines that the amount of light generated by one of Test Displays 514 and 518 is excessive, for example by comparison to a predetermined light threshold, such that the amount of generated light may be damaging to one or more eyes of the patient 214, then the processor 504 will generate a command that is sent to the corresponding display board for shutting off the Test Display that is generating too much light. The light data provided by the light sensors may also be used by the processor 504 when performing calibration on the Test Displays 514 and 518 to calibrate the amount of light that emanates from the Test Displays 514 and 518.

As another example, each temperature sensor generates temperature data which is indicative of the temperature of one of the Test Displays. If either of the Test Displays 514 and 518 generate an amount of heat that is greater than a predetermined heat threshold then this may be indicative that the Test Display may soon malfunction or may be operating in a condition which is not safe for the patient 214. The processor 504, when executing certain software instructions from the Firmware system, may monitor the temperature data to determine when the temperature data exceeds the predefined temperature threshold. When this happens, the processor 504 will generate a command that is sent to the corresponding display board for shutting off the Test Display that is generating too much heat and has a temperature greater than the predefined temperature threshold.

Referring now to FIGS. 6 to 11, shown therein are various views of certain components of an example physical embodiment 104*p* of an HMU. However, it should be understood by those skilled in the art that there can be equivalent alternative implementations of the components shown in FIGS. 6 to 11 as long as they provide similar functionality to what is described herein.

Referring to FIG. 6, shown therein is a front elevation view of the HMU 104*p*, which comprises a Shell 601 that provides a protective housing for the various components of the HMU 104*p*. The Shell 601 is generally shaped as goggles and protrude a certain distance away from the face of the patient 214 to provide enough physical space to accommodate the various components of the HMU 104*p*. The Shell 601 is preferably made from a material that is light-weight but has enough structural strength such that the location of the various components of the HMU 104*p* are stable. The material used for the Shell 601 is also durable enough for repeated handling by the Technicians 216*a*, 216*b* and other people so that the HMU 104*p* has an acceptable life time. The material used for the Shell 601 may be a durable plastic or other similar material.

The Shell 601 also comprises various apertures and slots to enable certain functions to be performed on the HMU 104*p* when it is being adjusted so that it can be used for performing vision testing on a certain patient 214. For example, the Shell 601 includes two Lens Focus Scale Viewpoints 602 located that are each located at a front portion of the Shell 601 above one of the Lens Stacks, IPD Adjustment Viewpoints 604 that are each located at the front of the Shell 601 at about a mid-point of one the Lens Stacks, and Spherical Lens Focus Adjustment rings 606 that are each located at a front portion of the Shell 601 above one of the Lens Stacks. Each of these elements are described in further detail below. The IPD Adjustment Viewpoints 604 are apertures that allow the Technician 216*a* to view the amount of IPD adjustment that is provided by adjusting the IPD adjustment mechanism. The patient 214 is not able to view the IPD Adjustment Viewpoints 604. In at least one embodiment, correction of spherical error of the patient's eyes will be affected by adding a second corrective lens to each lens element 524 and 526 (see FIGS. 9, 13, 14 and 15) in which case the Spherical Lens Focus Adjustment Rings would be eliminated.

Referring to FIG. 7, shown therein is a side elevation view of the HMU 104*p*, which comprises an adjustable harness that comprises a series of bands or straps and adjustment elements that are in an arrangement for removably securing the HMU 104*p* to the head of the patient 214, Speaker Headphones 714 for providing audio instructions to the patient 214, and an IPD Adjustment Knob 716. The Speaker Headphones 714 are a physical implementation of one of the speakers 532 and 534 and it should be understood that there may be another speaker headphone on the opposite side of the Shell 601 which is not visible in FIG. 7. Various bands of the adjustable harness are tightened or loosened to ensure that the HMU 104*p* is securely mounted to the head of the patient 214, and to ensure that the eyes of the patient 214 are correctly aligned with the Eye Box and Eye Tracking Cameras.

In this example embodiment, the adjustable harness includes an upper or Top Headband 702, a Top Headband Length Adjustment Knob 704, a Goggle Interface 706, a Side Head Band 708, a Back Head Support 710, and a Side Head Band Adjustment Knob 712. In this example embodiment, the Shell 601 also comprises Side channels 718 and Head Band length adjustment arm channel 1010 (see FIG. 10) for holding certain bands in place and protecting the bands. For example, the Side Head bands 708 can be disposed inside of channels 718, while the Top Headband 702 can be disposed inside of corresponding top channel 1010.

A first end of the Top Headband 702 is secured to the top portion of the Back Head Support 710. The Top Headband 702 then passes through the Top Headband Length Adjustment Knob 704 and then is received by the adjustment arm channel 1010 of the Goggle Interface 706. The Side Head Band 708 has a first portion with a first end that is coupled to a first side of the Goggle interface 706. The Side Head Band 708 then loops over the ear of the patient 214 and is received by the Side Head Band Adjustment Knob 712. Although this is not shown, it should be understood that the second portion of the Side Head Band 708 is coupled to a second side of the Goggle Interface 706. The second Side Head Band 708 then loops over the other ear of the patient 214 and is received by the Side Head Bank Adjustment Knob 712. The Goggle Interface 706 consists of flexible material so that the Goggles sit comfortably on the head of patient 214. For example, a closed cell foam may be used as part of the Goggle Interface 706 where the foam is located so that it makes contact with the bridge of the nose area, the brow, and the eye sockets of the patient 214. This helps make the HMU 104 more comfortable to wear and also helps to block external light from entering the interior of the HMU 104.

The Top Headband 702 may be adjusted by way of the Top Headband Length Adjustment Knob 704. The back of the Head Support 710 is located below the occiput (i.e. back) of the head of the patient 214 to ensure a secure fit. The length of the Side Head Band 708 is adjustable using the Side Head Band Adjustment Knob 712. The Top Head Band Adjustment Knob 704 and the Side Head Band Adjustment Knob 712 can be rotated in one direction to tighten the corresponding bands or in the opposite direction to loosen the corresponding bands. For example, if one of knobs 708 and 712 is tightened it draws the corresponding band into the corresponding channel and if one of the knobs 708 and 712 is loosened then the opposite occurs. The head bands for the HMU 104*p*1 shown in FIG. 11 operate in a similar manner.

Referring now to FIGS. 8 and 10, shown therein are cross-sectional views of the HMU 104*p* of FIGS. 6 and 7 taken along sectional lines 8-8 and 10-10, respectively, in FIG. 6. Like elements in FIGS. 8 and 10 are indicated using the same reference numbers used in FIGS. 6 and 7. Furthermore, it should be understood that the elements shown in FIGS. 8 and 10 are for one of the eyes of the patient 214 and there is a corresponding second set of these elements for the other eye of the patient 214. Please note that FIGS. 7 and 10 do not show the attachment of the cable from the CU 102 to the HMU 104 although it should be understood that there is such a connection and an example of this is shown in FIG. 11.

As illustrated in FIG. 8, a Lens Stack housing 802 is located within the Shell 601 that includes the optical elements of one of the Lens Stacks, such as Lens Stack 520 for example, a Test Display 804 is electrically coupled to a Driver Board 806, a Light Sensor 808, a Temperature Sensor 810, an Eye Tracking Camera 814, and LED lights 816. The elements of the Lens Stack include a cold mirror 812, and various Lenses 818*a*-818*d*. Although four Lenses are shown there may be a different number of Lenses at possibly different locations in alternative embodiments of the Lens Stack. The Test Display 804 is disposed above the Lens Stack Housing 802, and the Temperature sensor 810 is located adjacent the Test Display 804. The Light sensor 808 is located within the Lens Stack Housing 802 to sense the amount of light emanating from the Test Display 804. The Test Display 804 also comprises a power board that provides power to the Test Display 804. The Driver Board 806 is mounted in an upper region of the Shell 601 such as above or beside the Test Display 804, for example. The Driver Board 806 sends signals to the Test Display 804 for activating certain regions of the Test Display 804 to generate visual stimuli having a particular location, size, and intensity.

The Eye Tracking Camera 814 is disposed substantially at eye level and directed toward but spaced horizontally away from the eye of the patient 214. The Eye Tracking Camera 814 is also located behind the cold mirror 812 and outside of the Lens Stack Housing 802. This arrangement is possible since the cold mirror 812 will reflect the entire visible light spectrum and transmit infrared wavelengths that are generated by the LED lights, reflect off of the pupils and cornea of the patient 214, pass through the cold mirror 812 and are detected by the Eye Tracking Camera 814. However, the cold mirror 812 will reflect the light stimuli emanating from the Test Displays when the light stimuli comprise light rays from the visible portion of the light spectrum.

As illustrated in FIG. 10, the HMU 104*p* includes a Spherical Lens Focus scale 1002 mounted to the Shell 601, an IPD adjustment screw 1006 that passes through a channel (not shown) in the Shell 601, a display mount 1014 disposed at an upper portion of the Lens Stack for mounting the Test Display (not shown) and an eye piece 1016 located along an interior portion of the Shell 601. When the HMU 104*p* is worn by the patient 214, the eye piece 1016 is sits adjacent the eye socket of the patient 214.

Shown in the figure inset of FIG. 10, is the IPD adjustment screw 1006 as well as a lead nut 1026 which are used to move the Lens Stacks closer together or further apart based on the IPD of the patient 214. The IPD adjustment screw 1006 comprises a central portion 1018, first and second threaded rods 1020 and 1022 on either side of the central portion and stops 1024 therebetween. The ends 1006*e* of the IPD adjustment screw 1006 protrude slightly past opposite portions of the Shell 601 and each receive the IPD adjustment knobs 716. There are two lead nuts 1026, only one of which is shown for ease of illustration. Each lead nut 1026 has a plate 1028 with two apertures 1028*a* and a sleeve 1030 that is and has a channel 1030*c* with internal threads that match the external threads of the threaded rods 1020 and 1022 of the IPD adjustment screw 1006. The longitudinal axis of the sleeve 1030 is offset forwardly from the plate 1028. The apertures 1028*a* are used to attach each lead nut 1026 to a respective Lens Stack and one of the lead nuts 1026 is engaged with the first threaded rod 1020 of the IPD adjustment screw 1006 while the other lead nut 1026 engages the second threaded rod 1022. The external threads of the threaded rods 1020 and 1022 are oppositely arranged and are engaged by the internal threads of the channel 1030*c* so that when the IPD adjustment knob 716 is rotated in one direction, the lead nuts 1026, and consequently the Lens Stacks to which they are attached move closer to one another and when the IPD adjustment knob 716 is rotated in the opposite direction, the lead nuts 1026, and consequently the Lens Stacks to which they are attached move further apart from one another. The bottom portions of the Lens Stacks may rest on a horizontal post or plate that provides support to the Lens Stacks when they are stationary and when they are moved. The IPD adjustment mechanism comprises the IPD adjustment screw 1006, the IPD adjustment Knob 716 and the IPD Adjustment Viewpoints 604.

Referring now to FIG. 9, shown therein is a rear view of the exterior of a Lens Stack Housing 802 of the HMU 104*p*. A Cylindrical Correction Lens Mount 904 is attached to a bottom portion of the Lens Stack housing 802. The Cylindrical Correction Lens Mount 904 is adapted to receive a Cylindrical Correction Lens 902 which is removably inserted therein. The Cylindrical Correction Lens 902 is used to correct for certain vision issues of the eyes of the patient 214 as described in further detail herein. An example embodiment of an optical arrangement that can be used for the Cylindrical Correction Lens Mount 904 is shown in FIGS. 13-18.

Referring now to FIG. 11, shown therein is a side view of another example embodiment of a physical HMU 104*p*1. The HMU 104*p*1 also comprises a Shell 1102, a back of head support 1104, and an alternative harness arrangement having a series of bands including: a top head band 1106, a side head band arrangement 1108 having side portion 1109, upper portion 1110 and lower portion 1112, a top sleeve 1103, cable housing 1114 that also acts as a counterweight and a rear sleeve 1116 for receiving corresponding portions of the top head band 1106 and the side headband arrangement 1108. It should be understood that the harness arrangement of HMU 104*p*1 is duplicated on the other side of the HMU 104*p*1 that is not visible in FIG. 11. In an alternative embodiment, the Shell 1102 and the goggle portion may be a single integral structure.

The HMU 104*p*1 also includes a top head band length adjustment knob 1118 and a rear head band length adjustment knob 1120 for allowing the Technician 216*b* to adjust the harness arrangement to securely mount the HMU to the head of the patient 214. A first end portion of the top head band 1106 is releasably coupled a top head band length adjustment knob 1118. Side portions 1109 (other side not shown but is the same) are fastened to the side of the Shell 1102. The lower portions 1112 (and matching on the other side) are received by the rear sleeve 1116 and coupled to the rear head band adjustment knob 1120. A second end portion of the top band 1106 is coupled (e.g. stitched or glued) with a first end portion of the upper portion of the side band arrangement 1110. The HMU 104*p*1 includes the top head band length adjustment knob 1118 and the rear head band length adjustment knob 1120 for allowing the Technician 216*b* to adjust the harness arrangement to securely mount the HMU to the head of the patient 214. The various bands may be made from one piece of plastic (injection molded or stamped) or made from multiple pieces and fastened together with snaps, allowing for pieces to rotate for more flexibility. On an underside of the bands, closed cell foam may be glued for comfort, and potentially to hide electrical cables.

The HMU 104*p*1 also includes a connection port 1122 for receiving a first end of a cable 1124 that has a second end which is connected to the CU 102. The cable 1124 comprises wires for sending power from the CU 102 to the HMU 104*p*1. The cable 1124 also has data lines or data wires for sending control signals from the CU 102 to the HMU 104*p*1 and for sending data from the HMU 104*p*1 to the CU 102. The nature of the data signals and flow of control signals and data between the CU 102 and the HMU 104*p*1 are described in further detail below. It should be understood that this connection also applies to the HMU 104*p* although not shown in FIGS. 6 to 10.

Referring now to FIG. 12, shown therein is an example embodiment of a schematic of a Lens Stack 1200 showing the effect on the disbursement of light rays of the visual stimuli as these light rays pass through the lenses of the Lens Stack 1200 in order to provide an image that is spatially located in an Eye Box 1218 of a particular diameter near the pupils 1216 the patient's eyes 1214. In this example, the propagation of a first group of light rays L1 and a second group of light rays L2 is shown. It should be noted that the lenses shown in FIG. 12 do not include the Cylindrical Correction Lens (e.g. lens 904).

The Lens Stack 1200 generally comprises a first section 1202, which is angled, and a second section 1204 which is substantially horizontal. The first and second sections 1202 and 1204 each comprise one or more lenses. In this example, the section 1202 comprises lens 1206, 1208 and 1210 while the section 1204 comprises cold mirror 812 and lens 1212. The lenses 1206, 1208 and 1210 are aligned at their optical axes (i.e. their midpoints) to form a longitudinal optical axis for the first section 1202 that is angled such that the propagated light rays L1 and L2, which are generated from Test Display 804, reflect off of the cold mirror 812 such that they are substantially horizontal. The central midpoint of the Test Display 804 is also arranged with the longitudinal optical axis of the first section 1202. It should be noted that the Test Display 804 and the cold mirror 812 of FIG. 8 are used here for illustrative purposes for each of illustration.

It should also be understood that the Lens Stack 1200 shown in FIG. 12 is but one example of a Lens Stack that may be used with any of the HMUs shown herein and that there may be other embodiments of Lens Stacks which have first and second sections with different arrangements of lenses that generally behave in an overall manner as will now be described for lens sections 1202 and 1204. For example, in an alternative embodiment, the function of the first and second sections 1202 and 1204 of the Lens Stack 1202 can be reversed in which case a hot mirror is used instead of the cold mirror 812.

The lenses 1206, 1208, 1210 and 1212 have surfaces of curvature and positions that are collectively selected such that the light rays L1 and L2 are presented within the Eye Box 1218 with preferably minimal distortion when they reach the patient's eye 1214. For example, the center of lenses 1206 and 1208 have angles of curvature and thicknesses for causing incident light rays, such as L1, to slightly widen, while lens 1210 has angles of curvature 1210 and a thickness which causes these light rays to converge and to collectively have a smaller cross-sectional area when they contact a central area of the cold mirror 812 which is titled so that the light rays are reflected and propagate generally horizontally to the lens 1212. The central portion of Lens 1212 has angles of curvature, a thickness and a position that are selected to cause these light rays L1 to collimate such that the cross-sectional area of these light rays is confined within the Eye Box 1218 when the reach the eye 1216 of the patient's eye 1214.

As another example, for light rays that originate from pixels of the lower region of the Test Display 804, an example of which are light rays L2, the lenses 1206 and 1208 have angles of curvature and thicknesses for causing L2 to propagate along an angle such that they pass through an upper region of lens 1210. The upper region of lens 1210 has angles of curvature and a thickness such that the light rays L2 travel to an upper portion of the cold mirror 812 which causes the light rays L2 to reflect towards an upper region of lens 1212 which has angles of curvature and a thickness to refract and collimate the light rays L2 so that the cross-sectional area of the light rays L2 are confined within the Eye Box 1218 when the reach the patient's eye 1214.

As another example, for light rays that originate from an upper portion of certain pixels of the Test Display 804, the lenses 1206 and 1208 have angles of curvature and thicknesses for causing these light rays to propagate along an angle such that they pass through a lower region of lens 1210. The lower region of lens 1210 has angles of curvature and a thickness such that these light rays travel to a lower portion of the cold mirror 812 which causes these light rays to reflect towards a lower region of lens 1212 which has angles of curvature and a thickness to refract and collimate these light rays so that the cross-sectional area of these light rays are confined within the Eye Box 1218 when the reach the patient's eye 1214.

The Eye Box defines a physical region (i.e. volume) where the light rays from a visual stimuli can be presented to the patient's eyes 1214 such that the visual stimuli has minimal distortion. This is advantageous since if the visual stimuli were presented with distortion or aberration when they receive the patient's eyes 1214 then this can affect the reliability of the vision test, since stimuli of varying intensity, size and color should appear to the patient consistently, irrespective of where the stimuli is presented in the visual field of the patient 214. As previously mentioned, the lenses of the Lens Stack 1200 are generally selected and arranged such that the visual stimuli reach the patient's eyes 1214 within an Eye Box of between about 8 to 12 mm. As will be explained, prior to performing a visual field test, the HMU 104 is adjusted on the head of the patient 214 (e.g., through adjusting the various bands and an inter-pupillary distance (IPD) adjustment mechanism, as explained herein), so as to center each of the patient's pupils within the Eye Box (e.g. see FIGS. 29 to 31).

Although not shown in FIG. 12, it should be understood that reflections of the Infrared light rays (not shown) from the patient's eye 1214 would pass through the second lens section 1204 in a substantially horizontal manner along the optical axis of the second lens section 1204 such that these reflected light rays pass through the cold mirror 812 and are recorded by the Eye Tracking Camera 814 (e.g., see FIG. 8).

Figures 13, 14, 15:
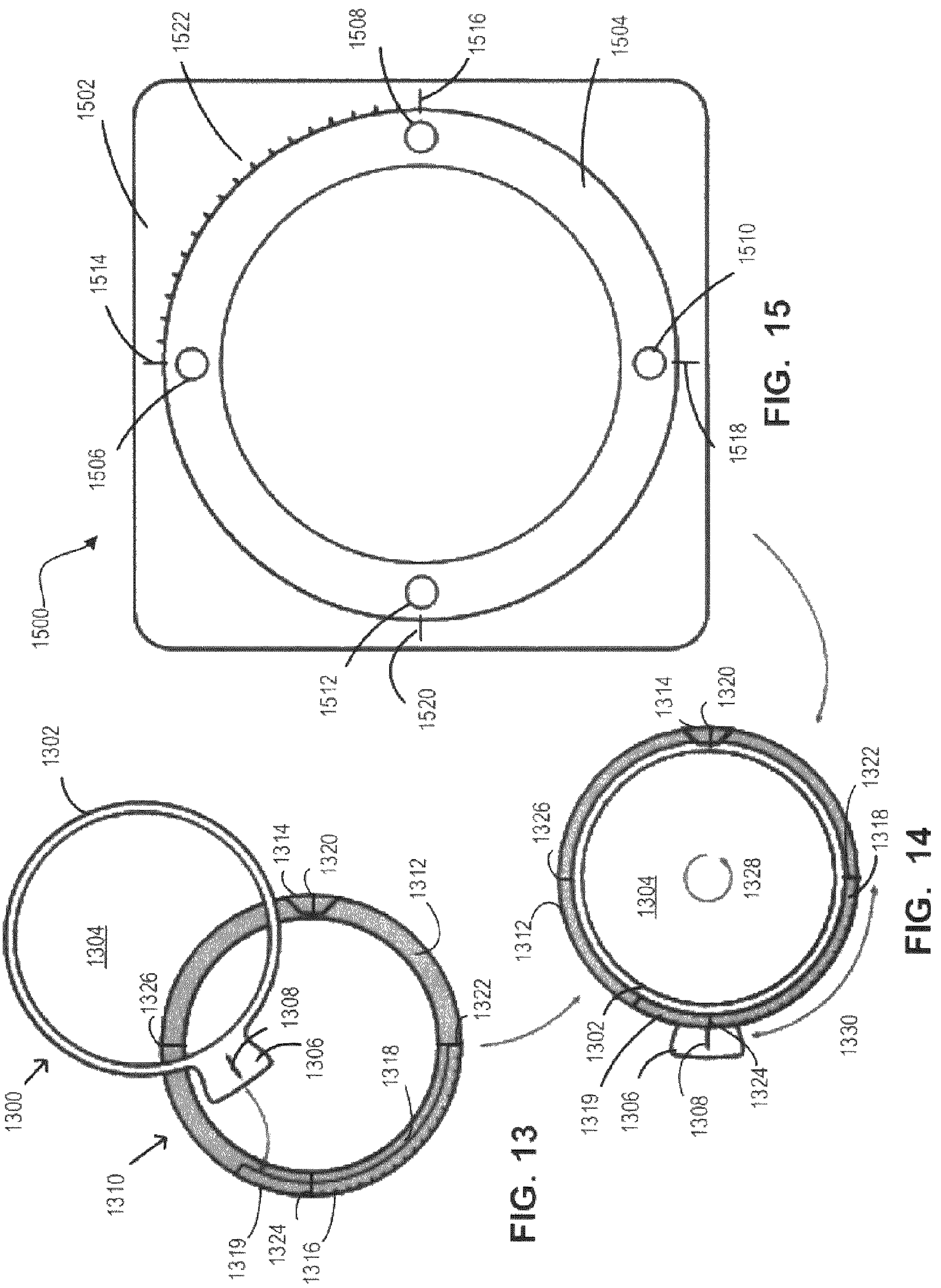

Referring now to FIGS. 13 to 15, shown therein are various views of an example embodiment of Cylindrical Correction Lens 1300, a lens mount attachment 1308 and a Cylindrical Correction Lens Mount 1500 that may collectively be removably inserted into the HMU 104*p* or 104*p*1 for correcting for any cylindrical vision issues (i.e. astigmatism) that the patient 214 may have. The Cylindrical Correction Lens 1300 is rotatably positioned with the lens attachment 1308 and the lens mount attachment 1308 is removably mounted to the Cylindrical Correction Lens Mount 1500.

The Cylindrical Correction Lens 1300 comprises a frame 1302 (e.g. a ring) that encloses a lens 1304 and has a positioning tab 1306 with a position indicator 1308. The positioning tab 1306 is located along a portion of the circumference of the frame 1302. There are different Cylindrical Correction Lens 1300 different for correcting different amounts of cylindrical refractive error that different patients may have. Accordingly, the appropriate Cylindrical Correction Lens is selected for mounting to the Cylindrical Correction Lens Mount 1500 when the patient is being prepared to undergo vision testing.

The lens mount attachment 1310 comprises a frame 1312, a retaining clip 1314 located along a portion of the frame 1312, a graduated lens guide 1316 located along an angular section of the frame 1312 and a slot 1318 that extends along the length of the graduated lens guide 1314 and is positioned underneath the graduated lens guide 1316 and above a bottom portion of the frame 1312. A tab insertion area 1319 is positioned adjacent the lost 1318. The retaining clip 1314 is raised above the upper surface of the frame 1312 to provide a gap that slidably receives a portion of the frame 1302 of the Cylindrical Correction Lens 1300. The retaining clip 1314 is semi-rigid. The lens mount attachment 1310 also comprises alignment markers 1320, 1322, 1324 and 1326 which are used when attaching the lens mount attachment 1310 to the Cylindrical Correction Lens Mount 1500.

In use, once the appropriate Cylindrical Correction Lens 1300 is selected for the particular patient 214 that is being testing, the Cylindrical Correction Lens 1300 is inserted into the lens mount attachment 1310 such that the positioning tab 1306 slides through the tab insertion area 1319 and then is rotated to slidably engage the slot 1318 until the portion of the frame 1302 adjacent the positioning tab 1306 rests against the graduated lens guide 1316. The frame 1302 of the Cylindrical Correction Lens 1300 is then rotated so that a portion of the frame 1302 that is generally opposite the positioning tab 1306 can slide between the retaining clip 1314 and the portion of the 1310 that is below the retaining clip 1314 of the lens mount attachment 1308 so that the Cylindrical Correction Lens 1300 is rotatably held in place.

Once the Cylindrical Correction Lens 1300 has been slidably inserted into the lens mount attachment 13010 the Cylindrical Correction Lens 1300 can then be rotated about an axis of rotation 1318 in a clockwise or counter-clockwise fashion (as indicated by double-headed arrow 1320) so that it provides the desired amount of correction for the cylindrical refractive error of the patient 214.

The Cylindrical Correction Lens Mount 1500 shown in FIG. 15 comprises a support 1502 (e.g. a plate) having a groove 1504, mounting members 1506, 1508, 1510 and 1512 positioned around the groove 1504, alignment markers 1514, 1516, 1518 and 1520 located at the mounting members 1506, 1508, 1510 and 1512 and a graduated lens guide 1522 located along a section of the groove 1502 on the support 1502. In this example embodiment, the mounting members 1506, 1508, 1510 and 1512 are magnets.

Once the Cylindrical Correction Lens is inserted into the lens mount attachment 1310, the lens mount attachment 1310 is then removably attached to the Cylindrical Correction Lens Mount 1500 such that the alignment markers 1320, 1322, 1324, and 1326 of the lens mount attachment 1310 align with the alignment markers 1514, 1516, 1518 and 1520 of the Cylindrical Correction Lens Mount 1500. The frame 1312 of the lens mount attachment 1310 comprises metal so that the frame 1312 is held against the support 1502 by the magnetic forces provided by the magnetic mounting members 1506, 1508, 1510 and 1512. The groove 1504 is sized to be slightly larger and have the same size as the frame 1312 of the lens mount attachment 1310 so that the frame 1312 is received within the groove 1504.

Referring now to FIGS. 16 to 18, shown therein is an alternative embodiment of a Lens Mount Attachment 1600 that may be used with the Cylindrical Correction Lens 1300 and the Cylindrical Correction Lens Mount 1500. In this case, the Lens Mount Attachment 1600 comprises a frame 1602, a retaining clip 1604, a graduated lens guide 1606, a slot 1608 and a tab insertion area 1609, which are mostly similar to the corresponding elements of the Lens Mount Attachment 1310. However, the Lens Mount Attachment 1600 includes magnets 1610, 1612, 1614, and 1616 that are positioned where the alignment markers 1320, 1322, 1324, and 1326 were positioned for the Lens Mount Attachment 1310. The magnets 1610, 1612, 1614, and 1616 have an opposite polarity to the magnets 1506, 1508, 1510 and 1512. Accordingly, in this embodiment, the Lens Mount Attachment 1600 is oriented such that the magnets 1612, 1614, 1616, and 1618 line up with the magnets 1506, 1508, 1510 and 1512, respectively, so that a graduated lens guide 1606 of the Lens Mount Attachment 1600 aligns with the graduated lens guide 1522 of the Cylinder Correction Lens Mount 1500.

The retaining clip 1604 of the Lens Mount Attachment 1600 has a folded tab 1605 with an overhang region **1805*o* for retaining the Cylinder Correction Lens 1300 in place when it has been inserted into the Lens Mount Attachment 1600 as shown in FIG. 17. A portion 1605*f* of the frame 1602 is made of flexible material to receive and abut the frame 1302 of the Cylinder Correction Lens 1300** so that it is not damaged.

In an alternative, or in addition to retaining clip 1604, the Lens Mount Attachment 1600 may include a snap lock 1618 for holding the Cylinder Correction Lens 1300 in place after it is inserted into the Lens Mount Attachment 1600. The snap lock 1618 includes a rotating clip 1619 that is rotatably coupled to the frame 1602, retaining pins **1619*p* and a tab 1619*t* that is biased upwards for forming a friction fit with the rotating clip 1691 when it is rotated in a closed position as shown in FIG. 18**.

Correction for Spherical Refractive Error

Continuing with the example embodiment shown in FIGS. 6 to 10, a mechanism for adjusting the distance between the Test Display 804 and the first lens **818*a* at the top of the Lens Stack to correct for spherical refractive error, commonly referred to as short or long distance vision, is provided for as illustrated in FIG. 10. That distance can be adjusted by turning the Spherical Lens Focus Adjustment Ring 606 as illustrated in FIGS. 6 and 10. The amount of spherical correction required for the patient 214 can be determined from the prescription for the glasses of the patient 214. The scale for the amount of adjustment, the Spherical Lens Focus Scale 1002, is located as shown on FIG. 10 and can be viewed by the Technician 216*b* through the Lens Focus Scale Viewpoint 602 as illustrated in FIG. 6. Accordingly, the Lens Focus Scale Viewpoint 602 may be viewed by the Technician 216*b* when rotating the Spherical lens focus adjustment ring 606 to cater to the particular vision of the patient 214; i.e. to correct for short-sightedness or far-sightedness. In at least one embodiment, correction of spherical error of the patient's eyes will be affected by adding a second corrective lens to each lens element 524 and 526 (see FIGS. 9, 13, 14 and 15**) in which case the Spherical Lens Focus Adjustment Rings would be eliminated.

Correction for Interpupillary Distance

A mechanism for adjusting the distance between the two Lens Stacks of the HMU **104*p* is provided to accommodate the fact that the interpupillary distance ("IPD") (that is, the distance between the pupils of the left eye and the right eye) varies from patient to patient. That mechanism is a double-screw mechanism referred to as an "IPD Adjustment Screw" 1006 as illustrated in FIG. 10. The distance between the two Lens Stacks is adjusted by turning the IPD Adjustment Knob 1008 as illustrated in FIG. 10. For example, turning the IPD Adjustment Knob 1008 in one direction will move the Lens Stacks closer together and turning the IPD Adjustment Knob 1008 in the other direction will move the Lens Stack apart from each other. The IPD Adjustment Knob 716 is also shown in FIG. 7. The scale for IPD Adjustment may be viewed by the Technician through the IPD Adjustment View Point 604 as illustrated in FIG. 6**.

Correction for Cylindrical Refractive Error

A mechanism is provided for correcting for cylindrical refractive error. Attached to the back of each Lens Stack (that is, closest to the patient's eye) is the Cylindrical Correction Lens Mount 902 illustrated in FIG. 9. A medical practitioner who uses the HMUs described herein may purchase or otherwise obtain a set of corrective Cylindrical Correction Lens 904 and inserts the Cylindrical Correction Lens, that corrects for the particle cylindrical refractive error for the patient, into the Cylindrical Correction Lens Mount as described in FIGS. 13-15. Alternatively, the cylindrical refractive error of the patient 214 may be corrected for by incorporating a Jackson Cross Cylinder in a portion of the Lens Stack. Moreover, in at least one embodiment, the spherical error may be corrected for in a similar manner by using spherical correction lens.

Cable Between the HMU and the CU

The various electrical components of the HMU (e.g. one of 104, **104*p* and 104*p*1) referred to above receive low voltage power from the CU 102 by way of a USB cable. The same USB cable carries data between the Main Processor 302 and the Driver Board 502 (or 806). The Driver Board 502 is connected to the Test Displays 804 by a different cable. The Integrated Video Board 316 as illustrated in FIG. 3, is connected to each of the two Eye Tracking Cameras 814 by two cables, such as 15 pin connector cables, for example, or other suitable cables through the I/O interface 318. Each of these cables can be incorporated into a larger electrical cable that connects the HMU 104, 104*p*, 104*p*1 to the CU 102**

Headphone Speakers

In at least one embodiment, the HMU **104*p* includes one or more audio speakers (e.g., ear buds, or headphones) 714, positioned over the patient's ears as illustrated in FIG. 7. For example, the Speaker Headphones 714 can be attached to the side bands 708 as shown in FIG. 7. As explained herein, the audio speakers 714 can deliver audible instructions or alerts to the patient 214 during the visual field test. For example, as provided herein, the audio speakers 714 may provide audio including general instructions from the Technician 216*a* to the patient 214 in respect of instructing the patient 214 on how to perform the visual field test or other vision test, or otherwise alert the patient 214** if their head is not in the upright position or their gaze is not focused on the central fixation target, depending on the vision testing being performed.

HMU—Optical Components

The optical components of the HMU 104, 104*p* or 104*p*1 include both Test Displays, the Lens Stacks housed in the two Lens Stacks Housings and the Cylindrical Correction Lenses. Depending on the actual embodiment, the number of lenses in the Lens Stacks, the spacing of the lenses in the Lens Stacks and the design of the lenses themselves will vary depending on the characteristics of the Test Displays and the desired Eye Box diameter. The implementation of these various optical components is to maximize the diameter of the Eye Box while simultaneously minimizing any aberration of the visual stimuli, particularly towards the periphery of the visual field of the patient 214.

Software Systems

In another aspect, at least one example embodiment is provided in accordance with the teachings herein for a software implementation that may be used for operating the CU 102 and a corresponding or associated HMU 104 as well as communicating between the CU 102 and the Technician Computer 108, 208 and/or the remote server 112. The software implementation comprises a User Interface (UI) software system, a Visual Test software system, a Statistical Analysis software system, and an Eye Tracking software system that each comprise software instructions (i.e. program code) for configuring the CU 102 to perform certain operations. The software implementation also includes a Firmware system that comprises software instructions for configuring the HMU 104 for performing certain operations. The functionality of each of the software system are described in further detail herein and with respect to FIGS. 19 to 32. For ease of illustration in the description which follows, the reference element HMU 102; the CU 104; and the Technician Computer 208 will be used but it should be understood that the functionality that will be described may apply to HMUs 102*a*-102*n*, and 202*a*-202*c*; the CUs 104*a*-104*n*, 204*a*-204*c*, 104*p* and 104*p*; and the Technician Computer 108. Also, the components of the CU 102 as shown in FIGS. 3 and 4 and HMU 104 as shown in FIG. 5 will be used in the following description as well as elements of the HMU 104*p* and HMU 104*p*1 shown in FIGS. 6-18 where these components are not explicitly shown in FIG. 5. Furthermore, Technician 216*a* or 216*b* may be used in the description depending on the actions being performed but it might be the same Technician that performs all of these actions.

The Eye Tracking Cameras 528 and 530 are set in the HMU 102 to focus on the eyes of the patient 214. The Eye Tracking software system does not control the Eye Tracking Cameras 528 and 530 but rather carries out such functions as: adjusting the luminosity of the infrared LED lights 816 such that the pupil and cornea of the eyes of the patient 214 are tracked properly; adjusting the size of the images of the eyes of the patient 214 that are recorded; and, determining which of the two Eye Tracking Cameras 528 and 530 is recording.

The Visual Test software system controls the actions of the CU 102 and HMU. The Visual Test System interprets the data provided by the Eye Tracking System and then controls the light stimuli that is to be generated by the Test Displays. The Visual Test software system also includes the Eye Movement Algorithm.

The Firmware system receives commands from the Visual Test software system and converts the commands to driver signals that are sent to the Test Displays such that light stimuli of a particular size, intensity, location and duration can be generated. If the Test Displays emit light in the red, green and blue spectrums then the Firmware system will command the Test Displays to generate light stimuli having those colours at the same brightness in order that the visual stimulus will appear as white or off-white. Moreover, the Firmware system will ensure that the appropriate pixels of the Test Displays are illuminated in order that the visual stimulus is presented at the correct location and is of the correct size, intensity and duration. If a clicker is used, the Firmware system may also register when the clicker was pressed by the patient and sends that information to the Visual Test software system.

The Statistical Analysis software system receives the test result data representing the lowest intensity at which the patient 214 saw a light stimulus or is inferred to have seen, if using a Bayesian algorithm, at each coordinate in the visual field that is tested. This Statistical Analysis software system then takes the test result data and adjusts the test result data in accordance with an age-based algorithm to generate adjust test result data. The adjusted test result data is then sent to the User Interface software system.

The User Interface software system performs several functions. Firstly, it receives the adjusted test result data from the Statistical Analysis software system and prepares a clinical report of the test results for use by a clinician or other medical professional. Secondly, the User Interface software system provides a user interface that may be accessed by the Technician 216*a* via the Technician Computer 208 such that the Technician 216*a* can administer the vision test. Thirdly, it permits the adjusted test result data to be stored in the Cloud or on an external storage device, such as a storage device associated with the Remote Server 112. Fourthly, the digital video feed may be viewed by the Technician 216*a* via the Technical Computer 208 when certain program instructions of the User Interface software system are executed by the main processor 304 of any given CU 102.

The CU Display UI software system controls the presentation of images on the CU Display 320.

Example of Method of Use

Figures 19, 20, 21:
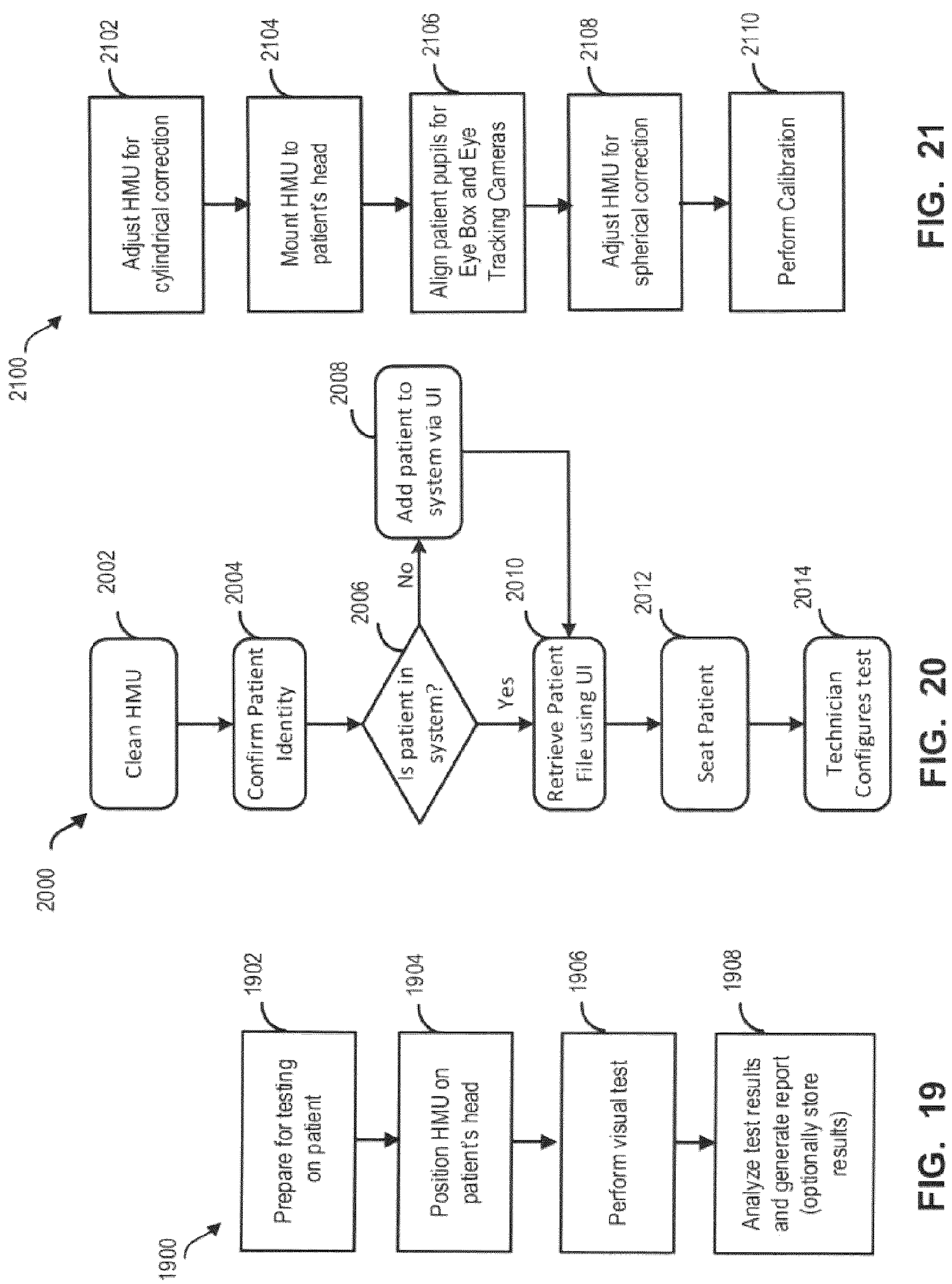
FIG. 19 illustrates an example embodiment of a process flow for a method for administering a vision test using a CU and an HMU.
FIG. 20 illustrates an example embodiment of a process flow for a method of setting up a vision test.
FIG. 21 illustrates an example embodiment of a process flow for a method for adjusting and securing an HMU to a patient.

Referring now to FIG. 19, shown therein is an example embodiment of a process flow for a method 1900 for administering a vision test using the CU 102 and the HMU 104 on the patient 214. At step 1902, the Technician 216*a* prepares for performing testing on the patient 214, which includes preparing the equipment and software for performing the correct vision test on the patient 214, such as the steps described in FIG. 20.

For example, referring now to FIG. 20, shown therein is an example embodiment of a process flow for a method 2000 of setting up a vision test. At step 2002, the HMU 104 is cleaned which may include disinfecting the HMU 104 and cleaning various surfaces including the eye piece 1016 and the Shell 601. At step 2004, the Technician 216*a* confirms the identity of the patient 214, such as through verbal communication.

At step 2006, the Technician 216 uses a user interface that is shown on the display of the Technician Computer 216 to determine whether the patient 214 is already in the test system (i.e. database) stored at the CU 102. The user interface on the Technician Computer 216 is generated by the User Interface Software system, which is executed by the main processor 304 of the CU 102. If a patient file for the patient 214 is in the test system then the method 2000 moves to step 2010 at which point the patient file for the patient 214 is retrieved using the user interface at the Technician Computer 208. At this point, the Technician 216*a* may edit the patient data in the patient file in order to update it if needed. If a patient file does not exist, then the method 2000 moves to step 2008 where the Technician 216*a* adds the patient 214 to the test system by including various information about the patient.

Figure 26:
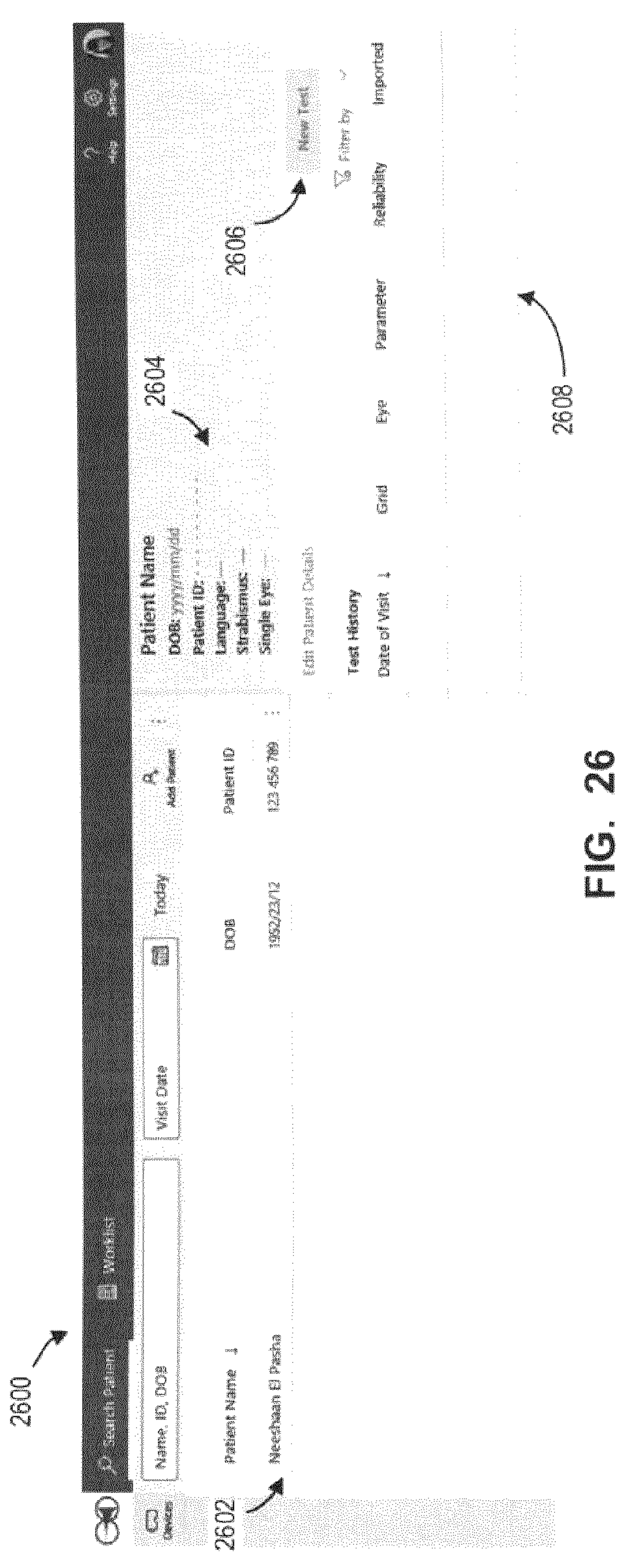
FIG. 26 illustrates an example embodiment for a first graphical user interface (GUI) used for selecting a patient for performing vision testing.

For example, referring now to FIG. 26, shown therein is an example embodiment of a GUI 2600 for selecting an existing patient file in which case all of the fields shown in FIG. 26 are filled out, or for entering a new patient field for performing vision testing in which case the fields shown in FIG. 26 are initially empty. The GUI 2600 includes a patient name field 2602 for the name of the patient 214 and patient information fields 2604 for inputting various information about the patient 214 such as, for example, patient date of birth, a patient ID number, languages spoken by the patient 214, health insurance information and patient eye health include any eye prescription data, and vision conditions such as strabismus, glaucoma and the like. This patient data may be inputted manually by the Technician 216*a* through the GUI 2600 at the Technician Computer 208 and stored in a database in the main memory 306 of CU 102. Alternatively, this patient data can be imported from another data base or work list. The Technician 216*a* may then either add the patient to a worklist in order to schedule the patient for testing at a later date or elect to administer a new test. For example, the New Test button 2606 in the GUI 2600 may be used for this purpose. There may also be a test history section 2608 showing test results for previous vision tests that were performed on the patient 214.

Figure 27:
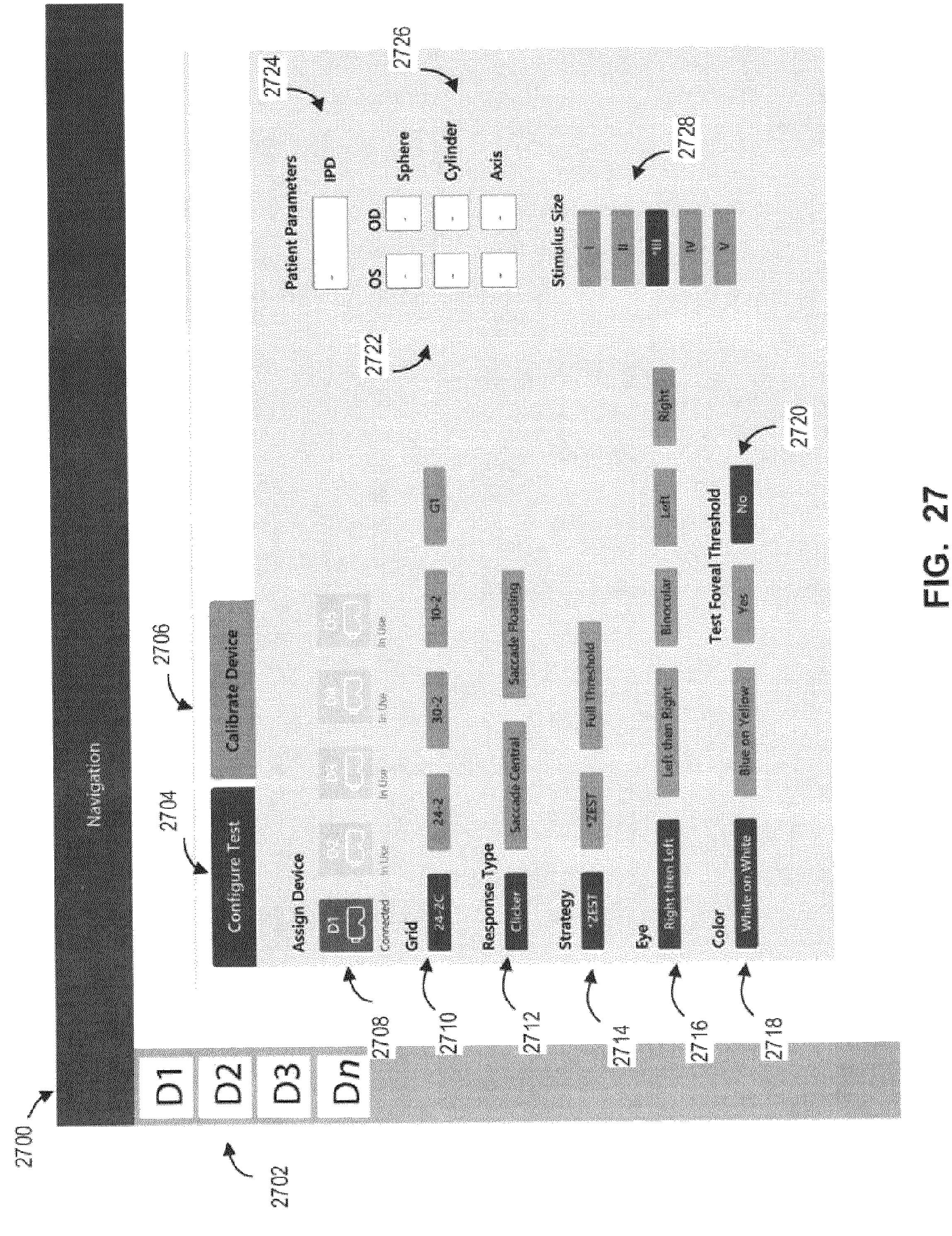
FIG. 27 illustrates an example embodiment for a second GUI used for configuring a vision test for the selected patient.

Referring back again to FIG. 20, at step 2012, the patient is seated in a test area, an example of which is shown in FIG. 2. At step 2014, the Technician 216*a* then configures the equipment for performing a new vision test. For example, the Technician 216*b* may select a vision test with parameters that have been previously stored in the patient file. Alternatively, the Technician 216*a* may select the test parameters in a user interface that is provided by the User Interface software system based on instructions from the Clinician. The Clinician instructions may include various parameters such as, but not limited to, the Standard Test to be performed; whether both eyes are to be tested at once; if the eyes are to be tested discretely which eye is to be tested first and which eye is to be tested second; whether an Eye Movement Test is to be conducted or a Clicker Test is to be conducted as illustrated in FIG. 27. Alternatively, in some embodiments, the Technician 216*a* may select a different type of vision test other than a visual field test. The Technician 216*a* may also input such patient data as IPD and error parameters.

For example, referring now to FIG. 27, shown therein is an example embodiment of a GUI 2700 that may be used for configuring a vision test for the patient 214. The GUI is shown on the Technician Computer 208 that is provided by the User Interface software system of the CU 102. It should be understood that the GUI 2700 is just one example of an interface that may be used and there may be other parameters, buttons and fields in alternative embodiments. For each selection option, they corresponding button or icon may be highlighted or shown in a different color.

The GUI 2700 includes an Available Devices area 2702 which shows the Visual Test Units which are available for testing. The GUI 2700 also has a Configure Test button 2704 which the Technician 216*a* may select for entering test parameters for the vision testing that is to be performed. The GUI 2700 also has a Calibrate Device button 2706 which the Technician 216*a* may select prior to performing vision testing for calibrating the select Visual Test Unit for testing on the patient 214. The Technician 2016*a* may perform calibration before or after entering the parameters for the vision testing.

The GUI 2700 includes a Device section area 2708 where the Technician 216*a* select one of the Visual Test Units for performing the vision test. The Visual Test Units that are not available for testing, since they may already be in use, are greyed out or otherwise indicated as not being available for use in the Device section area 2708.

The GUI 2700 also has a Grid Selection area 2710 that is used for selecting a grid that defines locations where the light stimuli are presented in the visual field of the patient 214. In this example, the available grids are the 24-2C, 24-2, 30-2, 10-2 and G1, but it should be understood that other grids may be available for selection in other embodiments.

The GUI 2700 also includes a Response Type area 2712 in which different options exist for how the vision test results data is obtained. For example, the Technician 216*a* may select the clicker option in which case the patient 214 depresses the clicker 218 every time that they see a visual stimuli. Alternatively, the Technician 216*a* may select the saccade central.

The GUI 2700 also includes a Test Strategy selection area 2714 where the Technician 216*a* may select the thresholding algorithm strategy. In this example embodiment, the test strategies include the ZEST or Full Threshold strategies. However, in other embodiments, other test strategies may be available for selection.

The GUI 2700 also includes an Eye selection area 2716 in which the Technician 216*a* can specify the eyes of the patient 214 that will be tested. For example, the Technician 216*a* may specify a sequence for testing both eyes (e.g., right then left or left then right), both eyes (e.g., a test of binocular vision), or only testing the left eye or only testing the right eye.

The GUI 2700 also includes a Color selection area 2718 and a Test Foveal Threshold area 2720. The Technician 216*a* can specify the particular colors that are to be generated for the visual stimuli in the Color section area 2718, which in this example includes White on White or Blue on Yellow. Other color options may be available in other embodiments. The Technician 216*a* can also specify whether or not to test a foveal threshold during the vision testing by selecting a YES or NO button in the Test Foveal Threshold area 2720.

The GUI 2700 also includes a Patient Parameters area 2722 which has a number of fields that the Technician 216*a* can use to enter data that is specific to the vision of the patient 214 being tested. For example, the Patient Parameters area 2722 includes an IPD field 2724 in which the Technician 216*a* can enter an IPD number for the patient 214*b*. The Patient Parameters area 2722 includes eye prescription fields 2724 for the OD (Oculus Dextrus—i.e., right eye) and the OS (Oculus Sinister—i.e. left eye) of the patient 214. The eye prescription fields 2724 include the sphere, cylinder and axis. The sphere indicates the strength of the prescription, the axis indicates an orientation of any astigmatism and the cylinder indicates the lens power that can be used to correct for the astigmatism, if any.

The GUI 2700 also includes a Stimulus Size area 2728 in which the Technician 216*a* can specify the size of the visual stimuli that are used in the vision testing. In this example embodiment, the stimulus size can be selected from I, II, III, IV and V.

Referring again to FIG. 19, the vision testing method 1900 now moves to step 1904 where the HMU 104 is positioned on the head of the patient 214 and properly mounted such that there is an alignment between certain electrical and optical components of the HMU and the eyes of the patient 214. This may be done by performing the steps shown in FIG. 21.

Referring now to FIG. 21, shown therein is an example embodiment of a process flow for a method 2100 for adjusting and securing the HMU 104 to the head of patient 214. The proper mounting of the HMU 104 on the patient 214 is advantageous to ensure that the patient 214 is seeing the visual stimuli in the correct locations (depending on the type of vision test selected) and that the eye movements of the patient 214 are properly recorded by the Eye Tracking Cameras 528 and 530.

At step 2102, the method 2100 involves adjusting the lens of the HMU 102 for spherical and cylindrical correction needed for the particular patient 214 that is being tested. For example, prior to placing the HMU 104 on the head of the patient 214, the Technician 216*a* will place the prescribed Cylindrical Correction Lenses 902 in the Cylindrical Correction Lens Mount 1004 mechanism as illustrated in FIGS. 9 and 13-15. The correct Cylindrical Correction lens 902 will be determined from the corrective prescription for the patient 214. FIGS. 16 to 18 illustrate alternative mounting structures for attaching and removing the Cylindrical Correction lens 902. This is done in advance of placing the HMU 104 on the head of the patient 214 as access to the Cylindrical Correction Lens Mount 904 is not possible once the HMU 104 is placed on the head of the patient 214.

The method 2100 then proceeds to step 2104 where the Technician 216*b* will then place the HMU 104 on the head of the patient 214. The Technician 216*b* will turn on the Eye Tracking Cameras 528 and 530 either by pressing a button on the interface of the CU 102 or by accessing the user interface provided by the User Interface software system using the Technician Computer 208. This will also turn on the LED Lights 816 in order to illuminate the area in front of the eyes of the patient 214. The Technician 216*b* will then be able to see the patient's eyes on the CU Display 320.

The method 2100 then proceeds to step 2106 where the Technician 216*b* will align the pupils of the patient 214*b* with the Eye Box and the Eye Tracking Cameras 528 and 530. To accomplish this, the CU Display 320 will indicate a target area where each pupil should be positioned in relation to the HMU 104 such that each pupil is correctly aligned with the light emanating from the Test Display and the Eye Tracking Camera for that eye. The target area is a representation of the Eye Box. The Technician 216*a* will then adjust the HMU 104 on the head of the patient 214 in order to achieve the correct alignment for both eyes of the patient 214 using the Head Band Adjustments Knobs 704 and 716 as well as the IPD Adjustment knob 716 as illustrated in FIG. 2 for patient 214*c*.

Figure 29:
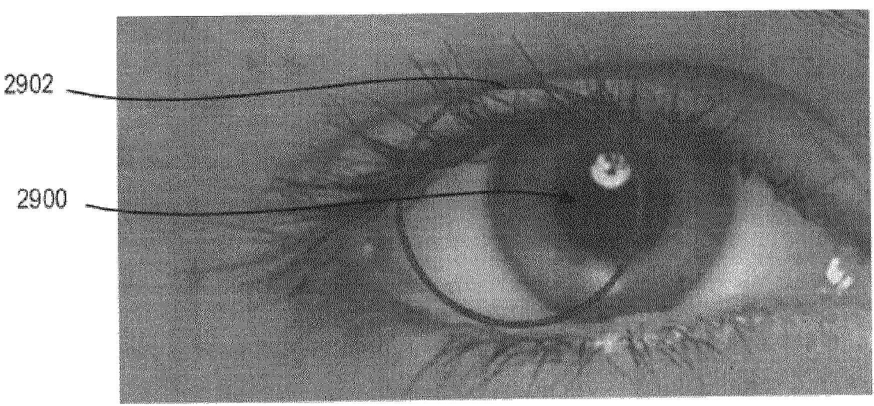
FIGS. 29 and 30 illustrate example of images of eye pupils that are shown on the display of the CU when the HMU is being mounted on a patient in which the HMU is not correctly mounted on the patient since the patient's eye pupil is not located within a reference template (i.e. circle) representing the correct location of the pupil such that the pupil is within an Eye Box and is properly aligned with an Eye Tracking Camera of the HMU.
Figure 30:
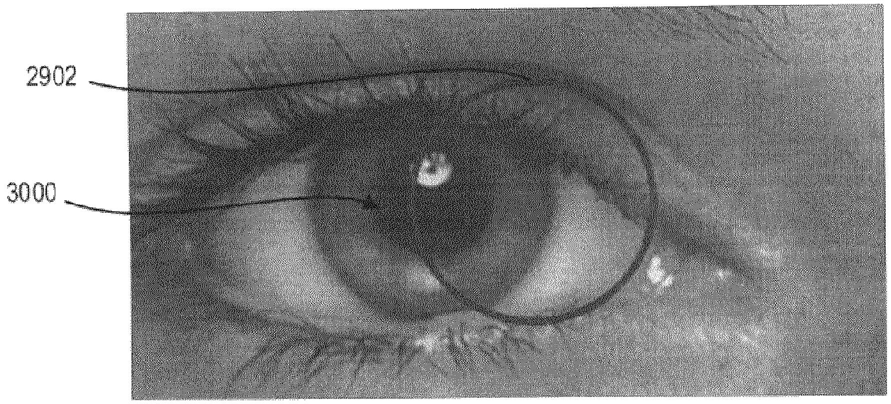
Figure 31:
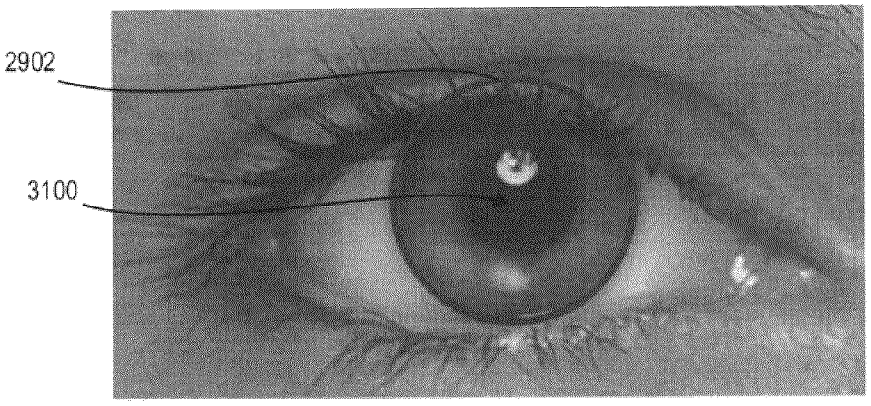
FIG. 31 illustrates an example image of an eye pupil that is shown on the display of the CU when the HMU is being mounted on a patient in which the HMU is properly mounted on the patient since the patient's eye pupil is correctly aligned with a reference template that represents the correct location of the pupil such that the pupil is within the Eye Box and is properly aligned with the Eye Tracking Camera of the HMU.

For example, referring now to FIGS. 29-31, during HMU 104 positioning, the Technician 216*b* is viewing a display of the patient's eye on the CU Display 320 and adjusting the HMU position such that the pupil of the patient 214 is located within a visual representation 2902 (i.e., reference template) of the Eye Box, which in this example is a circle. For example, after an initial positioning of the HUM 104 on the head of the patient 214, the position 2900 of the pupil of patient 214 may not be centered within Eye Box representation 2902 since in this case the pupil is offset to the right of the Eye Box representation 2902. The Technician 216*b* then readjusts the position of the HMU 104 on the head of the patient 214 and may still not correctly align the pupil with the Eye Box representation 2902 as shown in FIG. 30, in which the pupil is offset to the left of the Eye Box representation 2902. The Technician 216*b* continues to adjust the position of the HMU 104 until the center of the pupil is at position 3100 which is at approximately the center of the Eye Box representation 2902. The location of the pupil is now centered within the Eye Box and is properly aligned with the Eye Tracking Camera of the HMU 104.

The method 2100 then proceeds to step 2108 where the HMU 104 is adjusted for spherical correction. The Technician 216*a* will adjust the spherical correction, if needed, in accordance with the corrective prescription of the patient 214 by adjusting the Spherical Lens Focus Adjustment Ring 606 (see FIGS. 10 and 606 FIG. 6) and viewing the Spherical Lens Focus Scale 1002 as illustrated in FIG. 10 through the Lens Focus Scale View Point 602 as illustrated in FIG. 6. The Spherical Lens Focus Adjustment Ring 606 is adjusted until the Spherical Lens Focus Scale 1002 indicates the spherical correction in the corrective prescription of the patient 214.

The method 2100 then proceeds to step 2110 since prior to the commencement of each vision test the pupil's position and certain electronics of the HMU 102 are calibrated. This is done by requiring the patient to look at an icon in the middle of the visual field and at each corner of the visual field. The Eye Tracking software system records these eye movements in order to correctly determine the pupil position.

Figure 28:
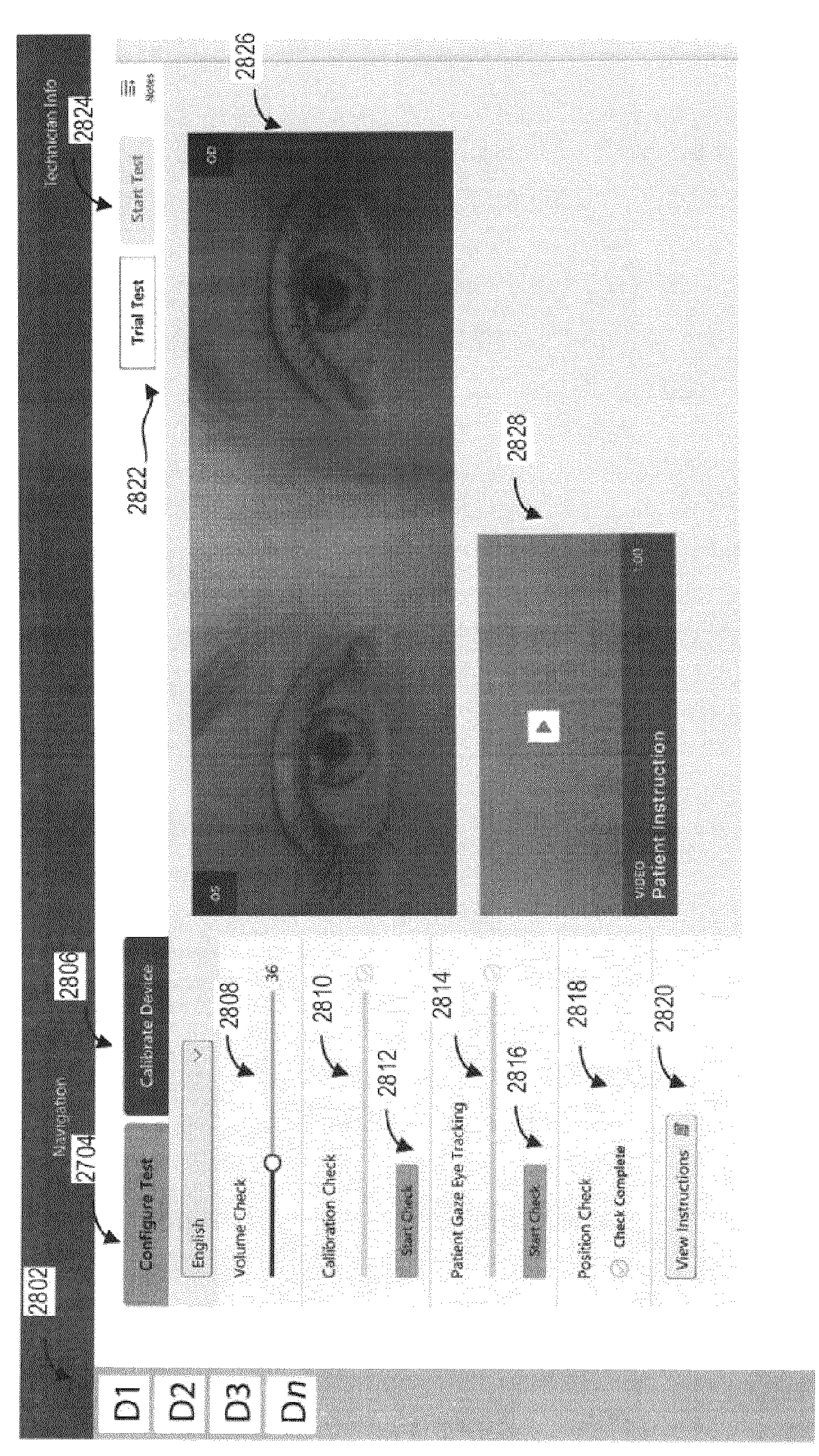
FIG. 28 illustrates an example embodiment for a third GUI used for performing calibration before performing the vision test for the selected patient.

For example, referring now to FIG. 28, shown therein is an example embodiment of a GUI 2800 for performing calibration before performing the vision test for the patient 214. The GUI 2800 includes an Available Devices area 2802, a Configure Test button 2804 and a Calibration Device button 2806, which all function similarly to the Available Devices area 2702, the Configure Test button 2704 and the Calibration Device button 2806, respectively, that were described earlier. It should be understood that the GUI 2800 is just one example of an interface that may be used for calibration and there may be other parameters, buttons and fields in alternative embodiments.

The GUI 2800 includes a Volume Check slider 2808 which can be used to adjust the volume of the audio, including verbal instructions, that are provided to the patient 214 through the headphones 714 of the HMU 104. For example, if the patient 214 is elderly or otherwise hard of hearing the volume can be increased by adjusting the Volume Check slider.

The GUI 2800 includes a Calibration Check status bar 2810 and a Start Calibration Check button 2812. When the Technician 216*a* wants to start calibration, they can select the Calibration Check button 2812. A calibration process is then performed and the amount of the calibration that is completed can be indicated by the Calibration Check status bar 2810.

The GUI 2800 includes a Patient Gaze Eye Tracking status bar 2814 and a Start Patient Gaze Eye Tracking button 2816. The Technician 216*a* can select the Start Patient Gaze Eye Tracking button 2816 to begin testing the Eye Tracking Cameras 528 and 530 for properly tracking the eyes of the patient 214. For example, a testing protocol may be performed for testing the Eye Tracking Cameras 528 and 530. The Patient Gaze Eye Tracking status bar 2814 indicates the amount of calibration that has been done on the Eye Tracking Cameras 528.

The GUI 2800 includes a Position Check area 2818 which indicates whether the HMU 102 has already been positioned properly on the head of the patient 214 so that the pupils of the patient's eyes are properly positioned at the Eye Box area of the HMU 104. If this has already been done then the Check Complete radio button will be checked. If the Check Complete radio button is not checked then the Technician 216*a* will have to go through the steps for properly mounting the HMU 104 on the head of the patient 214 as described previously.

The GUI 2800 includes a View Instructions button 2820 which may be selected by the Technician 216*a* for showing an instructional video to the patient 214. If the Technicians 216*a* selected the View Instructions button 2820 then the instructional video that is shown to the patient via the Test Displays 514 and 518 is also shown in the Patient Instruction video area 2828 of the GUI 2800. The Technician 216*a* may also provide test instructions to the patient 214 via an audio set of instructions that will be provided to the patient through the Speaker Headphones 714 of the HMU 104.

The GUI 2800 includes a Trial Test button 2822 that is used for starting the trial test.

The GUI 2800 includes a Start Test button 2824 that is used for to start the visual test.

The GUI 2800 also includes an Eye Display window 2826 that shows a video feed of the eyes of the patient 214 that were captured using the Eye Tracking Cameras 528 and 530. The Technician 216*a* can view the eyes of the patient 214*b* in the Eye Display window 2826 for to ensure that the patient's eye have remained centered on the Eye Tracking Cameras.

Referring again to FIG. 19, after calibration is successfully performed, the vision testing method 1900 moves to step 1906 where the Technician 216*a* starts to perform the vision test on the patient 214. At this point, the Technician 216*a* may commence the vision test either by depressing a button on the CU 102 or by using a GUI provided by the User Interface software system accessed by the Technician Computer 208.

During the test, the Technician 216*a* can monitor the vision test by viewing the eyes of the patient 214 either on the CU Display 320 or on a GUI shown on the display of the Technician Computer 208 and provided for by the User Interface software system of the CU. The GUI can also provide an image depicting the coordinates for which vision test result data has been collected.

Figure 32:
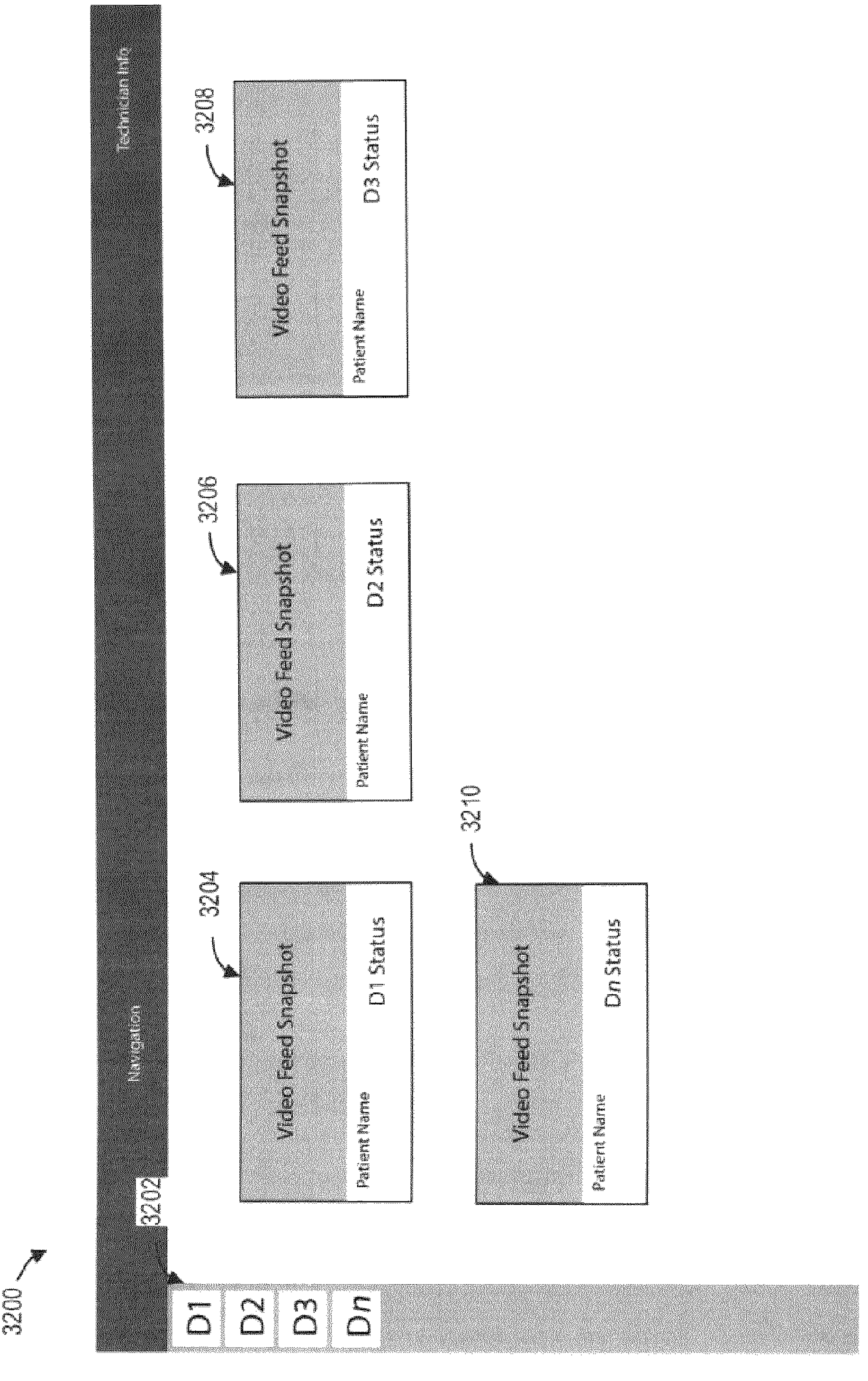
FIG. 32 illustrates an example embodiment for a fourth GUI used for reviewing different vision tests that are being performed at the same time.

For example, referring now to FIG. 32, shown therein is an example embodiment for a GUI 3200 for monitoring the progress of a vision test. In particular, GUI 3200 allows for monitoring several vision tests that are being performed at the same time. The GUI 3200 has an Available Devices area 3202 that shows the number of Visual Test Units as well as several patient monitoring areas including a first patient monitoring area 3204, a second patient monitoring area 3206, a third patient monitoring area 3208 and a fourth patient monitoring area 3210. A patient monitoring area can be shown for each vision test that is currently being performed. In this case there are four vision tests being performed in parallel. In this example embodiment, each patient monitoring area shows the patient name, the status of the Visual Test Unit and a video feed showing the eyes of the patient 214 during testing.

Depending on the specific Standard Test selected and other parameters such as the eyes to be tested, once the vision test is started, such as by selecting the "Start Test" button 2824 in FIG. 28, the software code for the vision testing program that is part of the Visual Test software system will be executed by the main processor 304 and a command will be sent to the Firmware system executed by the processor 504 at the HMU 104 to present a light stimulus at a predetermined coordinate in the visual field eccentric to the central fixation point where the light stimulus will have a particular size, intensity and duration. The processor 504, executing the Firmware, will then convert that command into driver signals so that one or both of the Test Displays 514 and 518 present such light stimulus as described above to the eyes of the patient 214. If both eyes are being tested, then both Test Displays 514 and 518 are activated but the light stimuli are presented on only one of the Test Displays 514 and 518 at a time. The light stimuli are presented randomly on one Test Display or the other. If only one eye is being tested then only the Test Display that is aligned with that eye presents the light stimuli.

Figure 24:
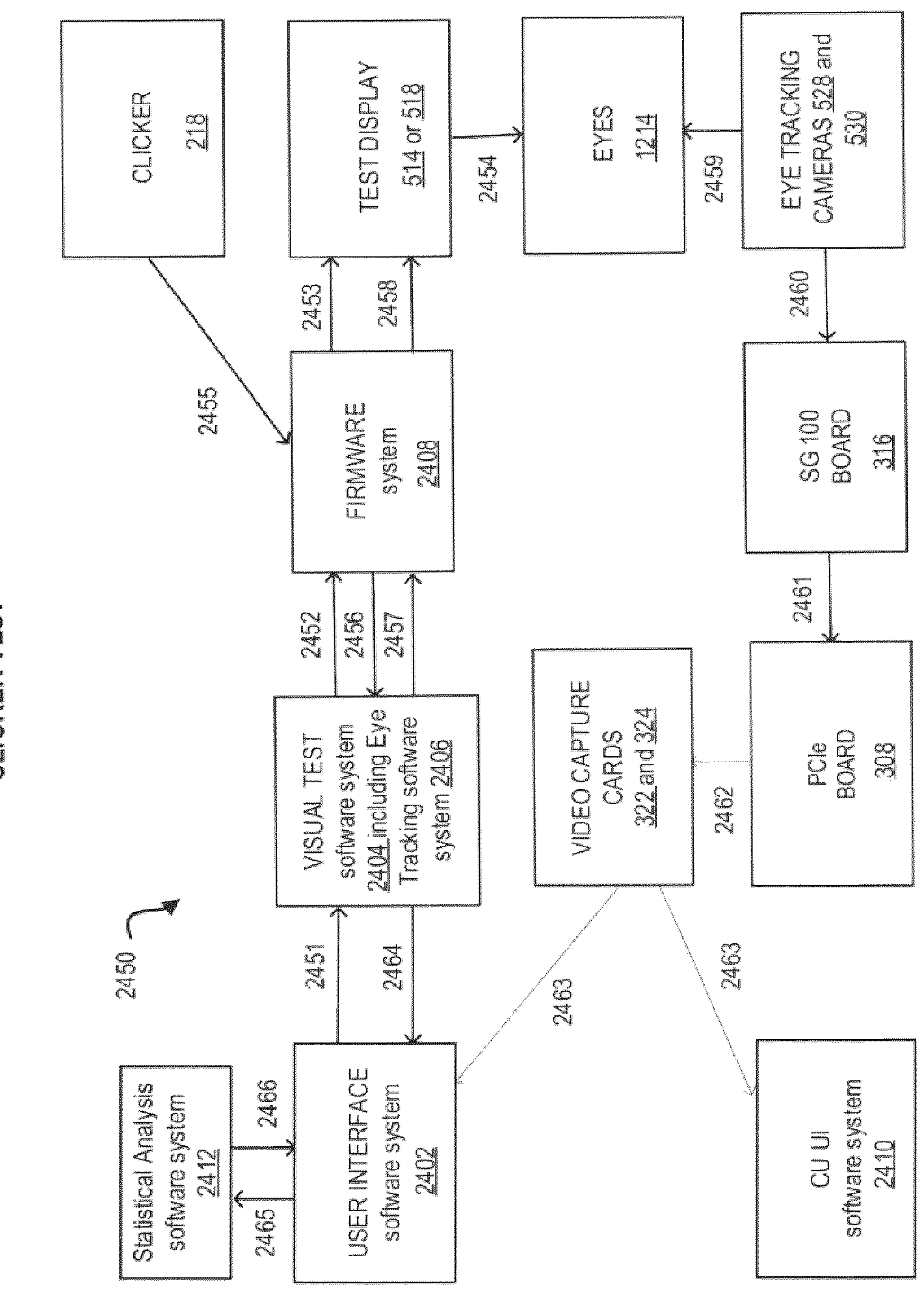
FIG. 24 illustrates a flow chart of an example embodiment of a process and associated actions for performing a Clicker Test.

For example, if a Clicker Test is being conducted and if the patient 214 sees the light stimulus, the patient 214 will indicate recognition of the light stimulus by depressing the clicker 218. The processor 504, by executing the Firmware, will then send test result data indicating the depressing of the clicker 218 to the CU 102 where it is analyzed by the main processor 304 according to the software instructions of the Visual Test software system. The main processor 304 will then send a command to the processor 504, which through the Firmware, will drive the appropriate Test Display 514 or 518 to present a second light stimulus at the same location but at a lower intensity. Alternatively, if the patient failed to depress the clicker 218, then the main processor 304, in accordance with the instructions of the Visual Test software system, will then send another command to the processor 504, which through the Firmware, will drive the appropriate Test Display 514 or 518 to generate a second light stimulus to be presented at the same location to the patient 214 but at a higher intensity. This process will be repeated until the patient 214 does not see a given light stimulus that was presented but has seen the light stimulus of slightly higher intensity. The minimum luminosity at which the patient saw the stimulus is herein referred to as the "Minimum Luminosity Level". An example of the operations that are performed during the Clicker Test are also shown in FIG. 24.

In some embodiments, a bracketing strategy will be used to refine the Minimum Luminosity Level. Alternatively, in some embodiments, the light stimulus may be presented not consecutively at the same location in the visual field but intermittently at the same location. Alternatively, in some embodiments, the luminosity levels of the light stimuli that are presented to the patient 214 may be selected in accordance with a Bayesian algorithm taking into account the various factors to determine the probability that the Minimum Luminosity Level will be of a particular luminance and therefore the most efficient series of light stimuli presentations are performed to determine the Minimum Luminosity Level.

Figure 25:
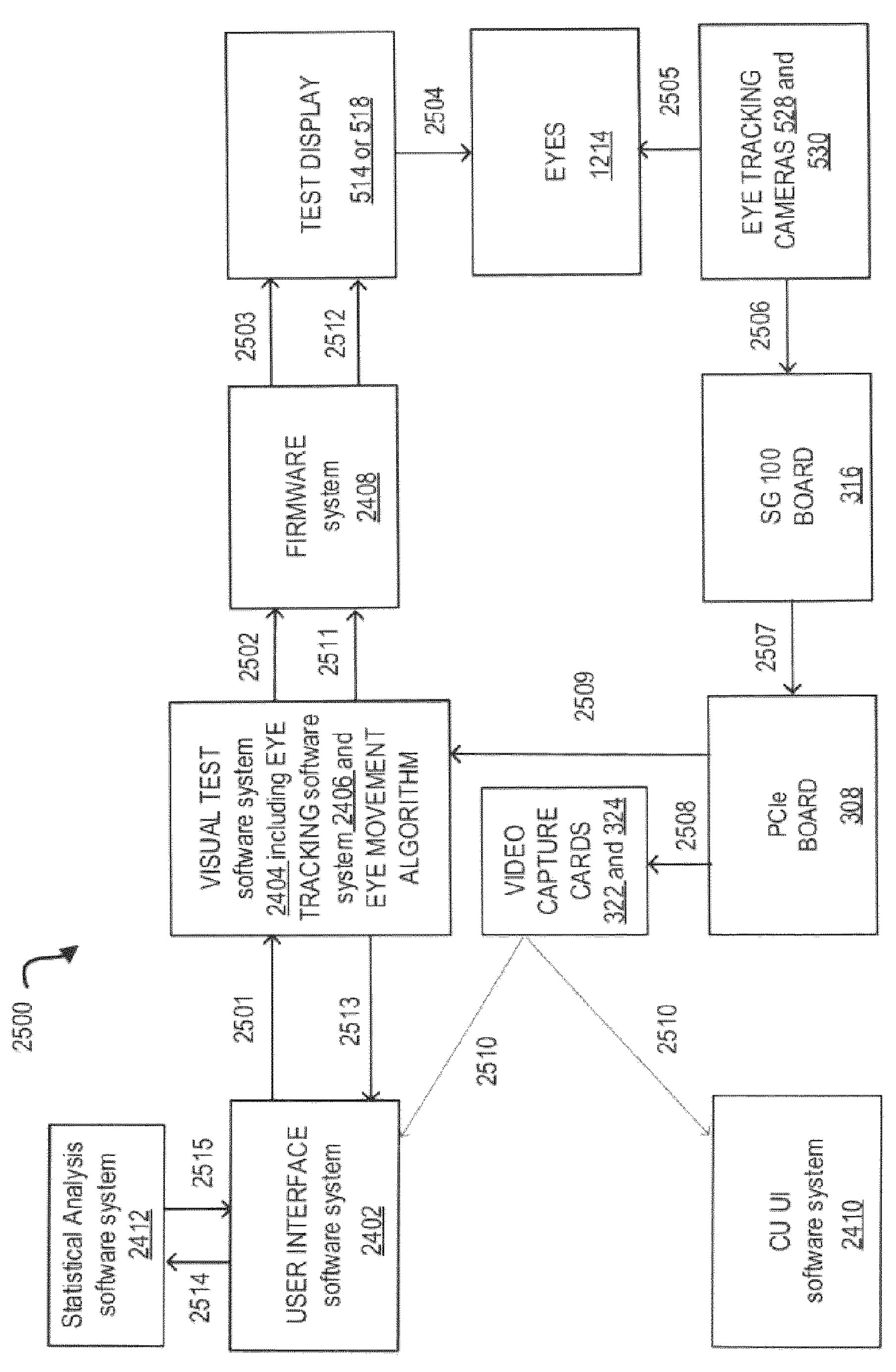
FIG. 25 illustrates a flow chart of an example embodiment of a process and associated actions for performing an Eye Movement Test.

Alternatively, if an Eye Movement Test is being conducted, the following process for determining a Responsive Eye Movement will occur according to one example embodiment. The Eye Tracking Cameras 528 and 530 will record the eye movements of the patient 214 during the vision testing. The Eye Tracking Cameras 528 and 530 will provide image data which includes gaze data of the patient 214 every few milliseconds. For example, if 250 Hz cameras are being used, gaze data will be obtained every 4 milliseconds. A video feed consisting of the image data, generated by the Eye Tracking Cameras 528 and 530, of the eyes of the patient 214*b* will be transmitted to the SG100 Board 316 in the CU 102. In some embodiments, the video feed from the Eye Tracking Cameras 528 and 530 will already be in digital format so that a conversion of the feed from analog to digital format as described below will not necessary. Then two parallel operations may occur. Firstly, the PCIe Board 308 has electronic components that converts the analog video feed into binary data representing the location of the pupils over time which is herein referred to as gaze data. The gaze data, inter alia, identifies the pupil location over time by providing the x and y axis of the pupils along with the timestamps. The gaze data is then analyzed by the main processor 302 when executing certain program instructions of the Visual Test software system including the Eye Movement Algorithm which is described in further detail below. Secondly, without converting the digital video feed into numeric binary data, the PCIe Board 308, will send the analog video feed to the two Video Capture Cards 322 and 324 (one for each camera feed). The Video Capture Cards 322 and 324 will then convert the analog video feed into digital video feed and then send that digital video feed to both the CU Display 320 and the main processor 304. The main processor 304, while executing certain program instructions of the Visual Test software system, will then use the binary data received from the PCIe Board 308 to determine whether or not a Responsive Eye Movement has occurred in response to a particular light stimulus in accordance with the Eye Movement Algorithm as described below. The various electronic components of the CU 102 and the HMU 104, as per software instructions of the Visual Test software system will then proceed to follow the same process as described above for the Clicker Test to determine the Minimum Luminosity Level at each location tested except that the recognition by the patient of each light stimulus will be determined on the basis of whether or not a Responsive Eye Movement has occurred rather than on the basis of whether or not the patient 214 has depressed the clicker 218. An example of the operations that are performed during the Eye Movement Test are also shown in FIG. 25.

By the end of the Eye Movement Test, a numerical value will be assigned to each coordinate that is tested indicating the Minimum Luminosity Level at that location. Those numerical values, collectively referred to as vision test results data, may be stored at the main memory 306 of the CU 102 and sent in real time by the Visual Test System to the User Interface System. Alternatively, in some embodiments, all the vision test results data will be stored in the main memory 306 of the CU 102 and then upon the completion of the vision test all of the vision test results data will be sent by the Visual Test System to the User Interface System. In either case, the User Interface System will then send the vision test results data to the Statistical Analysis software system for adjustment in accordance with an aged based algorithm and to perform other statistical analysis to enable the User Interface software system to produce a variety of test reports.

At any point in the vision test, the vision test may be paused, either because the patient 214 is not fixated on the central fixation point when they should be so fixated or because their head tilt has gone beyond a specified limit, as will now be described.

Once the vision test is concluded then the method 1900 will move to step 1908 where the test results are analyzed and a test report is generated.

User Interface software system will then use the adjusted numerical values to prepare a report for the clinician. As described previously, the report is generated using a format that is conventionally used by clinicians so that they can easily interpret the results. Also, before the report is generated, the Statistical Analysis software system receives the test result data and performs an adjustment in accordance with an age-based algorithm to generate adjust test result data. A person of skill in the art will know the age-adjustments that are performed. The report is based on the adjusted test result data. The test result data and the test report can be stored at the CU 102 and/or the remote server 112.

Example Embodiment to Prevent Excessive Head Tilt During Testing

It has been determined that a head tilt of the patient 214 greater than a certain amount, such as about 20 degrees off of vertical, will affect the accuracy of the vision test results. Accordingly, in at least one embodiment described herein, the Visual Test software system includes software code that is executed by the main processor 304 for routinely checking the head tilt of the patient 214 and pausing the vision test once the head tilt exceeds a predefined head tilt threshold, e.g. about 20 degrees off absolute vertical or off of the patient's normal head tilt, for more than a predefined heat tilt time limit.

Figure 22:
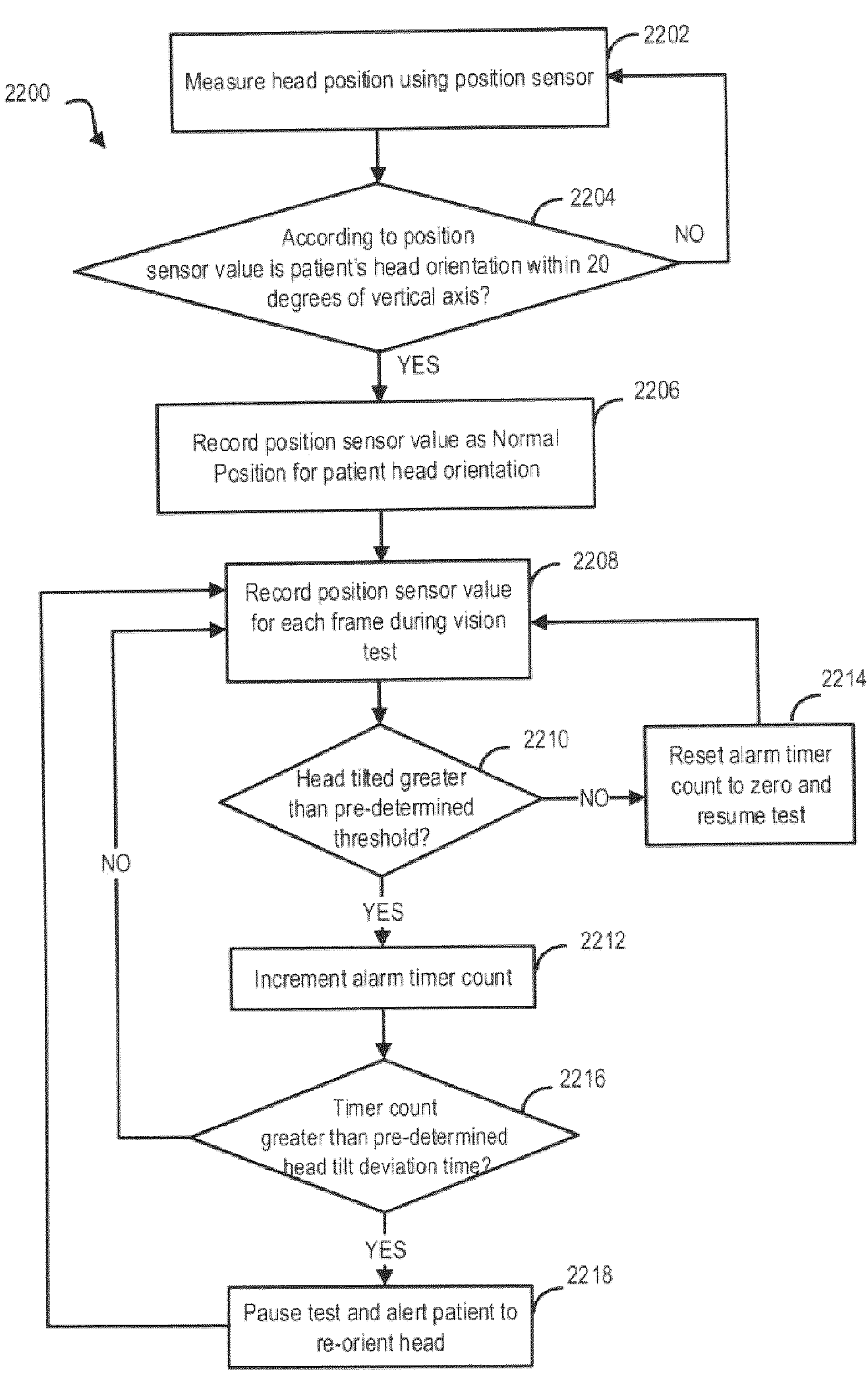
FIG. 22 illustrates an example embodiment of a process flow for a method for determining and preventing over-tilting of a patient's head during a vision test.

Referring now to FIG. 22, shown therein is an example embodiment of a method 2200 that may be used to prevent excessive head tilt.

Since each patient's normal head position is normally not completely vertical the position sensor, which may be a gyroscope or an accelerometer, initially records the natural position of the head of the patient 214 in terms of x,y and z values at step 2202 while the patient 214 is seating relaxed. This position is referred to herein as the "Normal Position" and it is one of the positions from which the head tilt may be determined, the other being absolute vertical. The patient 214 preferably keeps their head tilt within a predefined head tilt threshold of both the Normal Position and absolute vertical during vision testing.

The position sensor provides a continuous feed of data to the Visual Test software system indicating the location of the head of the patient 214 in terms of the x,y and z axis. At step 2202 a first position value is measured using the position sensor. At step 2204, it is determined whether the position value is within about 20 degrees of the vertical axis (i.e., absolute vertical). If this is true then at step 2206, the position value is recorded as the Normal Position value for the patient 214. If this condition is not true then the patient 214 is instructed to keep their head more "vertically straight" and the method 2200 returns to step 2202 to record another position value. Steps 2202 and 2204 are repeated until a Normal Position value is determined and recorded at step 2206. It should be noted that steps 2202 to 2206 may be performed during calibration.

After the Normal Position value is determined, then just as vision testing starts an alarm timer count is set to zero and during vision testing the method 2200 cycles through steps 2208 to 2218 to monitor the head tilt of the patient 214 to make sure that the head tilt is not greater than about 20 degrees of the Normal Position or absolute vertical for a certain period of time.

In this example embodiment, step 2208 involves measuring the current position value of the head of the patient 214. Step 2202 then determines whether the current position value is greater than the pre-determined head tilt threshold, i.e., about 20 degrees. If the current position value indicates a head tilt that is less than about 20 degrees from the Normal Position or 20 degrees from absolute vertical, then the method 2200 proceeds to step 2214 where the alarm timer count is set to zero and the method 2200 proceeds to step 2208. However, if it is determined at step 2210 that the current position value is greater than about 20 degrees from the Normal Position or 20 degrees from absolute vertical, then the method 2200 proceeds to step 2212 where the alarm timer count is incremented. The method 2200 then proceeds to step 2216 where it is determined whether the deviation of the head position from more than about 20 degrees from the Normal Position or absolute vertical, persists for a period of time greater than a predetermined maximum period of time, i.e. a predetermined head tilt deviation time. If the determination at step 2216 is true, then the method 2200 proceeds to step 2218 where the vision test is paused and the patient 214 is instructed to straighten their head position. The vision test will only recommence once the position of the head of the patient 214 is within 20 degrees of the Normal Position and 20 degrees of absolute vertical.

Example Embodiment to Monitor Fixation During Testing

As explained above, one source of error of visual field tests arises from the patient 214 losing fixation on a central fixation point during the vision test. In the case of an Eye Movement Test, the test commences with the patient 214 fixated on the central fixation point but then the patient 214 is encouraged to move their gaze towards light stimuli as they are presented. After each eye movement, the patient 214 must regain fixation on the central fixation point before the next light stimulus is presented.

Accordingly, in at least one embodiment described herein, the Test Displays 514 and 518, under the control of the Firmware system based on instructions from the Visual Test software system, will not present a light stimulus unless the patient 214 is fixated on the central fixation point. As described above, the Visual Test software system receives a flow of pupil location measurement samples of the location of the pupil throughout the Eye Movement Test. The Visual Test software system includes software code for setting a predetermined gaze limit threshold from the center of the central fixation point, e.g. coordinate 0/0. This limit is referred to herein as the "Gaze Limit Threshold". If a current gaze, based on a current pupil location measurement, is outside the Gaze Limit Threshold then the next light stimulus in the visual test will not be presented. During the Eye Movement Test, if the current gaze of the patient 214 is outside of the Gaze Limit Threshold for a minimum specified period of time then it is determined that the patient 214 has lost fixation and the Eye Movement Test is paused until such time as the patient 214 regains fixation by redirecting their gaze to a point within the Gaze Limit Threshold of the central fixation point.

Figure 23:
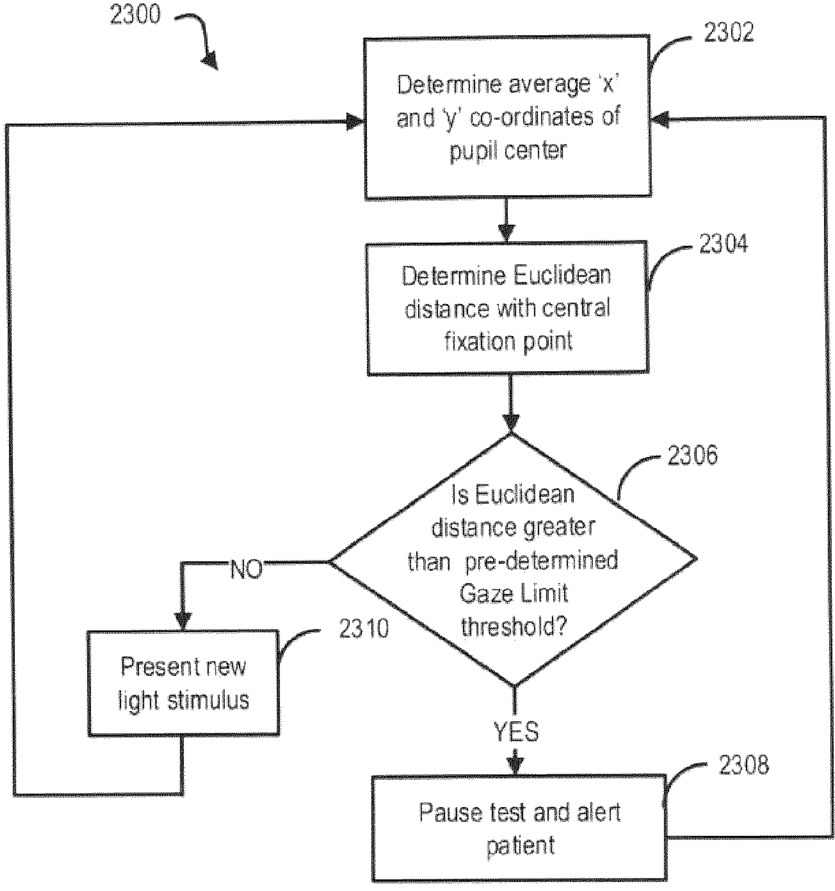
FIG. 23 illustrates an example embodiment of a process flow for a method for determining a patient's loss of fixation on a central fixation target during a vision test.

Referring now to FIG. 23, shown therein is an example embodiment of a method 2300 for determining a patient's loss of fixation on a central fixation target during an Eye Movement Test. During the method 2300, the Eye Tracking Cameras 528 and 530 provide a video feed of images which are analyzed to determine a series of x and y coordinates representing the pupil location measurements over time. The method 2300 is employed by the Visual Field software system to continuously obtain the pupil location measurements to determine if the gaze of the patient 214, based on the location of the pupil, is within the Gaze Limit Threshold.

At step 2302, the current gaze is determined based on the average 'x' and 'y' co-ordinates of the center of the pupil that are obtained over a predetermined number of images obtained during a certain time period. At step 2304, the distance (e.g., Euclidean distance) between the average 'x' and 'y' coordinates and the position of the central fixation is determined. In some cases, the central fixation point may be allocated the central co-ordinates (0,0).

At step 2304, it is determined whether the current gaze of the patient 214 is outside of the Gaze Limit Threshold beyond a specified time limit. If this is true, then the method 2300 moves to step 2308 where the Eye Movement Test is paused and the patient 214 is advised, such as by the audio system, to return their gaze to the central fixation point. In some embodiments, an alarm may also sound and the Technician **216*a* is advised of the issue at the Technician Computer 208 through the User Interface software system. If the determination at step 2306 is negative then the method 2300 moves to step 2310 where a new light stimulus is presented to the patient 214. After step 2308 and 2310 are performed, then the method 2300 moves to step 2302 where the current gaze is determined and steps 2306 and either step 2308 or step 2310** is performed.

Example Embodiment of how Eye Movements are Tracked Taking Blinks into Account

If one does not take eye blinks into account then a false negative may occur in that the patient 214 does not see a light stimulus simply because it occurred when the patient's eye was closed rather than because of some visual field defect. In order to eliminate or reduce such false negatives from occurring, in at least one embodiment of the invention, the Eye Tracking software system sends data through to the Visual Test software system for indicating when a blink has occurred based on the amount of pupil visible in the video images obtained by the Eye Tracking Cameras 528 and 530. The Eye Movement Algorithm will then determine if the blink occurred within a certain time window after presentation of a light stimulus. If it did, then the Visual Test software system will send a command to the Firmware system to command one or both of the Test Displays to re-present the same light stimulus. Alternatively, in at least one embodiment of the invention, the Eye Tracking System will not present a stimulus during a blink as it will determine that the patient is not fixated on the central fixation point.

Eye Movement Algorithm as Used in the Clicker Test

The Eye Movement Algorithm is not used in the Clicker Test except to carry out Fixation Monitoring. During the Clicker Test, the patient is required to maintain fixation of the central fixation point throughout the test. If the patient loses fixation during the test then the next stimulus is not presented until the patient regains fixation in the same manner as the Eye Movement Test. In addition, if the patient blinks then the Eye Tracking Algorithm will not present a new stimulus until the patient has regained fixation.

Example Embodiment of the Clicker Test

Referring now to FIG. 24, shown therein is an example embodiment of a flow diagram showing how various components of the CU and the HMU operate when performing a method 2450 for implementing the Clicker Test. It should be understood that there may be other embodiments in which the software systems may operate differently; however, the overall effect is the same.

The Clicker Test method 2450 begins at step 2451 where the User Interface software system 2402 sends one or more commands to the Visual Test software system 2404 to conduct one of the Standard Tests by using a Clicker Test in accordance with certain parameters described herein such as testing one or both eyes, for example.

The method 2450 then proceeds to step 2452 where The Visual Field software system 2406 includes software instructions for configuring the main processor 304 to determine the location, luminosity, size and duration of the initial light stimulus and then sends stimulus commands the Firmware system 2408 to generate that particular light stimulus for presentation to the patient 214.

The method 2450 then proceeds to step 2453 where the Firmware system 2408 includes software instructions for configuring the processor 504 to re-configure the stimulus commands into driver commands so that one or both of the Test Displays 514 or 518 are driven to illuminate pixels thereon to generate the light stimulus which then propagates along the corresponding Lens Stack to present the stimulus to the patient 214 as directed.

The method 2450 then proceeds to step 2454 where the patient 214 either sees the light stimulus or does not see the light stimulus or commits a False Positive Error or a False Negative Error and consequently either depresses the clicker button or fails to depress the clicker button on the clicker 218.

The method 2450 then proceeds to step 2455 where if the clicker 218 is depressed then a clicker signal is sent to the Firmware system 2408.

The method 2450 then proceeds to step 2456 where the Firmware system 2408 includes software code for configuring the processor 504 to send a clicker event signal to the Visual test software system 2404 where the clicker event signal includes data indicating that the clicker 218 was depressed at a particular point in time.

The method 2450 then proceeds to step 2457 where in the event that the clicker 218 was not depressed within a predetermined time response window but the Eye Movement Algorithm, via implementation by the main processor 304, determines that an eye blink has occurred within the predetermined time response window of the presentation of the light stimulus then the Visual Test software system 2404 will configure the main processor 304 to command the Firmware system to re-present the light stimulus since the patient 214 may not have seen the light stimulus due to an eye blink. In the event that the clicker 218 was not depressed and no eye blink had occurred within the predetermined time response window of the presentation of the light stimulus, then the Visual Test software system 2404, via the Visual Test software system, determines that there was no recognition of the light stimulus by the patient 214 and accordingly the Visual Test software system 2404 configures the main processor 304 to send another stimulus command to the Firmware system 2408 so that one or both of the Test Displays present a light stimulus of a higher intensity to the patient 214. If the clicker 218 was depressed within the predetermined time response window then the Visual Test software system records this response as recognition of the light stimulus and accordingly configures the main processor 304 to send a stimulus command to the Firmware system 2408 to present the next light stimulus at a lower intensity level.

The method 2450 then proceeds to step 2458 where (8) the Firmware system 2408 includes software instructions for configuring the processor 504 to re-configure the new stimulus commands into driver commands so that one or both of the Test Displays 514 or 518 are driven to illuminate pixels thereon to generate the next light stimulus so that it propagates along the corresponding Lens Stack to be presented to the patient 214 and so on. Step 2455 may then be repeated.

While the Clicker Test is being conducted, the method 2450 also performs another series of steps in parallel including steps 2459 to 2463. At step 2459, as the various light stimuli are being generated by one or both of the Test Displays 514 and 518, in accordance with the Clicker Test protocol, the Eye Tracking Cameras 528 and 530 are creating a video feed of video images of the eyes of the patient 214. The video feed is in an analog format and it is continuously sent to the SG100 Board 316 at step 2460. Alternatively, the video feed may be in digital format depending on the type of Eye Tracking Cameras 528 and 530 that are used.

The method 2450 then proceeds to step 2461 where the SG100 Board sends the analog video signal to the PCIe Board 308.

The method 2450 then proceeds to step 2462 where the PCIe Board 308 in turn sends the analog video feed continuously to the Video Capture Cards 322 and 324 that convert the analog video feed to digital video feed and then at step 2463 send that digital video feed to both the User Interface software system 2402 for displaying the video feed at the Technician Computer 208 for viewing by the Technician **216*a* and the Control Unit User Interface software system 2410 for displaying the video feed on the CU Display 320 for viewing by the Technician 216*b***.

Once the Clicker Test is completed, or alternatively during the performance of the Clicker Test, the method 2450 proceeds to step 2464 where the Visual Test software system 2404 sends the test result data that includes numeric values representing the Minimum Luminosity Level for each coordinate that was tested to the User Interface software system 2402.

The method 2450 may then proceed to step 2465 where the test result data is sent to the Statistical Analysis software system 2412 from the User Interface software system 2402. At step 2466, the test result data may be adjusted for age according to an aged-based algorithm described herein. The adjusted test result data is then sent back to the User Interface software system 2402 which will then use the age-adjust test result data to generate a clinical test report for viewing by a clinician and/or eye doctor.

Example Embodiment of the Eye Movement Test

Referring now to FIG. 25, shown therein is an example embodiment of a flow diagram 2500 for performing an Eye Movement Test method 2500 using the CU 102 and the HMU 104. It should be understood that there may be other embodiments in which the software systems may operate differently; however, the overall effect is the same.

The Eye Movement Test method 2500 begins at step 2501 where the User Interface software system 2402 send one or more commands to the Visual Test software system 2404 to conduct one of the Standard Tests by using an Eye Movement Test in accordance with certain parameters as described herein such as testing one or both eyes, for example.

The Eye Movement Test method 2500 then moves to step 2502 where the Visual Field software system 2404 includes software instructions for configuring the main processor 304 to determine the location, luminosity (otherwise referred to as "intensity") size and duration of the initial light stimulus and then sends a corresponding stimulus command to the Firmware system 2408 to generate that particular light stimulus for presentation to the patient 214.

The Eye Movement Test method 2500 then moves to step 2503 where the Firmware system 2408 includes instructions for configuring the processor 504 to re-configure the stimulus command into driver commands so that one or both of the Test Displays 514 or 518 are driven to illuminate pixels thereon to generate the light stimulus which then propagates along the corresponding Lens Stack to present the stimulus to the patient 214 as directed.

The Eye Movement Test method 2500 then moves to step 2504 where the patient 214 observes the Test Display 514 and/or 518 and if they see the light stimulus they permit their eyes to move in the direction of the light stimulus in accordance with normal physiology.

As the Eye Movement Test method 2500 is being performed, steps 2505, 2506, 2507, 2508 and 2059 are being performed in a somewhat parallel fashion. At step 2505, the Eye Tracking software system configures the Eye Tracking Cameras 528 and 530 to record the movement of the eyes of the patient 214 on a continuous basis.

At step 2506, the Eye Tracking software system configures the Eye Tracking Cameras 528 and 530 to continuously send a video feed, which may be in an analog or digital format, to the SG100 Board 316.

At step 2507, the SG100 Board 316 sends the video feed to the PCIe Board 308.

At step 2508, the PCIe Board 308 sends the analog video feed continuously to the two Video Capture Cards 322 and 324 that will then convert the analog video feed to a digital video feed. At step 2510 the Video Capture Cards 322 and 324 will send the digital video feed to both the User Interface software system 2402 for displaying the video feed at the Technician Computer 208 for viewing by the Technician 216*a* and the Control Unit User Interface software system 2410 for displaying the video feed on the CU Display 320 for viewing by the Technician 216*b*.

At step 2509, the PCIe Board 308 also converts the analog video feed into numeric binary data, referred to as gaze data, that is then sent to the main memory 306 of the main processor 304 for processing by the Visual Test software system 2204 and the Eye Movement Algorithm.

After step 2509, the Eye Movement Test method 2500 moves to step 2511 where the Visual Test software system, in accordance with the Eye Movement Algorithm as described herein, configures the main processor 304 to analyze the gaze data once a stimulus has been presented to determine if a Responsive Eye Movement has occur. If no Responsive Eye Movement has been determined to occur, according to the Eye Movement Algorithm, within the Time Window but a blink has occurred within the Time Window then the Visual Test software system configures the main processor 304 to send a stimulus command to the HMU where the Firmware system configures the processor 304 to present the same light stimulus again.

The Eye Movement Test method 2500 then moves to step 2512 where, if the Visual Test software system 2404 determines that a Responsive Eye Movement has occurred, then it configures the main processor 304 to send a stimulus command to the Firmware system 2408 to configure the processor 504 for controlling the Test Display 514 or 518 to generate a light stimulus of lower intensity that is presented at the same location as the previous light stimulus to the patient 214 at steps 2512 and 2504. However, if the Visual Test software system 2404 determines that there has not been a Responsive Eye Movement then it configures the main processor 304 to send a stimulus command to the Firmware system 2408 to generate a light stimulus of greater intensity that is presented at the same location as the previous light stimulus to the patient 214 at steps 2512 and 2504.

Simultaneously, the Visual Test software system conducts Active False Positive tests at predetermined intervals to determine if an Active False Positive Event occurs.

Once the Eye Movement Test is completed, or alternatively during the performance of the Eye Movement Test, the method 2500 proceeds to step 2513 where the Visual Test software system 2404 sends the test result data that includes numeric values representing the Minimum Luminosity Level for each coordinate that was tested to the User Interface software system 2402.

The method 2500 may then proceed to step 2514 where the test result data is sent to the Statistical Analysis software system 2412 from the User Interface software system 2402. At step 2515, the test result data may be adjusted for age according to an aged-based algorithm described herein. The adjusted test result data is sent back to the User Interface software system 2402 which will then use the age-adjust test result data to generate a clinical test report for viewing by a clinician and/or eye doctor.

Advantages of Using a Visual Test Unit Having a CU and an HMU

As illustrated in FIG. 1 and FIG. 2, several Control Units may be connected to the Technician's computer 108, 208 permitting several vision tests to be conducted simultaneously on multiple patients 214*a*-214*c*. By this vision testing technology and methodology described herein, the Technician 216*a* may use their time more efficiently and consequently reduce the cost to the clinic or hospital of administering such tests. The User Interface software system will permit the Technician 216*a* to monitor multiple tests from the Technician Computer 108, 208 as illustrated in FIG. 32. For example, the Eye Tracking Cameras 528 and 530 in each HMU 102 may provide, in the manner described herein, the image of the eyes of the patients 214*a*-214*c* throughout the vision tests. Alternatively, or in addition thereto, the Visual Test software system may also provide to the User Interface software system the Minimum Luminosity Values for the coordinates tested as the vision test progresses which will appear in graphic form on the Technician Computer 108, 208 which will assist the Technician 216*a* in monitoring the progress of the vision tests.

In another aspect, the Conventional Gold Standard Devices must be used in a dedicated darkened testing room. In contrast, the provided Visual Test Units and associated test methodologies described herein do not need a dedicated darkened room but rather multiple Visual Test Units may be used in a single room as illustrated in FIG. 2 thereby reducing the space requirements for testing multiple patients 214*a*-214*c* while also providing for a reduced footprint for just a single Visual Test Unit.

In yet another aspect, the use of a CU 102 permits the weight of the HMU 104 to be kept to a minimum since many of the electronics can be housed within the CU 102. The weight of the HMU 104 is particularly important given that many glaucoma patients, who will be tested using the Visual Test Units described herein, are elderly or infirmed and will not be able to wear a helmet for a period of time when the helmet weighs too much and these patients will get fatigued which may affect their vision test results.

Alternative Embodiments

It should be understood that the Visual Test Unit described herein has the potential to be used for ancillary eye tests such as: (1) RAPD (Relative Afferent Pupillary Defect testing) and (2) Contrast Sensitivity Testing. This Visual Test Unit described herein may also be used for other vision tests such as, but not limited to, eye movements in concussion patients.

It should also be understood that several alternative embodiments were also described throughout the detailed description of the example embodiment.

Additional Embodiment of Head-Mounted Unit

Figure 33:
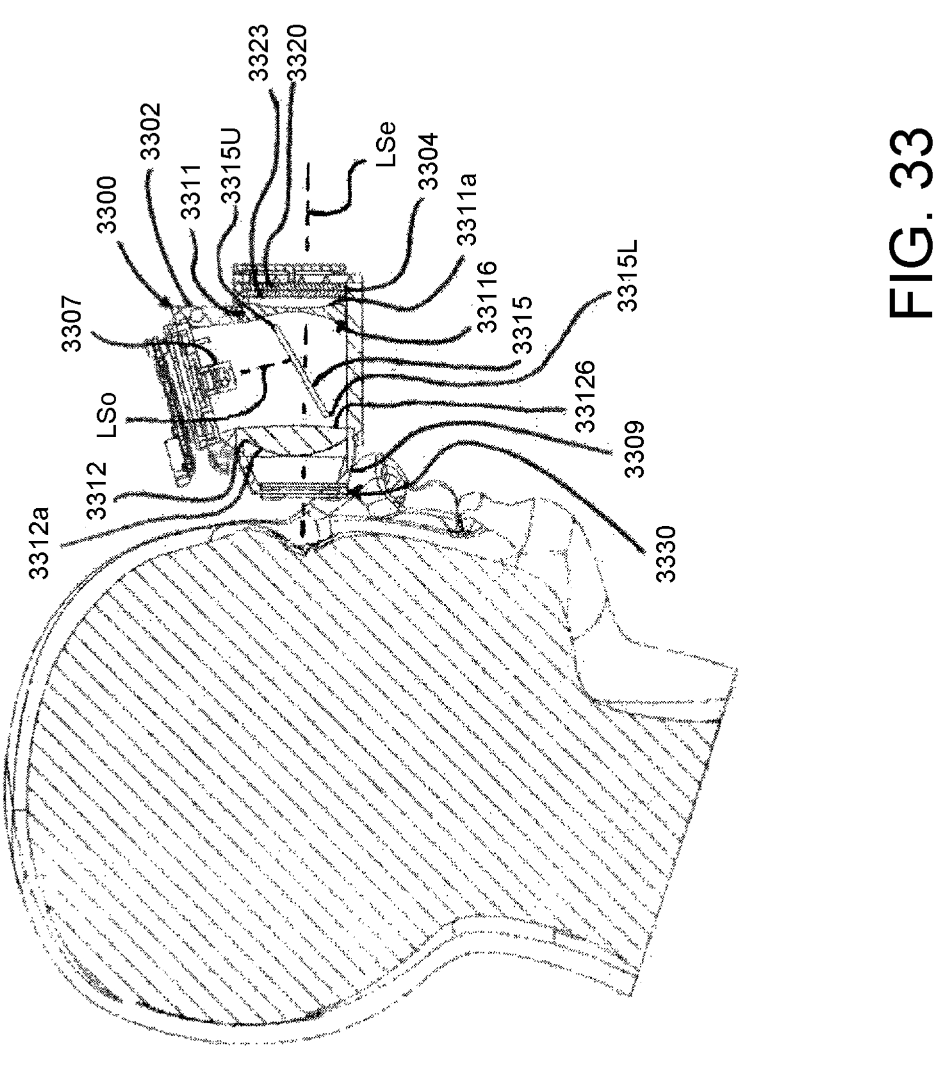
FIG. 33 is a cross-sectional view of another embodiment of HMU taken along line 33-33 in FIG. 34.
Figure 35:
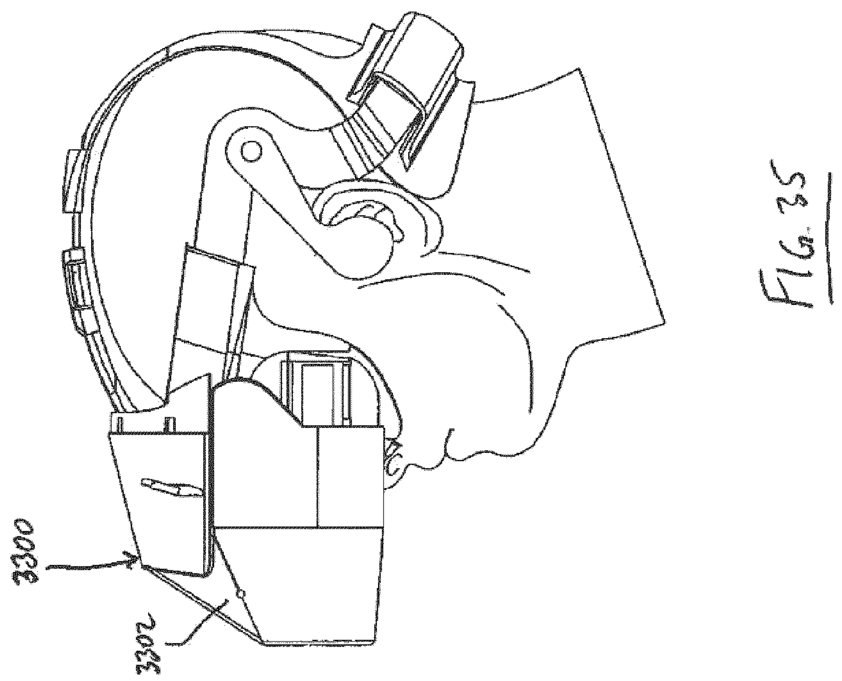
FIGS. 34 and 35 are front and side elevation views of the embodiment of HMU of FIG. 33.
Figure 34:
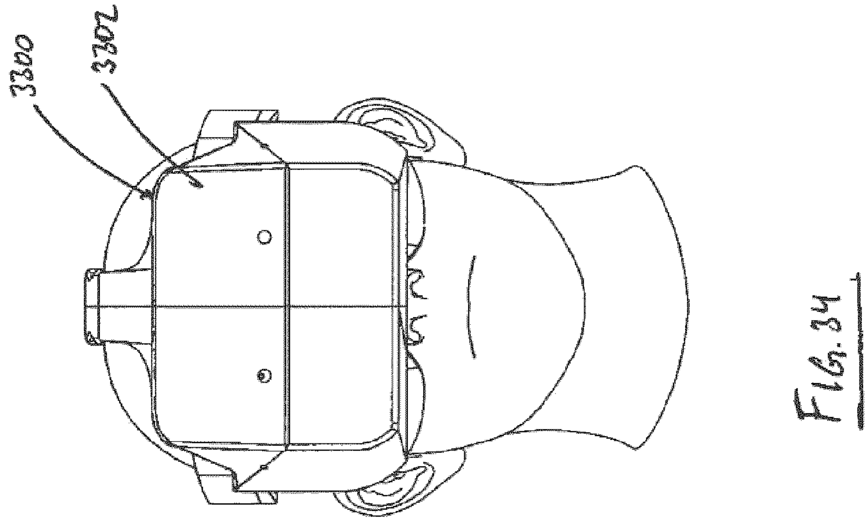
Figure 36:
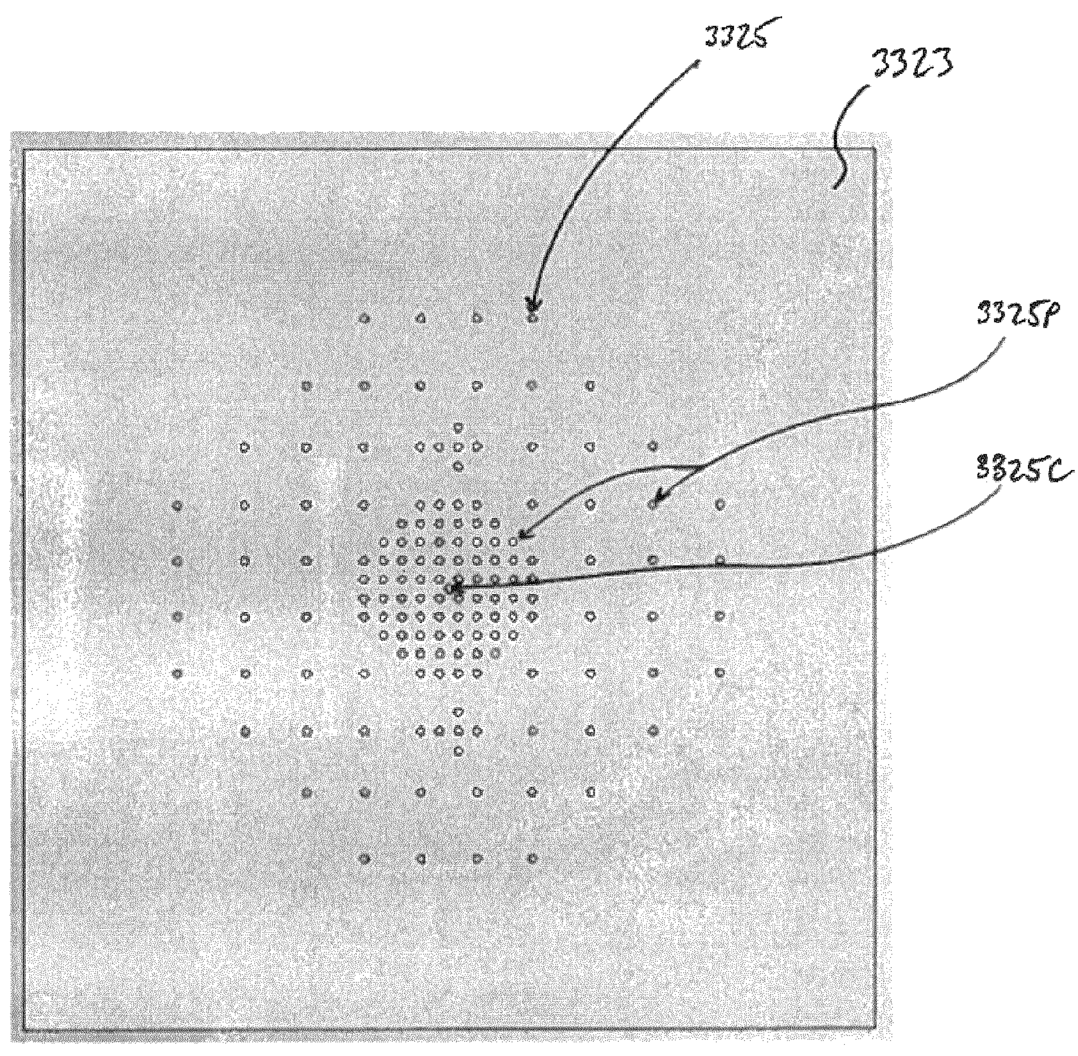
FIG. 36 is a front elevation view of a screen of an internal test display of the HMU embodiment of FIG. 33.

FIGS. 33-35 show another embodiment of a head mounted unit 3300 which has a different internal optical assembly 3301 configured for transmitting a light stimulus to the patient's eye than an optical assembly for performing substantially the same function in the embodiment of FIGS. 6-9 which is indicated at 104*p*. Additionally to transmitting the light stimulus to the patient's eye, the optical assembly is configured for transmitting reflected light transmitted into the housing from the patient's eye to a gaze sensor.

Generally speaking, and similarly to the earlier embodiment of head mounted unit as for example shown in FIGS.

6-9, the head mounted unit 3300 comprises a housing 3302 configured to be supported on the head of the patient using a similar support arrangement (see FIGS. 34-35) as that shown in relation to the embodiment 104*p*, an internal test display 3304 in the housing 3302 for generating the light stimulus to conduce movement of the patient's eye, a gaze sensor 3307 in the housing and configured to track the patient's eye by or based on light rays reflected therefrom, such as a camera as in the illustrated embodiments, and an eyepiece 3309 supported on the housing 3302 and configured to receive the patient's eye for viewing the light stimulus.

Regardless of embodiment of head mounted unit 104*p* or 3300, one of the gaze sensor and the internal test display is located along a line of sight $LS_E$ defined by the eyepiece 3309 but at a spaced distance therefrom, to define an in-line testing element. In the embodiment 104*p* of FIGS. 6-9, the gaze sensor is the in-line testing element, while in the instant embodiment 3300 the internal test display 3304 is the in-line testing element.

In order to fulfill both the functions of transmitting light between each pairing of (i) the internal test display and the patient's eye, and (ii) the patient's eye and the gaze sensor, and doing so within a common space defined by the housing 3302, the optical assembly 3301 comprises a plurality of lenses such as those indicated at 3311 and 3312, which are arranged to focus light from the in-line testing element onto the patient's eye received at the eyepiece 3309, and a mirror 3315 arranged to reflect light, transmitted through the eyepiece 3309 and into the housing 3302, to the other one of the gaze sensor and the internal test display located out of sight, that is beyond the user's field of vision into the housing 3302 that is defined or provided by the eyepiece 3309. It will be appreciated that lenses are primarily transmissive optical devices, meaning that a majority of light incident on a lens is transmitted therethrough and a minority portion of the incident light is reflected, while mirrors are primarily reflective optical devices, meaning that a majority of light incident on a mirror is reflected thereby and a minority portion of the incident light is transmitted through the mirror.

In the embodiment 3300, a first focusing lens 3311 of the optical assembly is disposed along the line of sight $LS_E$ and adjacent and in front of the in-line testing element, in this case test display 3304, so as to be intermediate the in-line testing element 3304 and the eyepiece 3309. The first focusing lens 3311 is configured to partially refract light rays emanating from the in-line testing element. In the embodiment 3300, the first focusing lens 3311 is configured to partially refract the light rays in a converging fashion so as to help to bring the rays to a focal point as they travel away from the in-line testing element and pass through the lens 3311.

Furthermore, there is a second focusing lens 3312 of the optical assembly disposed along the line of sight $LS_E$ and adjacent and behind the eyepiece 3309, so as to be intermediate the eyepiece and the in-line testing element. The second focusing lens 3312 is configured to refract the light rays transmitted through the first focusing lens 3311. Refraction by the second focusing lens 3312 in this particular embodiment is in a converging fashion, so as to bring the light rays to a focal point at the patient's eye received at the eyepiece.

In the embodiment 3300, the first and second focusing lenses 3311 and 3312 are the only lenses of the optical assembly. Thus, each of the first and second focusing lenses partially refracts the light emanating from the in-line testing element for focusing on the patient's eye received at the eyepiece.

The mirror 3315 is disposed along the line of sight $LS_E$ between the first and second focusing lenses 3311, 3312 and is configured to transmit light from the in-line testing element 3304 but reflect light from the eyepiece 3309 to the other one of the gaze sensor and the internal test display located out of sight, that is beyond the user's field of vision into the housing 3302 that is defined or provided by the eyepiece 3309.

In order to satisfactorily focus light from the in-line testing element to the patient's eye, the first and second focusing lenses 3311, 3312 are non-Fresnel lenses. More specifically, the first focusing lens 3311 is biconcave, and a proximal side 3311*a* of the first focusing lens to the in-line testing element 3304 has a smaller arc than an arc of an opposite side 3311*b* of the first focusing lens proximal to the mirror 3315. In contrast, the second focusing lens 3312 is biconvex, and a proximal side 3312*a* of the second focusing lens to the eyepiece 3309 has a larger arc than an arc of an opposite side 3312*b* of the second focusing lens proximal to the mirror 3315.

Since the mirror 3315 is located in a spatially intermediate position between the patient's eye and the in-line test element 3304, and provides reflection of light to the out-of-sight testing element, such that the mirror is spatially intermediate (relative to travelling light waves) between each pairing of (i) the eyepiece and the internal test display and (ii) the eyepiece and the gaze sensor, the mirror is configured to transmit light rays, which emanate from the in-line testing element 3304, having frequencies within a first frequency range and to reflect light rays, which emanate from the eyepiece 3309, having frequencies in a second frequency range distinct from the first frequency range.

In the illustrated embodiments, the first and second frequency ranges are a visible light range and an infrared range which has higher frequencies than visible light. The first frequency range is based on the in-line testing element, such that if this is the internal test display, which necessarily emanates visible light to be visible to the patient, than the first (transmissible) frequency range is the visible light range, but if the in-line testing element is the gaze sensor, which operates in a different electromagnetic frequency range so as to be able to spatially coexist with the visible light, than the transmissible frequency range is the infrared range. Therefore, the first or transmissible frequency range of the mirror 3315 may in some embodiments be lower than the second or reflectable frequency range, such as in the instant embodiment 3300, and higher in other embodiments, such as that of FIGS. 6-9.

The mirror 3315, which is supported in the housing, is oriented at an inclined angle and the out-of-sightline testing element, which in the embodiment 3300 is the gaze sensor 3307, is arranged beyond the line of sight $LS_E$ and in opposite relation to the mirror. For reflection between the out-of-sight element and the patient's eye, the mirror which is planar extends upwardly and rearwardly from a lower end 3315L to an upper end 3315U which is located closer to the in-line testing element than the mirror's lower end. Also, in the illustrated embodiment, the out-of-sightline testing element is the gaze sensor 3307.

The out-of-sightline testing element has a line of sight $LS_O$, which is located centrally thereof and oriented normal to a face thereof proximal to the mirror, that is transverse but not perpendicular to the line of sight LS of the eyepiece 3309. In other words, these distinct light of sights do not intersect on a common face of the mirror on which they are incident. The line of sight of the out-of-sightline testing element $LS_O$ is offset from a height center of the mirror between its upper and lower ends 3315U and 3315L.

It will be appreciated that the mirror 3315 is configured for transmission of light in the first frequency range without substantially any refraction, such that transmission of light in the first frequency range between the in-line testing element and the eyepiece is substantially uninterrupted by the mirror 3315.

To provide sufficient luminance, in other words brightness, of the light stimulus, the internal test display 3304 is in the form of an assembly comprising an array of light-emitting devices (LEDs) 3320 configured to emanate light towards the eyepiece 3309 and an opaque screen 3323 in front of the array of light-emitting devices 3320 and configured to block the light therefrom. The screen 3323 locates a plurality of openings 3325 to permit passage of light to the eyepiece 3309 at select locations of the patient's visual field. Thus, the screen openings may register with select ones of the LEDs in the array 3320.

The openings comprise a central opening 3325C in a center of the screen for a central fixation point of the vision test and a plurality of peripheral openings 3325P at spaced locations on the screen which are used for forming light stimuli in the patient's visual field.

In the illustrated embodiment, the openings 3323 are fixed such that light stimuli are formed by illuminating portions of the LED array 3320 but not the whole array. For example, specific designated areas of the LED array may be used to form one of a predetermined set of light stimuli, which can be varied in intensity by toggling a number of LEDs in the designated area of the array that are active or on so as to be illuminated and emanate light.

The eyepiece 3309 comprises a corrective lens assembly 3330 arranged in front of the patient's eye, that is on a distal side of the eyepiece to the second focusing lens 3312. The spherical adjustment mechanism shown and described in conjunction with the embodiment of FIGS. 6-9 is not suitable for the instant embodiment of head mounted unit.

An eye illuminative device 3333 is supported externally of the housing 3302 above the eyepiece 3309 to illuminate a space in front of the patient's eye for improved tracking by the gaze sensor 3307. However, in other embodiments, this eye illumination device 3333 can be internal to the housing 3302 and incorporated as part of the gaze sensor 3307.

FIGS. 37 and 38A-C show an embodiment of head mounted unit 3300' similar to the embodiment 3300 but in which a computing device 3336, which includes one or more boards 3304A, 3307A with processors and operatively interconnected memories to drive the internal test display 3304 and the gaze sensor 3307, are carried by the head mounted unit instead of a control unit.

Figure 37:
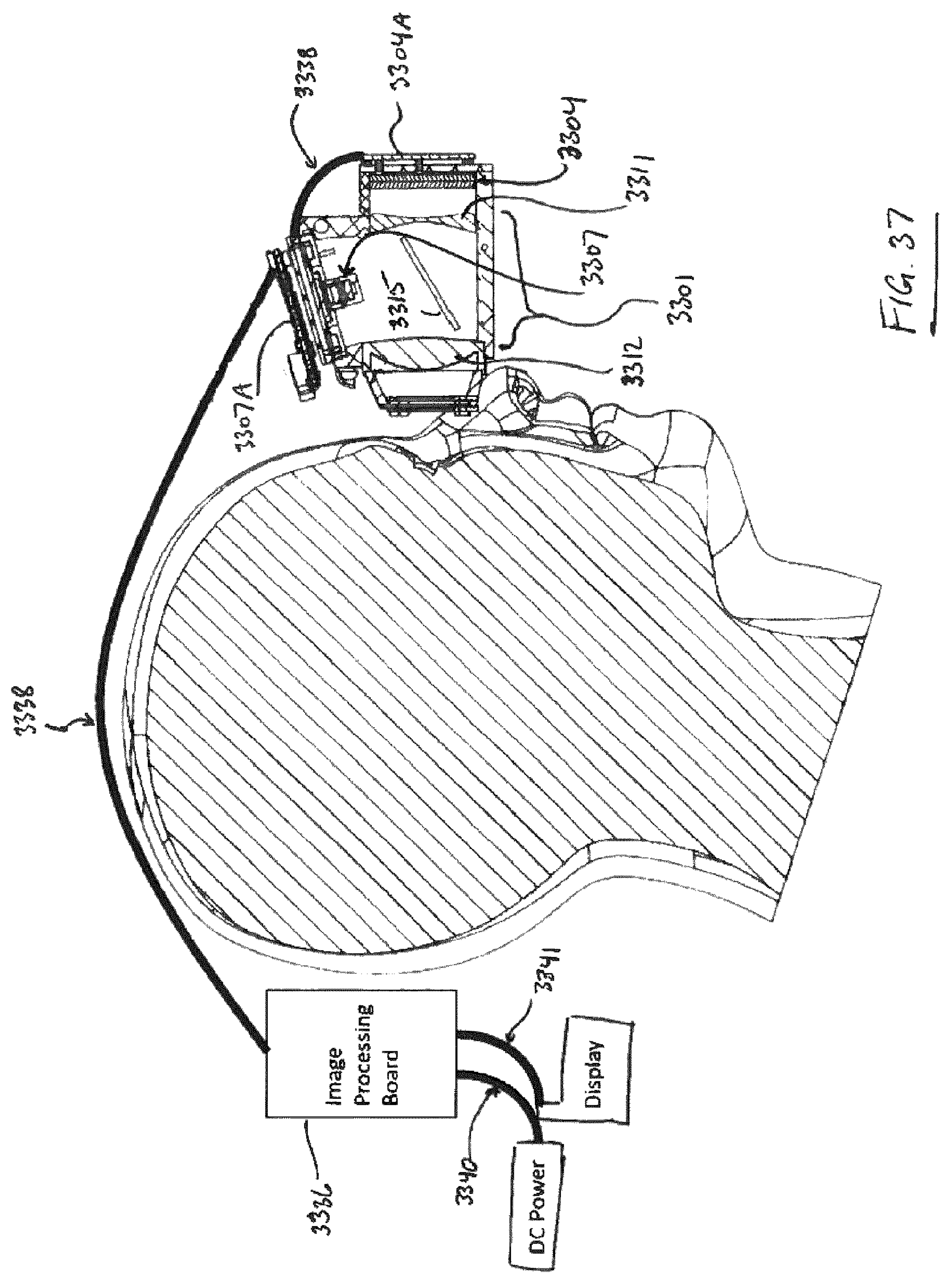
FIG. 37 is a cross-sectional view similar to FIG. 33 but showing a further embodiment of HMU.
Figure 38A:
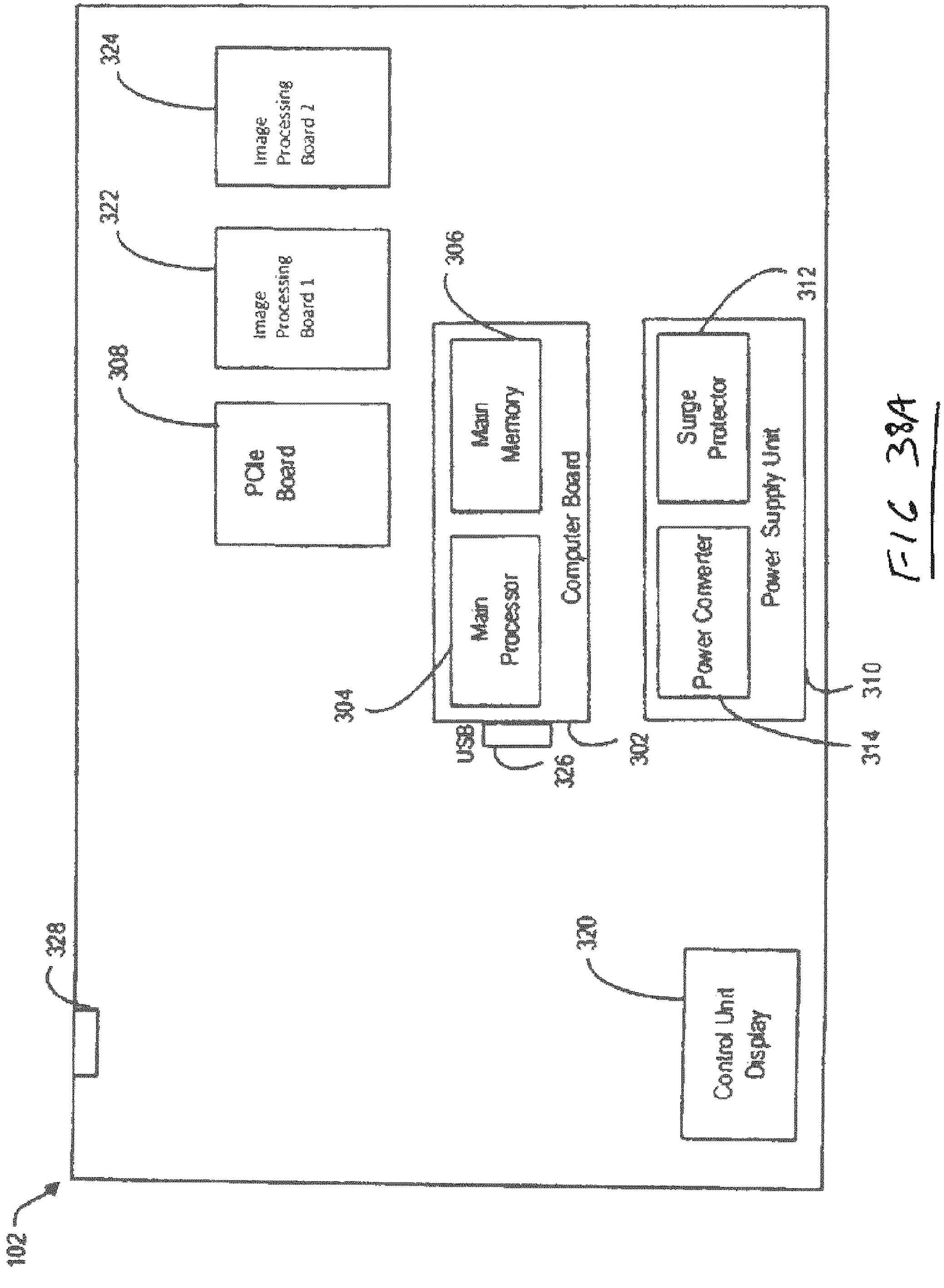
FIGS. 38A through 38C respectively show a schematic diagram of electrical components of the HMU of FIG. 37, power flow therethrough, and data flow therethrough.
Figure 38B:
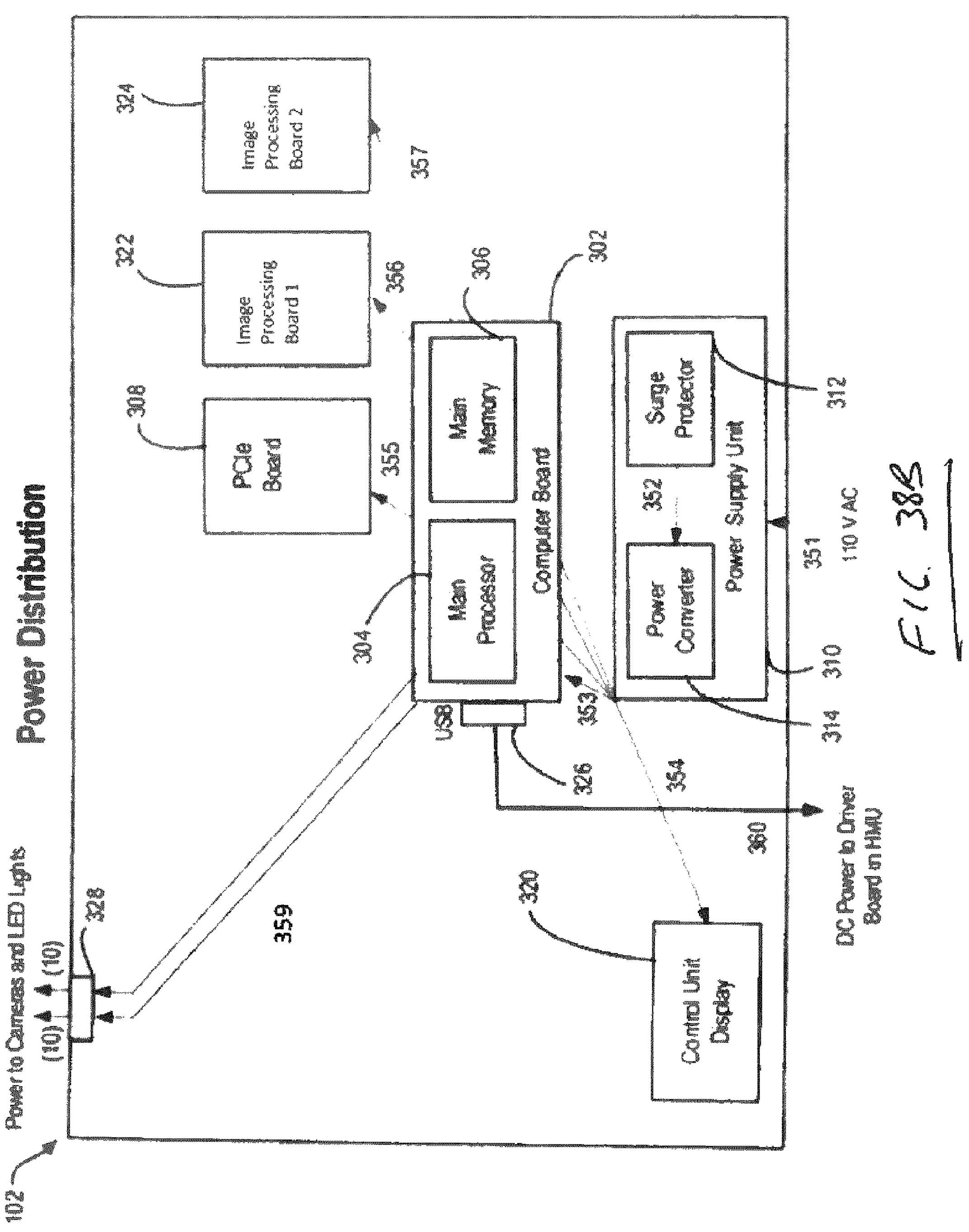
Figure 38C:
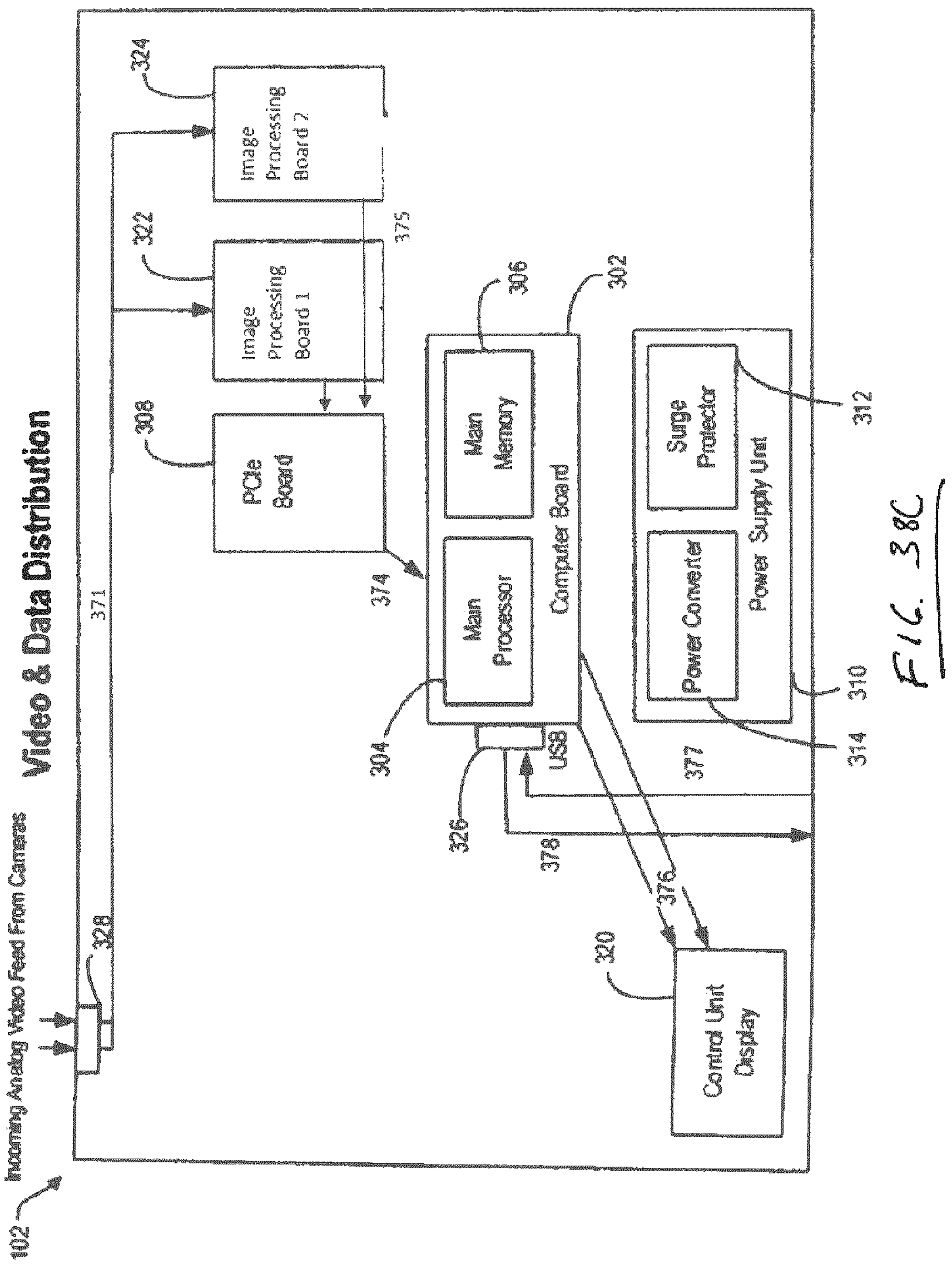

Basically, a computing device illustrated in FIGS. 3A through 3C is moved from a distinct device in the form of a control unit to the head mounted unit where it may be supported on a rear of the patient's head. In FIG. 37, the internal test display 3304 and the gaze sensor 3307 are connected to the computing device 3336 by cables 3338. The computing device 3336 is connected to a suitable power source at 3340 and to a display device at 3341.

As described hereinbefore in relation to the second embodiment of head mounted unit 3300, the same comprises an optical, two lens, non-Fresnel design which provides several advantages over the single lens Fresnel or non-Fresnel design of typical virtual reality head-mounted devices (HMDs) or other multi-lens optical systems that have been designed for visual field testing and is non-inferior to the current gold standard. The two lens system is light-weight, simple, but also is designed to allow for non-inferior visual field testing. The optical system light source is a custom LED array that is of a very specific size with a mask that allows for modifications to the location and shape of each stimuli in the visual field to correct for distortions from the optical system. Immediately in front of the LED array is the first lens in the barrel. Then, there is a cold mirror that is used to reflect infrared light coming from the eye up to an infrared sensor for eye-tracking purposes. Finally, there is the lens at the front of the system. The distance and power of the lenses are designed to allow for enough space for the mirror and minimization of distortion and aberrations. The system is also unique in that it allows for the placement of loose lenses after the final lens for refractive error correction without creating significant distortions and aberrations. The entire system is designed so that stimuli are of the appropriate size and clarity, and in the appropriate locations.

In Closing

As described hereinbefore, the present invention generally relates to an apparatus for administering a vision test to a patient 214, particularly that of the type that conduces movement of the eye, specifically a pupil thereof, and tracks the same.

The apparatus comprises a visual test unit, for example that collectively formed by control unit CU 102/202 and head-mounted unit HMU 104/204, that is configured to receive a face of the patient and to perform the vision test on the patient. Generally speaking, the visual test unit includes (i) an internal test display, such as that indicated at 804 or 3304, arranged in front of the patient's face 214 and configured to generate a light stimulus to conduce movement of an eye of the patient, and (ii) a gaze sensor, such as that indicated at 814 or 3307, configured to track the eye of the patient. The gaze sensor may alternatively be referred to as a gaze tracker, but in the illustrated embodiments this is a camera configured to capture a video of the eye of the patient.

In one embodiment, such as that shown in FIGS. 1-2, there are provided a plurality of the visual test units forming a system 100 for use by a technician 216*a* to administer vision tests on a plurality of patients 214*a* through 214*c*, in which each of the visual test units 202*a*/204*a* through 202*c*/204*c* is assigned to a different one of the patients to which the visual test unit is assigned, as more clearly shown in FIG. 2.

In such a system as 100, each visual test unit is configured to receive, as input, parameters for configuring the visual test unit for the vision test to be performed thereon, where the parameters are associated with the different one of the patients to which the visual test unit is assigned. Typically, and with reference to FIG. 27, the parameters include at least one of: (i) an eye to be tested 2716, (ii) a grid testing area for defining locations where light stimuli are presented in a visual field of the patient 2710; and (iii) corrective lens prescription 2722, 2726. Other parameters for calibrating a vision test for a specific patient may include at least one of (iv) interpupillary distance 2724; (v) stimulus size for defining a size of the light stimulus 2728; (vi) patient response type 2712, for example clicker or saccade central, for identifying a format of input received from the patient to signal observance of a light stimulus; (vii) test strategy 2714, for example ZEST or Full Threshold, (viii) background colour 2718; and (ix) test foveal threshold 2720, which is toggled on or off.

The system further includes a computing device, such as that indicated at 108/208, operatively communicated with the visual test units and configured to receive, as input from the technician 216A, the parameters for communication to the visual test units to configure same for the various patients. Generally speaking, the computing device for the technician comprises a processor and a memory operatively coupled thereto and storing instructions to be executed on the processor, in this case for controlling the visual test units to which the technician computing device is operatively communicated.

Such an embodiment of system of multiple visual test units is thus suited for enabling a single technician to carry out vision tests on different patients in parallel, or in other words concurrently.

In the illustrated embodiments, the gaze sensor or tracker comprises a camera configured to capture a video of the eye of the patient. More specifically, the camera of the illustrated embodiments is configured to receive infrared light to capture images, in this case of the patient's eye.

In some embodiments, the apparatus for vision testing includes a technician display, such as that indicated at 108/208 or 320, configured to display the video to the technician 216*a* administering the vision test in order to monitor the patient.

In the illustrated embodiment of the apparatus includes a technician device, such as that indicated at 108/208, distinct from the visual test unit which is operatively communicated with the visual test unit and configured to control the visual test unit, and the technician device includes the technician display such that the video of the patient's eye is remotely observable.

In the illustrated embodiments, the visual test unit comprises a head mounted unit HMU such as that indicated at 104/204, 104*p* or 3300 configured for mounting to the head of the assigned patient.

In the illustrated embodiments, the head mounted unit includes the gaze sensor 814 or 3307, which more specifically is in the form of a camera.

In one embodiment, the visual test unit includes the technician display 320 which is external such that the video is observable by the technician for aligning the head mounted unit on the patient. In this embodiment, the technician display 320 is a component of the control unit CU 102/202 which carries the processor configured to execute instructions to perform the vision test.

In one embodiment, the technician display is distinct from the head mounted unit. More specifically, in the embodiment shown in FIG. 4, the technician display 320 is part of the control unit of the visual test unit.

In some embodiments, the visual test unit is configured to detect an adverse testing condition of the patient under which inaccurate results of the vision test are obtained, and to pause the vision test in response to detection of the adverse testing condition.

Preferably, the visual test unit is configured to resume the paused vision test in response to determination that the adverse testing condition is removed.

In some embodiments, the head mounted unit further includes a head tilt sensor, such as that indicated at 510, configured to detect a tilt angle of a head of the patient relative to a vertical plane. For example, the head tilt sensor comprises a gyroscope.

Preferably, the head tilt sensor is also configured to detect a tilt angle of the head of the assigned patient relative to a reference tilt angle of the patient's head in a relaxed position.

In such embodiments, the visual test unit is configured to pause the vision test for the patient in response to a detected tilt angle exceeding a prescribed threshold angle. Typically, the test is paused when the tilt angle exceeds the prescribed threshold for a threshold duration. In the illustrated embodiment, the prescribed threshold angle is about 20 degrees.

In addition, in some embodiments the gaze sensor 814 or 3307 is configured to detect closure of the eye, and another adverse testing condition comprises a closed eye, such that the vision test can be paused responsive to detection thereof.

Typically, as in the illustrated embodiments, the visual test unit includes an eyepiece, such as that indicated at 1016 or 3309, that is configured to receive the patient's eye for viewing the light stimulus. The eyepiece is supported on the housing 601 or 3302 of the head mounted unit, as shown more clearly in FIGS. 10 and 33. The eyepiece 1016 or 3309 is in front of the internal test display 804 or 3304, and notably in the embodiment 3300 the eyepiece is in opposite relation to the internal test display.

In the embodiment 3300, the internal test display 3304 comprises an array of light-emitting devices 3320 configured to emanate light towards the eyepiece 3309 and an opaque screen 3323 in front of the array of light-emitting devices 3320 and configured to block the light therefrom. However, the screen 3323 locates a plurality of openings 3325 to permit passage of light to the eyepiece 3309 at select locations of the patient's visual field. In this manner, the LED array and screen cooperate to form the light stimulus.

Preferably, the openings comprise a central opening 3325C in a center of the screen for a central fixation point of the vision test and a plurality of peripheral openings 3325P at spaced locations on the screen.

In the illustrated embodiments, the head mounted unit further includes an optical assembly in the housing of the HMU, such as that indicated at 802 or 3301, and configured for transmitting the light stimulus to the eyepiece and light, emanating from the eye of the patient, from the eyepiece to the gaze sensor. Basically, the optical assembly is an assembly of optical devices which are either transmissive or reflective to direct light between the internal test display, the eyepiece and the gaze tracker.

In the illustrated embodiments, one of the gaze sensor and the internal test display is located along a line of sight defined by the eyepiece but at a spaced distance therefrom, to define an in-line testing element. In other words, the in-line testing element is located substantially at eye level and is spaced horizontally away from the eyepiece.

In the illustrated embodiments, the optical assembly 802 or 3301 comprises a plurality of lenses arranged to focus light emanating from the in-line testing element and onto the patient's eye received at the eyepiece, and a mirror arranged to reflect light, transmitted through the eyepiece and into the housing, to another one of the gaze sensor and the internal test display.

In one embodiment, the visual test unit includes a patient input device, such as that indicated at 218, configured to receive input from the patient to signal observance of a light stimulus in the visual field around a fixation point during the vision test. In such an embodiment, the visual test unit is configured to:

monitor gaze of the patient at the fixation point during the vision test, and if the gaze of the patient is determined to have moved from the fixation point during the vision test, then pause the vision test, and resume the vision test when the gaze of the patient is determined to have returned to the fixation point.

No Limiting of Embodiments

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. An apparatus for administering a visual field test to a patient comprising:

a visual test unit configured to receive a face of the patient and to perform the visual field test on the patient, wherein the visual test unit includes:

an internal test display arranged in front of the patient's face and a light stimulus device configured to generate a light stimulus to an eye of the patient; and a camera configured to track movement of the eye of the patient;

wherein the visual test unit comprises a head mounted unit having a housing configured for mounting to the head of the patient;

wherein the housing carries the internal test display and the camera;

wherein the camera is configured to track the eye of the patient by light rays reflected therefrom;

wherein the head mounted unit includes an optical assembly in the housing and configured for transmitting the light stimulus from the light stimulus device to the eye and light emanating from the eye of the patient to the camera;

wherein the light stimulus device comprises an array of light-emitting devices configured to transmit light towards the eye and at least one opaque screen in front of the array of light-emitting devices which defines an array of openings at positions registered with respective ones of the light emitting devices in the array to permit passage of light from each light-emitting device through its respective opening to the eye and to block light from others of the array of light-emitting devices;

wherein the optical assembly comprises a plurality of lenses arranged to focus light emanating from the light stimulus device along a line of sight and onto the patient's eye;

wherein the light stimulus device has a level of intensity and the optical assembly has a level of attenuation caused by the optical assembly which are together arranged such that the light stimulus reaching the eye is at least about 3,200 Nts;

wherein the camera is located at a position off the line of sight;

wherein the optical assembly comprises a hot mirror arranged in the line of sight;

the hot mirror being arranged to transmit light emanating from the light stimulus device along the line of sight and onto the patient's eye;

the hot mirror being arranged to reflect light from the eye onto the camera;

wherein the hot mirror is configured to transmit the light emanating from the light stimulus device having frequencies within a first frequency range and to reflect the light which emanate from the eye to the camera having frequencies in a second frequency range distinct from the first frequency range;

wherein the plurality of lenses on the line of sight includes a first focusing lens disposed along the line of sight adjacent the light stimulus device;

wherein the plurality of lenses includes a second focusing lens disposed along the line of sight and adjacent the eye;

wherein the first and second focusing lenses are the only lenses of the optical assembly;

wherein the hot mirror is located between the first and second focusing lenses;

wherein the first focusing lens adjacent to the eye of the patient is biconvex and wherein a side of the second focusing lens closest to the eye has a larger radius of curvature than the radius of curvature of an opposite side of the second focusing lens;

wherein the first focusing lens closest to the light stimulus device is biconcave and wherein a side of the first focusing lens closest to the eye of the patient has a smaller radius of curvature than the radius of curvature of the side of the first focusing lens closest to the light stimulus device.

2. The apparatus of claim 1 wherein there are provided a plurality of the visual test units forming a system for use by a technician to administer the visual field tests on a plurality of patients, wherein each of the visual test units is assigned to a different one of the patients;

wherein each visual test unit is configured to receive, as input, parameters for configuring the visual test unit for the visual field test to be performed thereon, wherein the parameters are associated with said different one of the patients to which the visual test unit is assigned, wherein the parameters include at least one of: (i) an eye to be tested, (ii) a grid testing area for defining locations where light stimuli are presented in a visual field of the patient; and (iii) corrective lens prescription; and wherein the system further includes a computing device operatively communicated with the visual test units and configured to receive, as input from the technician, the parameters for communication to the visual test units.

3. The apparatus of claim 1 wherein the apparatus further includes a technician display configured to display the video to a technician administering the visual field test in order to monitor the patient.

4. The apparatus of claim 3 further including a technician device distinct from the visual test unit which is operatively communicated with the visual test unit and configured to control the visual test unit, and wherein the technician device includes the technician display such that the video is remotely observable.

5. The apparatus of claim 3 wherein the technician display is external such that the video is observable by the technician for aligning the head mounted unit on the patient.

6. The apparatus of claim 5 wherein the technician display is distinct from the head mounted unit.

7. The apparatus of claim 1 wherein the visual field test unit is configured to detect an adverse testing condition of the patient under which inaccurate results of the visual field test are obtained, and wherein the visual test unit is configured to pause the visual field test in response to detection of the adverse testing condition.

8. The apparatus of claim 7 wherein the visual test unit is configured to resume the paused visual field test in response to determination that the adverse testing condition is removed.

9. The apparatus of claim 7 wherein the head mounted unit further includes a head tilt sensor configured to detect a tilt angle of a head of the patient relative to a vertical plane, and wherein the visual test unit is configured to pause the visual field test for the patient in response to a detected tilt angle exceeding a prescribed threshold angle.

10. The apparatus of claim 9 wherein the head tilt sensor is also configured to detect a tilt angle of the head of the patient relative to a reference tilt angle of the patient's head in a relaxed position.

11. The apparatus of claim 7 wherein the camera is configured to detect closure of the eye and wherein the adverse testing condition comprises a closed eye.

12. The apparatus of claim 1 wherein the camera has a line of sight which is transverse but not perpendicular to the line of sight.

13. The apparatus of claim 1 wherein the line of sight of the camera is offset from a height center of the mirror between its upper and lower ends.

14. An apparatus for administering a Conventional Gold Standard visual field test defined to determine sensitivity of a patient's visual system at various locations eccentric to the central fixation point in order to create a map of the patient's visual field comprising:

a visual field test unit configured to receive a face of the patient and to perform the visual field test on the patient, wherein the visual field test unit includes:

a light stimulus device configured to generate a light stimulus to an eye of the patient;

wherein the light stimulus device comprises an array of light-emitting devices configured to transmit light and at least one opaque screen in front of the array of light-emitting devices;

wherein said at least one opaque screen defines an array of openings at positions registered with respective ones of the light emitting devices in the array to permit passage of light from each light-emitting device through its respective opening and to block light from others of the array of light-emitting devices;

wherein the light emitting devices of the array are located at specific coordinates of the visual field which coordinates are determined by the Conventional Gold Standard visual field test;

wherein the patient indicates recognition of the stimuli by a response and the test report presents a visual grid which maps the lowest intensity level of light stimulus recognized by the patient at each coordinate of the visual field tested;

wherein the optical assembly comprises a plurality of focusing lenses arranged to focus light emanating from the light stimulus device along a line of sight and onto the patient's eye;

wherein the light stimulus device has a level of intensity and the optical assembly has a level of attenuation caused by the optical assembly which are together arranged such that the light stimulus reaching the eye is at least about 3,200 Nts.

15. An apparatus for administering a Conventional Gold Standard visual field test defined to determine sensitivity of a patient's visual system at various locations eccentric to the central fixation point in order to create a map of the patient's visual field comprising:

a visual test unit configured to receive a face of the patient and to perform the visual field test on the patient, wherein the visual test unit includes:

a light stimulus device configured to generate a light stimulus to an eye of the patient;

wherein the light stimulus device comprises an array of light-emitting devices configured to transmit light and at least one opaque screen in front of the array of light-emitting devices;

wherein said at least one opaque screen defines an array of openings at positions registered with respective ones of the light emitting devices in the array to permit passage of light from each light-emitting device through its respective opening and to block light from others of the array of light-emitting devices;

wherein the light emitting devices of the array are located at specific coordinates of the visual field which coordinates are determined by the Conventional Gold Standard visual field test;

wherein the patient indicates recognition of the stimuli by a response and the test report presents a visual grid which maps the lowest intensity level of light stimulus recognized by the patient at each coordinate of the visual field tested;

wherein the optical assembly comprises a plurality of focusing lenses arranged to focus light emanating from the light stimulus device along a line of sight and onto the patient's eye;

wherein the light stimulus device has a level of intensity and the optical assembly has a level of attenuation caused by the optical assembly which are together arranged such that the light stimulus reaching the eye is at least about 3,200 Nts;

wherein the optical assembly is arranged such that there is a second focusing lens closest to the eye of the patient, a hot mirror and then a first focusing lens, followed by said at least one opaque filter and the array of light emitting devices;

wherein the second focusing lens adjacent to the eye of the patient is biconvex and wherein a side of the second focusing lens closest to the eye has a larger radius of curvature than the radius of curvature of an opposite side of the second focusing lens;

wherein the first focusing lens closest to the light stimulus device is biconcave and wherein a side of the first second focusing lens closest to the eye of the patient has a smaller radius of curvature than the radius of curvature of the side of the first focusing lens closest to the light stimulus device;

wherein the hot mirror situated between the first and second focusing lenses is configured to transmit light emanating from the array of light emitting devices having frequencies within the first frequency range and to reflect light in a second frequency range such that a camera provides a video of the eye of the patient;

wherein the optical assembly is configured to permit the patient to see all of the light stimuli presented within the visual field of the patient;

wherein the camera is aligned at an angle to the side of the mirror closest to the eye of the patient.

16. An apparatus for administering a Conventional Gold Standard visual field test defined to determine sensitivity of a patient's visual system at various locations eccentric to the central fixation point in order to create a map of the patient's visual field comprising:

a visual test unit configured to receive a face of the patient and to perform the visual field test on the patient, wherein the visual field test unit includes:

a light stimulus device configured to generate a light stimulus to an eye of the patient;

a camera configured to track movement of the eye of the patient;

wherein the visual field test unit comprises a head mounted unit having a housing configured for mounting to the head of the patient;

wherein the housing carries an internal test display and the camera;

wherein the camera is configured to track the eye of the patient by light rays reflected therefrom;

wherein the head mounted unit includes an optical assembly in the housing and configured for transmitting the light stimulus from the light stimulus device to the eye and light emanating from the eye of the patient to the camera;

wherein the optical assembly comprises a plurality of focusing lenses arranged to focus light emanating from the light stimulus device along a line of sight and onto the patient's eye;

wherein the light stimulus device has a level of intensity and the optical assembly has a level of attenuation caused by the optical assembly which are together arranged such that the light stimulus reaching the eye is at least about 3,200 Nts;

wherein the camera is located at a position off the line of sight;

wherein the optical assembly comprises a hot mirror arranged in the line of sight;

the hot mirror being arranged to transmit light emanating from the light stimulus device along the line of sight and onto the patient's eye;

the hot mirror being arranged to reflect light from the eye onto the camera;

wherein the plurality of focusing lenses on the line of sight includes a first focusing lens disposed along the line of sight adjacent the light stimulus device;

wherein the plurality of focusing lenses includes a second focusing lens disposed along the line of sight and adjacent the eye;

wherein the first and second focusing lenses are the only lenses of the optical assembly;

wherein the hot mirror is located between the first and second focusing lenses;

wherein the second focusing lens adjacent to the eye of the patient is biconvex and wherein a side of the second focusing lens closest to the eye has a larger radius of curvature than the radius of curvature of an opposite side of the second focusing lens;

wherein the first focusing lens closest to the light stimulus device is biconcave and wherein a side of the first focusing lens closest to the eye of the patient has a smaller radius of curvature than the radius of curvature of the side of the second focusing lens closest to the light stimulus device;

wherein the light stimulus device forms an array of light emitting devices located at specific coordinates of the visual field which coordinates are determined by the Conventional Gold Standard visual field test;

wherein the patient indicates recognition of the stimuli by a response and the test report presents a visual grid which maps the lowest intensity level of light stimulus recognized by the patient at each coordinate of the visual field tested.

17. The apparatus of claim 14 wherein the apparatus further includes a technician display distinct from the visual test unit which is operatively communicated with the visual test unit and configured to control the visual test unit, and wherein the technician device includes the technician display such that the video is remotely observable.

18. The apparatus of claim 14 wherein the visual test unit is configured to detect an adverse testing condition of the patient under which inaccurate results of the visual field test are obtained, and wherein the visual test unit is configured to pause the visual field test in response to detection of the adverse testing condition and to resume the paused visual field test in response to determination that the adverse testing condition is removed.

19. The apparatus of claim 18 wherein the head mounted unit further includes a head tilt sensor configured to detect a tilt angle of a head of the patient relative to a vertical plane, and wherein the visual test unit is configured to pause the visual field test for the patient in response to a detected tilt angle exceeding a prescribed threshold angle.

20. The apparatus of claim 18 wherein the camera is configured to detect closure of the eye and wherein the adverse testing condition comprises a closed eye.

21. The apparatus of claim 15 wherein the apparatus further includes a technician display distinct from the visual test unit which is operatively communicated with the visual test unit and configured to control the visual test unit, and wherein the technician device includes the technician display such that the video is remotely observable.

22. The apparatus of claim 15 wherein the visual test unit is configured to detect an adverse testing condition of the patient under which inaccurate results of the visual field test are obtained, and wherein the visual test unit is configured to pause the visual field test in response to detection of the adverse testing condition and to resume the paused visual field test in response to determination that the adverse testing condition is removed.

23. The apparatus of claim 22 wherein the head mounted unit further includes a head tilt sensor configured to detect a tilt angle of a head of the patient relative to a vertical plane, and wherein the visual test unit is configured to pause the visual field test for the patient in response to a detected tilt angle exceeding a prescribed threshold angle.

24. The apparatus of claim 22 wherein the camera is configured to detect closure of the eye and wherein the adverse testing condition comprises a closed eye.

25. The apparatus of claim 16 wherein the apparatus further includes a technician display distinct from the visual test unit which is operatively communicated with the visual test unit and configured to control the visual test unit, and wherein the technician device includes the technician display such that the video is remotely observable.

26. The apparatus of claim 16 wherein the visual test unit is configured to detect an adverse testing condition of the patient under which inaccurate results of the visual field test are obtained, and wherein the visual test unit is configured to pause the visual field test in response to detection of the adverse testing condition and to resume the paused visual field test in response to determination that the adverse testing condition is removed.

27. The apparatus of claim 26 wherein the head mounted unit further includes a head tilt sensor configured to detect a tilt angle of a head of the patient relative to a vertical plane, and wherein the visual test unit is configured to pause the visual field test for the patient in response to a detected tilt angle exceeding a prescribed threshold angle.

28. The apparatus of claim 26 wherein the camera is configured to detect closure of the eye and wherein the adverse testing condition comprises a closed eye.

* * * * *